United States Patent [19]

Fuhrer et al.

[11] Patent Number: 4,613,676
[45] Date of Patent: Sep. 23, 1986

[54] SUBSTITUTED 5-AMINO-4-HYDROXYVALERYL DERIVATIVES

[75] Inventors: Walter Fuhrer, Frenkendorf; Peter Bühlmayer, Arlesheim; Vittorio Rasetti, Basel; Bernhard Riniker, Frenkendorf, all of Switzerland

[73] Assignee: Ciba-Geigy Corporation, Ardsley, N.Y.

[21] Appl. No.: 671,261

[22] Filed: Nov. 14, 1984

[30] Foreign Application Priority Data

Nov. 23, 1983 [CH] Switzerland .................. 6285/83

[51] Int. Cl.$^4$ .................. C07C 101/30; C07C 69/74; C07C 101/72; C07C 61/08
[52] U.S. Cl. .................. 560/39; 560/125; 560/170; 562/444; 562/507; 562/567
[58] Field of Search .................. 562/567, 444, 507; 560/39, 125, 170

[56] References Cited

U.S. PATENT DOCUMENTS

| | | | |
|---|---|---|---|
| 4,198,398 | 4/1980 | Hudson et al. .................. | 424/177 |
| 4,304,715 | 12/1981 | Hudson et al. .................. | 260/112.5 R |
| 4,424,207 | 1/1984 | Szelke et al. .................. | 424/177 |

FOREIGN PATENT DOCUMENTS 104041 3/1984 European Pat. Off. .
WO84/03044 8/1984 PCT Int'l Appl. .

OTHER PUBLICATIONS

Chem. Abstr. vol. 101, (1984) 125684m.

Tetrahedron Letters, vol. 23, No. 25, pp. 2533-2534 (1982).
M. Szelke et al., "Peptides: Structure and Function", Proceedings of the 8th American Peptide Symposium 579-582 (1983).
M. W. Holladay and D. H. Rich, Tetrahedron Letters 24, 4401-4404 (1983).

Primary Examiner—Delbert R. Phillips
Attorney, Agent, or Firm—Michael W. Glynn; Irving M. Fishman

[57] ABSTRACT

Compounds of the formula

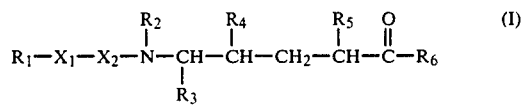

in which $R_1$ represents hydrogen or acyl, $X_1$ represents an optionally N-alkylated amino acid residue that is bonded N-terminally to $R_1$ and C-terminally to $X_2$, $X_2$ represents an optionally N-alkylated amino acid residue that is bonded N-terminally to $X_1$ and C-terminally to the group $-NR_2-$, $R_2$ represents hydrogen or lower alkyl, $R_3$ represents hydrogen, alkyl, cycloalkyl, aryl-lower alkyl or aryl, $R_4$ represents hydroxy or etherified or esterified hydroxy, $R_5$ represents alkyl, cycloalkyl, aryl-lower alkyl or aryl, and $R_6$ represents free or substituted amino or substituted hydroxy, and salts of such compounds having salt-forming groups inhibit the blood pressure-increasing action of the enzyme renin and can be used as anti-hypertensives.

3 Claims, No Drawings

SUBSTITUTED 5-AMINO-4-HYDROXYVALERYL DERIVATIVES

The invention relates to substituted 5-amino-4-hydroxyvaleryl derivatives of the formula

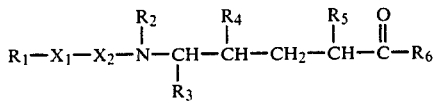

in which
$R_1$ represents hydrogen or acyl,
$X_1$ represents an optionally N-alkylated natural amino acid residue that is bonded N-terminally to $R_1$ and C-terminally to $X_2$,
$X_2$ represents an optionally N-alkylated natural amino acid residue that is bonded N-terminally to $X_1$ and C-terminally to the group $-NR_2-$,
$R_2$ represents hydrogen or lower alkyl,
$R_3$ represents hydrogen, alkyl, cycloalkyl, aryl-lower alkyl or aryl,
$R_4$ represents hydroxy or etherified or esterified hydroxy,
$R_5$ represents alkyl, cycloalkyl, aryl-lower alkyl or aryl, and
$R_6$ represents substituted or free amino or substituted hydroxy,
with the exception of compounds in which R1 represents an optionally N-acylated residue of the amino acid L-proline or in which $X_1$ and $X_2$ together represent -Val-Val-, -Gly-Gly- or -Tyr-Gly-, and to salts of such compounds having salt-forming groups, to processes for the manufacture thereof, to pharmaceutical preparations containing these compounds and the use of these compounds as medicaments or for the manufacture of pharmaceutical preparations, and also to intermediates.

In the description of the present invention the term "lower" used in the definition of groups or radicals, for example lower alkyl, lower alkoxy, lower alkanoyl, etc., denotes that those groups or radicals, unless expressly defined otherwise, contain up to and including 7, and preferably up to and including 4, carbon atoms.

The carbon atoms substituted by $R_3$, $R_4$ and $R_5$ may have the R-, S- or R,S-configuration. Compounds of the formula I in which these carbon atoms have the S-configuration are preferred.

The general terms and expressions used in the description of the present invention preferably have the following meanings:

Acyl $R_1$ has, for example, up to 19 carbon atoms and is especially the acyl group of a carboxylic acid, of a semi-ester of carbonic acid, of carbamic acid, of an N-substituted carbamic acid, of thiocarbamic acid, of a sulphonic acid, of amidosulphonic acid or of an N-substituted amidosulphonic acid.

Acyl $R_1$ has, for example, the partial formula: $R^b-CO-$, $R^a-O-CO-$, $(R^b)(R^b)N-CO-$, $(R^b)(R^b)N-CS-$, $R^b-SO_2-$ or $(R^b)(R^b)N-SO_2-$ in which $R^a$ represents an unsubstituted or substituted, saturated or unsaturated aliphatic, cycloaliphatic or cycloaliphatic-aliphatic hydrocarbon radical having up to and including 18, preferably up to and including 10, carbon atoms, or an unsubstituted or substituted aromatic, heteroaromatic, aromatic-aliphatic or heteroaromatic-aliphatic hydrocarbon radical having up to and including 18, preferably up to and including 10, carbon atoms, or an unsubstituted or substituted, five- or six-membered heterocycle, and $R^b$ represents hydrogen or has the meanings of $R^a$.

An unsubstituted or substituted, saturated or unsaturated aliphatic, cycloaliphatic or cycloaliphatic-aliphatic hydrocarbon radical $R^a$ or $R^b$ is, for example, alkyl, for example lower alkyl, lower alkenyl, lower alkynyl, mono-, bi- or tri-cycloalkyl, monocycloalkenyl, bicycloalkenyl, cycloalkyl-lower alkyl, cycloalkyl-lower alkenyl or cycloalkenyl-lower alkyl.

Lower alkyl $R^a$ or $R^b$ preferably has from 1 to 7 carbon atoms and is, for example, methyl, ethyl, n-propyl, isopropyl, n-butyl or tert.-butyl each of which may be substituted by one or more functional groups, for example hydroxy, etherified hydroxy, for example lower alkoxy, such as methoxy or ethoxy, phenoxy, or hydroxy etherified by a natural sugar that may, if desired, be acetylated or protected as the acetal, for example glucofuranosyl, esterified hydroxy, for example lower alkanoyloxy, such as acetoxy, or halogen, for example chlorine or bromine, hydroxysulphonyloxy, carboxy, esterified carboxy, for example lower alkoxycarbonyl, such as methoxy- or ethoxycarbonyl, amidated carboxy, for example carbamoyl or mono- or di-lower alkylcarbamoyl, such as methyl- or dimethylcarbamoyl, amino, lower alkylamino, for example methylamino, hydroxy-lower alkylamino, for example 2-hydroxyethylamino, di-lower alkylamino, for example dimethylamino, acylamino or N-acyl-N-lower alkylamino in which acyl is a group $R^c-CO-$ or $R^d-O-CO-$ defined hereinbelow, guanidino, mercapto, lower alkylthio, for example methylthio, or by oxo, it being possible for the substituents to be in the 1-position of the lower alkyl radical only if that radical in the partial formula $R^b-CO-$ is bonded to the carbonyl group.

$R^d$ represents lower alkyl having preferably from 1 to 7 carbon atoms, for example methyl, ethyl, n-propyl, isopropyl, n-butyl, tert.-butyl or tert.pentyl, 2-halo-lower alkyl, for example 2-chloro-, 2-bromo-, 2-iodo- or 2,2,2-trichloro-ethyl, or aryllower alkyl, for example unsubstituted or substituted phenyl-lower alkyl in which phenyl may be mono-, di- or tri-substituted by lower alkyl, lower alkoxy, hydroxy, halogen and/or by nitro, for example benzyl, p-methoxybenzyl, diphenylmethyl or trityl. $R^c$ has the meanings of $R^d$ or is lower alkyl substituted by one or more functional groups, for example hydroxy, etherified hydroxy, for example lower alkoxy, such as methoxy or ethoxy, esterified hydroxy, for example lower alkanoyloxy, such as acetoxy or pivaloyloxy, carboxy, esterified carboxy, for example lower alkoxycarbonyl, such as methoxy- or ethoxy-carbonyl, amidated carboxy, for example carbamoyl or mono- or di-lower alkylcarbamoyl, such as methyl- or dimethyl-carbamoyl, amino, lower alkylamino, for example methylamino, hydroxy-lower alkylamino, for example 2-hydroxyethylamino, di-lower alkylamino, for example dimethylamino, acylamino or N-acyl-N-lower alkylamino in which acyl is a group $R^d-CO-$ or $R^d-O-CO-$, guanidino, mercapto or by lower alkylthio, for example methylthio, or also by phenyl, p-hydroxyphenyl, indolyl or imidazolyl.

Alkyl $R^a$ or $R^b$ preferably has from 1 to 10 carbon atoms and is, for example, lower alkyl having the meanings mentioned above, for example methyl, ethyl, n-pentyl, neopentyl, n-hexyl or n-heptyl, or n-octyl, n-nonyl or n-decyl, and may be substituted by one or more of the functional groups mentioned above.

Substituted lower alkyl or alkyl $R^a$ or $R^b$ is, for example, hydroxy-lower alkyl, for example 2-hydroxyethyl, lower alkoxy-lower alkyl, for example lower alkoxymethyl or lower alkoxyethyl, such as methoxymethyl or 2-methoxyethyl, mono- or di-isopropylideneglucofuranosyl-0-methyl, lower alkanoyloxy-lower alkyl, for example lower alkanoyloxymethyl or lower alkanoyloxyethyl, for example acetoxymethyl or 2-acetoxyethyl, halo-lower alkyl, for example halomethyl or haloethyl, such as 2-chloro- or 2-bromo-ethyl, hydroxysulphonyloxy-lower alkyl, for example hydroxysulphonyloxymethyl or 2-hydroxysulphonyloxyethyl, carboxy-lower alkyl, for example carboxymethyl or 2-carboxyethyl, lower alkoxycarbonyl-lower alkyl, for example lower alkoxycarbonylmethyl or lower alkoxycarbonylethyl, such as methoxycarbonylmethyl or 2-methoxycarbonylethyl, ethoxycarbonylmethyl or 2-ethoxycarbonylethyl, carbamoyl-lower alkyl, for example carbamoylmethyl or 2-carbamoylethyl, lower alkylcarbamoyl-lower alkyl, for example methylcarbamoylmethyl, di-lower alkylcarbamoyl-lower alkyl, for example dimethylcarbamoylmethyl, aminoalkyl, for example aminomethyl, 1-aminoethyl, 3-aminopropyl or 7-aminoheptyl, lower alkylamino-lower alkyl, for example methylaminomethyl, di-lower alkylamino-lower alkyl, for example dimethylaminomethyl, acylaminoalkyl, for example lower alkanoylaminoalkyl, such as acetylaminomethyl, 1-acetylaminoethyl or pivaloylaminomethyl, lower alkoxycarbonylaminoalkyl, such as tert.-butoxycarbonylaminomethyl, 3-tert.-butoxycarbonylaminopropyl or 7-tert.-butoxycarbonylaminoheptyl, aryl-lower alkoxycarbonylaminoalkyl, such as benzyloxycarbonylaminomethyl, 3-benzyloxycarbonylaminopropyl or 7-benzyloxycarbonylaminoheptyl, substituted lower alkanoylamino-lower alkyl, such as γ-aminobutyrylaminomethyl, γ-benzyloxycarbonylaminobutyrylaminomethyl, α-amino-δ-guanidinovalerylaminomethyl or α-benzyloxycarbonylamino-δ-guanidinovalerylaminomethyl, also mercapto-lower alkyl, for example 2-mercaptoethyl, lower alkylthio-lower alkyl, for example 2-methylthioethyl, or oxo-lower alkyl, for example 2-oxopropyl or 2-oxobutyl.

Substituted lower alkyl $R^a$ or $R^b$ having two or more substituents is, for example, hydroxy-carboxylower alkyl, for example hydroxy-carboxy-methyl or 1-hydroxy-2-carboxy-ethyl, hydroxy-lower alkoxycarbonyllower alkyl, for example hydroxy-ethoxy- or -methoxycarbonyl-ethyl, esterified hydroxy-lower alkoxycarbonyl-lower alkyl, for example acetoxy-methoxycarbonyl-methyl, dihydroxy-carboxy-lower alkyl, for example 1,2-dihydroxy-2-carboxy-ethyl, dihydroxy-lower alkoxycarbonyl-lower alkyl, for example 1,2-dihydroxy-2-ethoxy- or -methoxy-carbonyl-ethyl, esterified dihydroxy-lower alkoxycarbonyl-lower alkyl, for example 1,2-diacetoxy-2-ethoxy- or -methoxy-carbonyl-ethyl, hydroxy-amino-lower alkyl, for example 2-hydroxy-1-amino-ethyl, 2-hydroxy-1-amino-propyl or 2-hydroxy-3-amino-5-methylhexyl, hydroxyacylamino-lower alkyl, for example 2-hydroxy-1-benzyloxycarbonylamino-5-methylhexyl, carboxy-aminolower alkyl, for example carboxy-amino-methyl, 2-carboxy-1-amino-ethyl or 3-carboxy-1-amino-propyl, lower alkoxycarbonylamino-lower alkyl, for example methoxy- or ethoxycarbonyl-amino-methyl, carboxyacylamino-lower alkyl, for example 2-carboxy-1-benzyloxycarbonylamino-ethyl or 3-carboxy-1-benzyloxycarbonylamino-propyl, lower alkoxycarbonylacylamino-lower alkyl, for example methoxy- or ethoxy-carbonyl-benzyloxycarbonylaminomethyl or methoxy- or ethoxy-carbonyl-tert.-butoxycarbonylamino-methyl, diamino-lower alkyl, for example 1,5-diaminopentyl, or diacylamino-lower alkyl, for example 1,5-bis(benzyloxycarbonylamino)pentyl.

Lower alkenyl $R^a$ or $R^b$ contains, for example, from 2 to 7, especially from 2 to 4, carbon atoms and is, for example, vinyl, allyl or 2- or 3-butenyl. Lower alkenyl $R^a$ or $R^b$ may be substituted by the same substituents as may lower alkyl.

Lower alkynyl $R^a$ or $R^b$ contains, for example, from 2 to 7, especially from 2 to 4, carbon atoms and is, for example, ethynyl, 1-propynyl or 2-propynyl.

Cycloalkyl $R^a$ or $R^b$ contains, for example, from 3 to 8, especially from 3 to 6, carbon atoms and is, for example, cyclopropyl, cyclobutyl, cyclopentyl or cyclohexyl.

Bicycloalkyl $R^a$ or $R^b$ contains, for example, from 5 to 10, especially from 6 to 9, carbon atoms and is, for example, bicyclo-hexyl, -heptyl, -octyl, -nonyl or -decyl, for example bicyclo[3.1.0]hex-1-, -2- or -3-yl, bicyclo[4.1.0]hept-1- or -4-yl, bicyclo[2.2.1]hept-2-yl, for example endo- or exo-norbornyl, bicyclo[3.2.1]oct-2-yl, bicy2clo[3.3.0]oct-3-yl or bicyclo[3.3.1]non-9-yl.

Tricycloalkyl $R^a$ or $R^b$ contains, for example, from 8 to 10 carbon atoms and is, for example, tricyclo[5.2.1.0$^{2,6}$]dec-8-yl or adamantyl.

Monocycloalkenyl $R^a$ or $R^b$ contains, for example, from 3 to 8, especially from 3 to 6, carbon atoms and is, for example, cyclohexenyl, for example 1-cyclohexenyl, or cyclohexadienyl, for example 1,4-cyclohexadienyl.

Bicycloalkenyl $R^a$ or $R^b$ contains, for example, from 5 to 10, especially from 7 to 10, carbon atoms and is, for example, bicyclo[2.2.1]hept-5-en-yl, for example 5-norbornen-2-yl, bicyclo[2.2.2]octen-2-yl or hexahydro-4,7-methanoind-1-en-6-yl.

Cycloalkyl-lower alkyl $R^a$ or $R^b$ contains, for example, from 4 to 10, especially from 4 to 7, carbon atoms and is, for example, cyclopropylmethyl, cyclobutylmethyl, cyclopentylmethyl or cyclohexylmethyl.

Cycloalkyl-lower alkenyl $R^a$ or $R^b$ contains, for example, from 5 to 10, especially from 5 to 9, carbon atoms and is, for example, cyclohexylvinyl or cyclohexylallyl.

Cycloalkenyl-lower alkyl $R^a$ or $R^b$ contains, for example, from 4 to 10, especially from 4 to 7, carbon atoms and is, for example, 1-cyclohexenylmethyl or 1,4-cyclohexadienylmethyl.

The cycloaliphatic or cycloaliphatic-aliphatic radicals mentioned may be substituted by the same substituents as may lower alkyl $R^a$.

Substituted cycloalkyl $R^a$ or $R^b$ is, for example, hydroxycycloalkyl, for example 4-hydroxycyclohexyl or 3,4,5-trihydroxycyclohexyl, carboxycycloalkyl, for example 4-carboxycyclohexyl, aminocycloalkyl, for example 1-aminocyclopropyl or 4-aminocyclohexyl, or acylaminocycloalkyl, for example 1-tert.-butoxycarbonylaminocyclopropyl or 1-benzyloxycarbonylaminocyclopropyl.

Substituted cycloalkenyl $R^a$ or $R^b$ is, for example, hydroxycycloalkenyl, for example 3,4,5-trihydroxycyclohex-1-enyl.

An aromatic or aromatic-aliphatic hydrocarbon radical $R^a$ or $R^b$ is, for example, unsubstituted or substituted phenyl or phenyl-lower alkyl, respectively, for example halophenyl, such as 4-chlorophenyl, lower alkoxyphenyl, such as 4-methoxyphenyl, or nitrophenyl, benzyl, lower alkylbenzyl, such as 4-methylbenzyl, lower alkoxybenzyl, such as 4-methoxybenzyl, substituted anilinobenzyl, such as 2-(o,o-dichloroanilino)-benzyl or 2-(o,o-dichloro-N-benzylanilino)-benzyl, 2-phenylethyl, 2-(p-hydroxyphenyl)-ethyl, diphenylmethyl, di-(4-methoxyphenyl)-methyl or trityl, or phenyl-lower alkenyl, for example 3-phenylallyl.

In a heteroaromatic or heteroaromatic-aliphatic hydrocarbon radical $R^a$ or $R^b$, the heterocycle is five-or six-membered and contains one/or two nitrogen atoms and/or an oxygen or a sulphur atom and is linked by one of its ring carbon atoms to the group —CO— or —O—CO—,

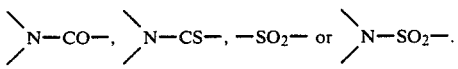

This heterocycle may be benzo-annellated and or substituted at a nitrogen atom by lower alkyl, for example methyl or ethyl, phenyl, or phenyl-lower alkyl, for example benzyl, and is, for example, 2- or 3-pyrrolyl, 2-furanyl, 2-thiophenyl, 4-imidazolyl, 2-, 3- or 4-pyridyl, 3-indolyl, 2-, 3- or 4-quinolinyl, 1-, 3- or 4-isoquinolinyl, 2-benzoxazolyl or 2-benzthiazolyl.

The aromatic-aliphatic or heteroaromatic-aliphatic radicals may be substituted in the aliphatic moiety by the same substituents as may lower alkyl $R^a$.

Substituted phenyl-lower alkyl $R^a$ or $R^b$ is, for example phenyl-hydroxy-lower alkyl, for example α-hydroxybenzyl, substituted or unsubstituted phenylamino-lower alkyl, for example 2-phenyl-1-aminoethyl or 2-(p-hydroxyphenyl)-1-amino-ethyl, or substituted or unsubstituted phenyl-acylamino-lower alkyl, for example 2-phenyl-1-benzyloxycarbonylamino-ethyl or 2-(p-acetoxyphenyl)-1-benzyloxycarbonylamino-ethyl.

A five- or six-membered heterocycle $R^a$ or $R^b$ has as ring members at least one carbon atom, from 1 to 3 nitrogen atoms and optionally an oxygen or a sulphur atom and is linked by one of its ring carbon atoms to the group —CO— or —OCO—,

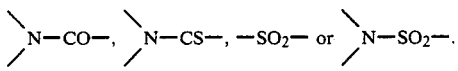

This heterocycle may be substituted at one of its carbon atoms or at a ring nitrogen atom by lower alkyl, for example methyl or ethyl, phenyl or phenyl-lower alkyl, for example benzyl, at one of its carbon atoms by hydroxy or oxo, or at a ring nitrogen atom by acyl $R^d$—CO— or $R^d$—O—CO—.

Such a heterocycle is, for example, pyrrolidin-3-yl, hydroxypyrrolidin-2- or -3-yl, for example 4-hydroxypyrrolidin-2-yl, hydroxy-1-acylpyrrolidin-2- or -3-yl, for example 1-benzyloxycarbonyl-4-hydroxypyrrolidin-2-yl, oxopyrrolidin-2-yl, for example 5-oxopyrrolidin-2-yl, piperidin-2- or -3-yl, 1-lower alkylpiperidin-2-, -3- or -4-yl, for example 1-methylpiperidin2-, -3- or -4-yl, 1-acylpiperidin-2-, -3- or -4-yl, for example 1-benzyloxycarbonylpiperidin-2-, -3- or -4-yl, morpholin-2- or -3-yl, thiomorpholin-2- or -3-yl or 1-and/or 4-lower alkylpiperazin-2- or -3-yl, for example 1,4-dimethylpiperazin-2- or -3-yl. Excluded as heterocycle $R^b$ in an acyl radical $R^b$—CO— is optionally N-acylated pyrrolidin-2-yl, i.e. the residue of the amino acid proline.

Preferred acyl groups $R_1$ are, for example, lower alkanoyl, for example formyl, acetyl, propionyl or pivaloyl, lower alkoxy-lower alkanoyl, for example methoxyacetyl, mono- or di-isopropylidene-glucofuranosyl-O-acetyl, for example 1,2-mono- or 1,2:5,6-di-isopropylidene-glucofuranosyl-3-0-acetyl, halo-lower alkanoyl, for example α-haloacetyl, for example α-chloro, α-bromo-, α-iodo- or α,α,α-trichloro-acetyl, carboxy-lower alkanoyl, for example carboxyacetyl, lower alkoxycarbonyl-lower alkanoyl, for example methoxycarbonylacetyl, aminoalkanoyl, for example amino-acetyl, γ-aminopropionyl, γ-aminobutyryl or 8-aminooctanoyl, acylaminoalkanoyl, for example acetylaminoacetyl, pivaloylaminoacetyl, tert.-butoxycarbonylaminoacetyl, γ-(tert.-butoxycarbonylamino)-butyryl, 8-(tert.-butoxycarbonylamino)-octanoyl, benzyloxycarbonylaminoacetyl, γ-(benzyloxycarbonylamino)-butyryl, 8-(benzyloxycarbonylamino)-octanoyl, γ-aminobutyrylaminoacetyl, γ-benzyloxycarbonylaminobutyryl-aminoacetyl, (α-amino-δ-guanidinovaleryl)-aminoacetyl, or (α-benzyloxycarbonylamino-δ-guanidinovaleryl)-aminoacetyl, oxo-lower alkanoyl, for example acetoacetyl, hydroxy-carboxy-lower alkanoyl, for example α-hydroxyβ-carboxypropionyl, hydroxy-lower alkoxycarbonyl-lower alkanoyl, for example α-hydroxy-β-ethoxy- or -methoxycarbonylpropionyl, dihydroxy-carboxy-lower alkanoyl, for example α,β-dihydroxy-β-carboxypropionyl, dihydroxylower alkoxycarbonyl-lower alkanoyl, for example α,β-dihydroxy-β-ethoxy- or -methoxy-carbonylpropionyl, esterified dihydroxy-lower alkoxycarbonyl-lower alkanoyl, for example α,β-diacetoxy-β-methoxycarbonylpropionyl, hydroxy-amino-lower alkanoyl, for example β-hydroxy-α-aminopropionyl or 3-hydroxy-4-amino-6-methylheptanoyl, hydroxyacylamino-lower alkanoyl, for example β-hydroxy-a-benzyloxycarbonylaminopropionyl or 3-hydroxy-4-benzyloxycarbonylamino-6-methylheptanoyl, carboxyamino-lower alkanoyl, for example α-carboxy-α-aminoacetyl, lower alkoxycarbonyl-amino-lower alkanoyl, for example α-methoxy- or ethoxy-carbonyl-α-aminoacetyl, lower alkoxycarbonyl-acylamino-lower alkanoyl, for example α-methoxy- or ethoxy-carbonyl-α-benzyloxycarbonylaminoacetyl, lower alkenoyl, for example acryloyl or crotonoyl, lower alkynoyl, for example propiolyl, cyclopentyl- or cyclohexyl-carbonyl, hydroxycyclohexylcarbonyl, for example 3,4,5-trihydroxycyclohexylcarbonyl, acylaminocycloalkylcarbonyl, for example 1-tert.-butoxycarbonylaminocyclopropylcarbonyl or 1-benzyloxycarbonylaminocyclopropylcarbonyl, 3,4,5-trihydroxycyclohex-1-enylcarbonyl, benzoyl or benzoyl that is substituted by halogen, for example chlorine, lower alkoxy, for example methoxy, and/or by nitro, for example 4-chloro-, 4-methoxyor 4-nitro-benzoyl, 2-(o,o-dichloroanilino)-phenylacetyl, 2-(o,o-dichloro-N-benzylanilino)phenylacetyl, hydroxypyrrolidinylcarbonyl, for example 3- or 4-hydroxypyrrolidinyl-2-carbonyl, hydroxy-1-acylpyrrolidinylcarbonyl, for example 3- or 4-hydroxy1-benzyloxycarbonylpyrrolidinyl-2-carbonyl, lower alkoxycarbonyl, for example tert.-butoxycarbonyl, 2-halo-lower alkoxycarbonyl, for example 2-chloro-, 2-bromo-, 2-iodo- or 2,2,2-trichloro-ethoxycarbonyl, arylmethoxycarbonyl having one or two aryl radicals in which aryl is phenyl optionally mono-, di- or tri-substituted by lower alkyl, for example methyl or tert.-butyl, lower alkoxy, for example methoxy, hydroxy, halogen, for example chlorine, and/or by nitro, for example benzyloxycarbonyl, 4-nitrobenzyloxycarbonyl, diphenylmethoxycarbonyl or di-(4-methoxyphenyl)-methoxycarbonyl.

The amino acid residues $X_1$ and $X_2$ are bonded to each other by a peptide bond and are derived from the natural amino acids that normally occur in egg whites and that are listed, for example, in Houben-Weyl, Methoden der Organischen Chemie, vol. XV/1 (1974), "Synthese von Peptiden" ("Synthesis of Peptides"), page 2. These amino acids are α-amino acids having the L-configuration and comprise in particular the 20 α-amino acids that occur especially frequently in proteins, namely glycine (H-Gly-OH), alanine (H-Ala-OH), proline (H-Pro-OH), serine (H-Ser-OH), cysteine (H-Cys-OH), tyrosine (H-Tyr-OH), asparagine (H-Asn-OH), glutamine (H-Gln-OH), aspartic acid (H-Asp-OH), glutamic acid (H-Glu-OH), arginine (H-Arg-OH), histidine (H-His-OH), including those 8 amino acids which are essential for humans, namely valine (H-Val-OH), leucine (H-Leu-OH), isoleucine (H-Ile-OH), lysine (H-Lys-OH), phenylalanine (H-Phe-OH), tryptophan (H-Trp-OH), methionine (H-Met-OH) and threonine (H-Thr-OH), and also trans-3- and trans-4-hydroxyproline, α-aminobutyric acid, α,β-diaminopropionic acid, α,γ-diaminobutyric acid, ornithine and δ-hydroxylysine.

In order to increase the stability of the compounds of the formula I towards enzymatic degradation, the amino acid residues $X_1$ and $X_2$ may be substituted N-terminally by lower alkyl, for example methyl or ethyl.

A carboxy function in the side chain of an amino acid residue $X_1$ and $X_2$, as occurs in glutamic acid and aspartic acid, may, if desired, be esterified by a lower alkanol, for example by methanol or tert.-butanol. An amino function in the side chain of an amino acid residue $X_1$ and $X_2$, as occurs in lysine, α,β-diaminopropionic acid, αγ-diaminobutyric acid, ornithine and δ-hydroxylysine, may, if desired, be acylated by a radical $R_d$—CO, for example pivaloyl, or $R^d$—O—CO—, for example tert.-butoxycarbonyl or benzyloxycarbonyl.

$X_1$ is preferably the bivalent residue of phenylalanine, histidine, arginine or optionally esterified glutamic acid. Most especially preferred is the bivalent residue of phenylalanine.

$X_2$ is preferably the bivalent residue of histidine, phenylalanine, leucine, alanine or arginine. Most especially preferred is the bivalent residue of histidine or phenylalanine.

Lower alkyl $R_2$, $R_3$ or $R_5$ has the meanings mentioned hereinbefore for lower alkyl $R^a$. Lower alkyl $R_2$ is preferably methyl or ethyl. Alkyl $R_3$ or $R_5$ is preferably lower alkyl, for example isopropyl or isobutyl, or n-octyl.

Cycloalkyl $R_3$ or $R_5$ has the meanings mentioned hereinbefore for cycloalkyl $R^a$ or $R^b$ and is preferably cyclohexyl.

Aryl-lower alkyl $R_3$ or $R_5$ has the meanings mentioned hereinbefore for aryl-lower alkyl $R^a$ or $R^b$ and is preferably benzyl.

Aryl $R_3$ or $R_5$ is preferably phenyl.

An etherified hydroxy group $R_4$ is preferably etherified by organic radicals that can be removed under physiological conditions and that, after removal, produce cleavage products that are pharmacologically harmless in the concentration concerned.

Etherified hydroxy $R_4$ is, for example, acyloxylower alkoxy in which acyl is the acyl group of an optionally branched lower alkanecarboxylic acid or of carbonic acid mono-esterified by optionally branched lower alkyl, for example lower alkanoyloxy-lower alkoxy, such as acetoxymethoxy, 1-acetoxyethoxy, pivaloyloxymethoxy or 1-pivaloyloxyethoxy, or lower alkoxycarbonyloxy-lower alkoxy, such as ethoxycarbonyloxymethoxy, 1-ethoxycarbonyloxyethoxy, tert.-butoxycarbonyloxymethoxy or 1-tert.-butoxycarbonyloxyethoxy.

Etherified hydroxy $R_4$ is also lower alkoxy, for example methoxy or ethoxy, aryloxy, for example phenoxy, or aryl-lower alkoxy, for example benzyloxy.

Esterified hydroxy $R_4$ is, for example, aliphatic acyloxy, for example lower alkanoyloxy, such as acetoxy or pivaloyloxy, cycloaliphatic acyloxy, for example cycloalkanoyloxy, such as cyclohexanoyloxy, or aromatic acyloxy, for example benzoyloxy.

$R_6$ representing "substituted amino" or "substituted hydroxy" is, for example, an amino or hydroxy group substituted by one or optionally two unsubstituted or substituted, saturated or unsaturated aliphatic hydrocarbon radical(s) having up to and including 18, preferably up to and including 10, carbon atoms, or by an unsubstituted or substituted aromatic, heteroaromatic, aromatic-aliphatic or heteroaromatic-aliphatic hydrocarbon radical having up to 18, preferably up to and including 10, carbon atoms.

$R_6$ representing "substituted amino" or "substituted hydroxy" may also be a residue of a natural α-amino acid that is bonded N-terminally to the group —CO— and optionally amidated or esterified C-terminally, or a di- or tri-peptide residue that consists of natural a-amino acids and, if desired, statin (abbreviated: H-Sta-OH, 4-amino-3-hydroxy-6-methylheptanoic acid) and that is bonded N-terminally to the group —CO— and optionally amidated or esterified C-terminally.

An unsubstituted or substituted, saturated or unsaturated aliphatic hydrocarbon radical that substitutes the amino group or hydroxy group $R_6$ is, for example, alkyl having up to 10 carbon atoms, or lower alkenyl or lower alkynyl having up to and including 7 carbon atoms.

These radicals may be substituted like lower alkyl $R^a$ by one or more of the functional groups mentioned hereinbefore, and by sulpho, cyano or substituted amino in which the amino group is part of a five- or six-membered heterocycle containing one or two nitrogen atoms and, if desired, an oxygen or a sulphur atom.

Preferred substituents are hydroxy, substituted or unsubstituted phenoxy, for example carbamoylphenoxy or carbamoyl-hydroxy-phenoxy, carboxy, esterified carboxy, for example lower alkoxycarbonyl, such as tert.-butoxycarbonyl, or a physiologically cleavable esterified carboxy group, for example 1-(lower alkanoyloxy)-lower alkoxycarbonyl, such as acetoxymethoxycarbonyl, pivaloyloxymethoxycarbonyl or 1-propionyloxyethoxycarbonyl, 1-(lower alkoxycarbonyloxy)-lower alkoxycarbonyl, such as 1-(ethoxycarbonyloxy)-ethoxycarbonyl, or α-amino-lower alkanoyloxymethoxycarbonyl, such as α-aminoacetoxymethoxycarbonyl or (S-α-amino8-methylbutyryloxymethoxycarbonyl, carbamoyl, substituted or unsubstituted lower alkylcarbamoyl, for example hydroxy-lower alkylcarbamoyl, such as 2-hydroxyethylcarbamoyl, tri-lower alkylsilyloxy-lower alkylcarbamoyl, or methoxycarbonyl-hydroxy-lower alkylcarbamoyl, amino, substituted or unsubstituted lower alkylamino, for example hydroxy-lower alkylamino, di-lower alkylamino, five- or six-membered, optionally oxo-substituted heterocyclyl bonded by way of a nitrogen atom, for example 1-piperidyl, 4-morpholinyl or 2-oxo-1-pyrrolidinyl, and acylamino, for example lower alkoxycarbonylamino, such as tert.-butoxycarbonylamino.

Alkyl having from 1 to 10 carbon atoms is, for example, lower alkyl having the meanings mentioned under $R^a$, for example methyl or ethyl, and also n-pentyl, neopentyl, n-hexyl, n-heptyl, n-octyl, n-nonyl or n-decyl.

Substituted alkyl is, for example, hydroxy-lower alkyl, for example 2-hydroxyethyl, lower alkoxy-lower alkyl, for example lower alkoxymethyl or lower alkoxyethyl, for example methoxymethyl or 2-methoxyethyl, lower alkanoyloxy-lower alkyl, for example lower alkanoyloxymethyl or lower alkanoyloxyethyl, for example acetoxymethyl or 2-acetoxyethyl, halo-lower alkyl, for example halomethyl or haloethyl, for example trifluoromethyl, chloro- or bromo-methyl, 2-chloro-, 2-bromo or 2,2,2-trichloro-ethyl, hydroxysulphonyloxy-lower alkyl, for example hydroxysulphonyloxymethyl or 2-hydroxysulphonyloxyethyl, phenoxy-lower alkyl, for example 2-phenoxyethyl, substituted phenoxy-lower alkyl, for example 2-(3-carbamoyl-4-hydroxyphenoxy)-ethyl, substituted phenoxy-hydroxy-lower alkyl, for example 3-(3-carbamoylphenoxy)-2-hydroxypropyl, carboxyalkyl, for example 4-carboxy-n-butyl, 5-carboxy-n-pentyl, 6-carboxy -n-hexyl, 7-carboxy-n-heptyl or 8-carboxy-n-octyl, also carboxymethyl, 2-carboxyethyl, 3-carboxyn-propyl or 1- or 2-carboxyprop-2-yl, esterified carboxyalkyl, for example lower alkoxycarbonylalkyl, for example 4-tert.-butoxycarbonyl-n-butyl, 7-tert.-butoxycarbonyl-n-heptyl or 8-tert.-butoxycarbonyl-n-octyl, also tert.-butoxycarbonylmethyl or 2-tert.-butoxycarbonylethyl, or physiologically cleavable esterified carboxyalkyl, for example 7-pivaloyloxymethoxycarbonyln-heptyl, 7-(1-ethoxycarbonyloxyethoxycarbonyl)-n-heptyl or 4-pivaloyloxymethoxycarbonyl-n-butyl, carbamoyl-lower alkyl, for example carbamoylmethyl, 2-carbamoylethyl or dicarbamoylmethyl, lower alkylcarbamoyl-lower alkyl, for example methylcarbamoylmethyl, hydroxy-lower alkylcarbamoyl-lower alkyl, for example 7-(2-hydroxyethyl)-carbamoyl-n-heptyl, 4-(2-hydroxyethyl)-carbamoyl-n-butyl, 7-(tris-[hydroxymethyl]methyl)-carbamoyl-n-heptyl or 4-(tris-[hydroxymethyl]methyl)-carbamoyl-n-butyl, tri-lower alkylsilyloxylower alkylcarbamoyl-lower alkyl, for example 4-(tris-[tert.-butyldimethylsilyloxymethyl]-methyl)-carbamoyln-butyl, lower alkoxycarbonyl-hydroxy-lower alkylcarbamoyl-lower lkyl, for example carbamoyl-(2-hydroxy-1-isobutyl-3-methoxycarbonylpropyl)-carbamoyl-methyl, di-lower alkylcarbamoyl-lower alkyl, for example dimethylcarbamoylmethyl, sulpho-lower alkyl, for example sulphomethyl or 2-sulphoethyl, aminoalkyl, for example 4-amino-n-butyl, 5-amino-n-pentyl, 6-amino-n-hexyl, 7-amino-n-heptyl or 8-amino-n-octyl, also 2-aminoethyl or 3-amino-n-propyl, lower alkylamino-lower alkyl, for example 2-methylaminoethyl or 3-methylamino-n-propyl, hydroxy-lower alkylamino-lower alkyl, for example 2-(2-hydroxyethylamino)-ethyl, di-lower alkylamino-lower alkyl, for example 2-dimethylaminoethyl or 3-dimethylamino-n-propyl, five- or six-membered heterocyclyllower alkyl bonded by way of a nitrogen atom, for example 3-(1-piperidinyl)-propyl, 2-(1-piperidinyl)ethyl, 3-(4-morpholinyl)-propyl, 2-(4-morpholinyl)ethyl, 3-(2-oxo-1-pyrrolidinyl)-propyl or 2-(2-oxo-1-pyrrolidinyl)-ethyl, or acylaminoalkyl, for example lower alkanoylaminoalkyl, for example pivaloylaminoalkyl or acetylaminoalkyl, such as 4-pivaloylamino-n-butyl or 4-acetylamino-n-butyl, or lower alkoxycarbonylaminoalkyl, for example tert.-butoxycarbonylaminoalkyl, such as 4-tert.-butoxycarbonylamino-n-butyl, 5-tert.-butoxycarbonylamino-n-pentyl, 6-tert.-butoxycarbonylamino-n-hexyl or 7-tert.-butoxycarbonylamino-n-heptyl, also 2-tert.-butoxycarbonylaminoethyl.

Lower alkenyl and lower alkynyl are defined in the same manner as the radicals mentioned under $R^a$ and $R^b$ and may be substituted by the same substituents as may lower alkyl $R^a$.

An aromatic or aromatic-aliphatic hydrocarbon radical has the same meanings as those mentioned under $R^a$ or $R^b$ and is preferably phenyl or phenyl-lower alkyl.

These radicals may be substituted in the aromatic moiety, for example by lower alkyl, such as methyl or ethyl, hydroxy, etherified hydroxy, for example lower alkoxy, such as methoxy or tert.-butoxy, esterified hydroxy, for example lower alkanoyloxy, such as acetoxy, or halogen, for example fluorine or chlorine, carboxy, esterified carboxy, for example lower alkoxycarbonyl, such as tert.-butoxycarbonyl, carbamoyl, amino, lower alkylamino, for example methylamino, di-lower alkylamino, for example dimethylamino, acylated amino, for example lower alkoxycarbonylamino, such as tert.-butoxycarbonylamino, or also by nitro.

Lower alkyl in a phenyl-lower alkyl radical may be substituted by the same substituents as may alkyl in a radical $R_6$.

Substituted phenyl is, for example, 2-, 3- or 4-lower alkylphenyl, for example 2-, 3- or 4-methylphenyl, 2-, 3- or 4-hydroxyphenyl, 2-, 3- or 4-lower alkoxyphenyl, for example 2-, 3- or 4-methoxyphenyl, 2,3-, 2,4- or 2,5-dimethoxyphenyl or 2-, 3- or 4-tert.-butoxyphenyl, 2-, 3- or 4-halophenyl, for exmple 2-, 3-or 4-chlorophenyl, 2,3-, 3,4- or 2,5-dihalophenyl, for example 2,3-, 3,4- or 2,5-dichlorophenyl, 2-, 3- or 4-carboxyphenyl, 2-, 3- or 4-lower alkoxycarbonylphenyl, for example 2-, 3- or 4-tert.-butoxycarbonylphenyl, 2-, 3- or 4-carbamoylphenyl, 2-, 3- or 4-aminophenyl, 2-, 3-or 4-lower alkoxycarbonylaminophenyl, for example 2-, 3-or 4-tert.-butoxycarbonylaminophenyl, or 2-, 3- or 4-nitrophenyl.

Substituted or unsubstituted phenyl-lower alkyl is, for example, benzyl, 2-phenylethyl, 1-phenylprop-2-yl, 3-phenylpropyl, or 1-hydroxymethyl-2-phenylethyl, 2-hydroxy-1- or -2-phenylethyl or 1-(2-cyano- or 2-carboxy-1-hydroxyethyl)-2-phenylethyl.

A heteroaromatic or heteroaromatic-aliphatic hydrocarbon radical has the same meanings as those mentioned under $R^a$ and $R^b$ and is preferably oxazolyl, thiazolyl, pyridyl-lower alkyl, imidazolyl-lower alkyl or indolyl-lower alkyl.

These radicals may be substituted in the heteroaromatic moiety, for example by lower alkyl, for example methyl or ethyl, carboxy, esterified carboxy, for example lower alkoxycarbonyl, such as tert.-butoxycarbonyl, carbamoyl, carboxy-lower alkyl, for example carboxymethyl, esterified carboxy-lower alkyl, for example lower alkoxycarbonyl, such as methoxycarbonylmethyl, or carbamoyl-lower alkyl, for example carbamoylmethyl.

Substituted or unsubstituted heteroaryl is, for example, 2-oxazolyl, 2-thiazolyl or 4- or 5-carbamoylmethyl-2-thiazolyl.

Substituted or unsubstituted heteroaryl-lower alkyl is, for example, 2-, 3- or 4-pyridylmethyl, 2-(2-, 3- or 4-pyridyl)-ethyl, 3-(2-, 3- or 4-pyridyl)-propyl, 4- imidazolylmethyl, 2-(4-imidazolyl)-ethyl, 3-indolylmethyl or 2-(3-indolyl)-ethyl.

The amino or hydroxy group $R_6$ may also be substituted by a five- or six-membered heterocycle having the meanings mentioned under $R^a$ or $R^b$. Such a heterocycle is, for example, 1-benzylpiperidin-2-, -3- or -4-yl, or 1-lower alkoxycarbonylpiperidinyl, for example 1-ethoxy- or 1-n-butoxy-carbonylpiperidin-2-, -3- or -4-yl.

Substituted amino $R_6$ is preferably alkylamino, for example methyl-, ethyl-, n-propyl, n-butyl-, isobutyl-, tert.-butyl-, n-pentyl-, n-hexyl-, n-octyl- or n-decylamino, di-lower alkylamino, for example dimethylamino, hydroxy-lower alkylamino, for example 2-hydroxyethylamino or tris(hydroxymethyl)-methylamino, lower alkoxy-lower alkylamino, for example 2-methoxyethylamino, substituted phenoxy-lower alkylamino, for example 2-(3-carbamoyl-4-hydroxyphenoxy)-ethylamino, substituted phenoxy-hydroxy-lower alkylamino, for example 3-(3-carbamoylphenoxy)-2-hydroxypropylamino, carboxyalkylamino, for example 4-carboxy-n-butylamino, 5-carboxy-n-pentylamino, 6-carboxy-n-hexylamino, 7-carboxy-n-heptylamino, 8-carboxy-n-octylamino or 1-carboxyprop-2-ylamino, lower alkoxycarbonylalkylamino, for example 4-tert.-butoxycarbonyl-n-butylamino, 7-tert.-butoxycarbonyl-n-heptylamino or 8-tert.-butoxycarbonyl-n-octylamino, physiologically cleavable esterified carboxyalkylamino, for example 4-pivaloyloxymethoxyethoxycarbonyl-n-butylamino, 7-(1-ethoxycarbonyloxyethoxycarbonyl)-n-heptylamino or 7-pivaloyloxymethoxycarbonyl-n-heptylamino, carbamoyl-lower alkylamino, for example carbamoylmethylamino or dicarbamoylmethylamino, hydroxy-lower alkylcarbamoyl-lower alkylamino, for example 4-(tris[hydroxymethyl]-methyl)-carbamoyl-n-butylamino, lower alkoxycarbonyl-hydroxy-lower alkylcarbamoyl-lower alkylamino, for example α-carbamoyl-α-(2-hydroxy-1-isobutyl-3-methoxycarbonylpropyl)-carbamoylmethylamino, aminoalkylamino, for example 4-amino-n-butylamino, 5-amino-n-pentylamino, 6-amino-n-hexylamino, 7-amino-n-heptylamino or 8-amino-n-octylamino, hydroxy-lower alkylamino-lower alkylamino, for example 2-(2-hydroxyethylamino)-ethylamino, di-lower alkylamino-lower alkylamino, for example 2-dimethylaminoethylamino, five- or six-membered heterocyclyllower alkylamino bonded by way of a nitrogen atom, for example 3-(4-morpholinyl)-propylamino or 3-(2-oxo-1-pyrrolidinyl)-propylamino, acylamino-lower alkylamino, for example lower alkanoylamino-lower alkylamino, such as 4-pivaloylamino-n-butylamino, or lower alkoxycarbonylamino-lower alkylamino, such as 4-tert.-butoxycarbonylamino-n-butylamino, 5-tert.-butoxycarbonylamino-n-pentylamino, 6-tert.-butoxycarbonylamino-n-hexylamino or 7-tert.-butoxycarbonylamino-n-heptylamino or 8-tert.-butoxycarbonylamino-n-octylamino, benzylamino, carboxybenzylamino, for example 3-carboxybenzylamino, and lower alkoxycarbonylbenzylamino, for example 3-tert.-butoxycarbonylbenzylamino.

Substituted hydroxy $R_6$ is preferably lower alkoxy, for example methoxy, ethoxy, n-propoxy, isopropoxy, butoxy, isobutoxy, tert.-butoxy or tert.-pentoxy, or physiologically cleavable alkoxy, for example pivaloyloxymethoxy.

A natural amino acid residue $R_6$ that is bonded N-terminally to the —CO— group and optionally amidated or esterified C-terminally preferably consists of one of the 20 α-amino acids mentioned hereinbefore that occur especially frequently in proteins, for example -His-, -Phe- and especially -Ala- or -Ile-, and is optionally substituted C-terminally by amino, substituted amino or by substituted hydroxy. Such substituted amino or substituted hydroxy has the meanings mentioned hereinbefore for $R_6$ and is, for example, alkylamino, for example methyl-, ethyl-, n-propyl-, n-butyl- or n-octyl-amino, di-lower alkylamino, for example dimethylamino, hydroxy-lower alkylamino, for example 2-hydroxyethylamino or tris(hydroxymethyl)-methylamino, carboxyalkylamino, for example 4-carboxy-n-butylamino or 1-carboxyprop-2-yl-amino, lower alkoxycarbonylalkylamino, for example 4-tert.-butoxycarbonyl-n-butylamino or 7-tert.-butoxycarbonyl-n-heptylamino, physiologically cleavable, esterified carboxyalkylamino, for example 4-pivaloyloxymethoxycarbonyl-n-butylamino, carbamoyl-lower alkyl-amino, for example carbamoylmethylamino or dicarbamoylmethylamino, hydroxy-lower alkylcarbamoyl-lower alkylamino, for example 2-hydroxyethylcarbamoyl-methylamino or di-(2-hydroxyethylcarbamoyl)-methylamino, aminoalkylamino, for example 4-amino-n-butylamino, 5-amino-n-pentylamino or 8-amino-n-octylamino, hydroxy-lower alkylamino-lower alkylamino, for example 2-(2-hydroxyethylamino)-ethylamino, di-lower alkylamino-lower alkylamino, for exmple 2-dimethylaminoethylamino, five- or six-membered heterocyclyl-lower alkylamino bonded by way of a nitrogen atom, for example 3-(4-morpholinyl)-propylamino, 2-(4-morpholinyl)-ethylamino or 3-(2-oxo-1-pyrrolidinyl)-propylamino, acylamino-lower alkylamino, for example lower alkoxycarbonylamino-lower alkylamino, such as 4-tert.-butoxycarbonylamino-n-butylamino, phenyl-lower alkylamino, for example benzylamino, carboxybenzylamino, for example 3-carboxybenzylamino, lower alkoxycarbonylbenzylamino, for example 3-tert.-butoxycarbonylbenzylamino, carbamoylbenzylamino, for example 3-carbamoylbenzylamino, 2-phenylethylamino, 1-phenylprop-2-ylamino, 3-phenylpropylamino, 1-hydroxymethyl-2-phenylethylamino, 2-hydroxy-1- or -2-phenylethylamino, 1-(2-cyano- or 2-carboxy-1-hydroxyethyl)-2-phenylethylamino, thiazolylamino, for example 2-thiazolylamino or 4- or 5-carbamoylmethyl-2-thiazolylamino, pyridyl-lower alkylamino, for example 2-, 3- or 4-pyridylmethylamino, 2-(2-, 3- or 4-pyridyl)-ethylamino, 3-(2-, 3- or 4-pyridyl)-propylamino, imidazolyllower alkylamino, for example 4-imidazolylmethylamino, 2-(4-imidazolyl)-ethylamino, indolyl-lower alkylamino, for example 3-indolylmethylamino, 2-(3-indolyl)-ethylamino, piperidinylamino, for example 1-benzylpiperidin-2-, -3- or -4-ylamino, 1-lower alkoxycarbonylpiperidinylamino, for example 1-ethoxy- or 1-n-butoxy-carbonylpiperidin-2-, -3- or -4-ylamino, and also lower alkoxy, for example methoxy, ethoxy or tert.-butoxy, or physiologically cleavable substituted alkoxy, for example pivaloyloxymethoxy.

In a di- or tri-peptide residue that is bonded N-terminally to the —CO— group and optionally amidated or esterified C-terminally, the amino acid components are preferably derived from the 20 α-amino acids mentioned hereinbefore that occur especially frequently in proteins and from statin. Such a di- or tri-peptide residue is, for example, -Ile-His-, -Ile-Phe-, -Ala-His-, -Gly-Gly-, -Gly-His-, -Gly-Ala-, -Gly-Ser-, -Ala-Sta-, -Ile-Sta-, -Gly-Gly-Gly-, -Gly-His-Lys-, -Gly-Ala-Gly- or -Ile-His-Lys.

In order to increase the stability of the compound of the formula I towards enzymatic degradation, the amino acid residues may be substituted N-terminally by lower alkyl, for example methyl or ethyl. The carboxy function in the side chain of -Glu- and -Asp- may, if desired, be esterified by a lower alkanol, for example methanol or tert.-butanol. The amino function in the side chain of -Lys- may, if desired, be acylated by a radical $R^d$—CO—, for example pivaloyl, or by a radical $R^d$—O—CO—, for example tert.-butoxycarbonyl or benzyloxycarbonyl.

A di- or tri-peptide residue is optionally substituted C-terminally by amino, substituted amino or by substituted hydroxy. Such substituted amino or substituted hydroxy has the meanings mentioned hereinbefore for $R_6$ and is, for example, lower alkylamino, for example methyl-, ethyl- n-propyl- or n-butyl-amino, di-lower alkylamino, for example dimethylamino, hydroxy-lower alkylamino, for example 2-hydroxyethylamino or tris-(hydroxymethyl)-methylamino, or also lower alkoxy, for example methoxy, ethoxy or tert.-butoxy, or physiologically cleavable substituted alkoxy, for example pivaloyloxymethoxy.

Salts are especially the pharmaceutically acceptable or non-toxic salts of compounds of the formula I.

Such salts are formed, for example, by compounds of the formula I having an acidic group, for example a carboxy group, and are, especially, suitable alkali metal salts, such as sodium or potassium salts, or suitable alkaline earth metal salts, for example magnesium or calcium salts, and also zinc salts or ammonium salts, including those salts which are formed with organic amines, such as optionally hydroxy-substituted mono-, di- or tri-lower alkylamines, for example diethylamine, di-(2-hydroxyethyl)-amine, triethylamine, N,N-dimethyl-N-(2-hydroxyethyl)-amine, tri-(2-hydroxyethyl)-amine or N-methyl-D-glucamine. The compounds of the formula I having a basic group, for example an amino group, can form acid addition salts, for example with inorganic acids, for example hydrochloric acid, sulphuric acid or phosphoric acid, or with organic carboxylic, sulphonic or sulpho acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and amino acids, such as, for example, the α-amino acids mentioned hereinbefore, and also methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid, or with other acidic organic compounds, such as ascorbic acid. Compounds of the formula I having acidic and basic groups can also form internal salts.

For the purposes of isolation or purification it is also possible to use pharmaceutically unsuitable salts.

The compounds of the present invention exhibit enzyme-inhibiting actions; in particular, they inhibit the action of the natural enzyme renin. The latter passes from the kidneys into the blood and there brings about the cleavage of angiotensinogen to form the decapeptide angiotensin I which is then cleaved in the lungs, the kidneys and other organs to form the octapeptide angiotensin II. The latter raises the blood pressure both directly through arterial constriction and indirectly through releasing from the adrenal gland the hormone aldosterone which retains sodium ions, which involves an increase in the extracellular fluid volume. This increase is to be attributed to the action of angiotensin II itself or of the heptapeptide angiotensin III formed therefrom as a cleavage product. Inhibitors of the enzymatic activity of renin bring about a reduction in the formation of angiotensin I. As a consequence of this, less angiotensin II is produced. The reduced concentration of this active peptide hormone is the direct cause of the blood pressure-reducing action of renin-inhibitors.

The action of renin-inhibitors is demonstrated experimentally inter alia by means of in vitro tests, the reduction in the formation of angiotensin I being measured in various systems (human plasma, purified human renin together with synthetic or natural renin substrate). The following in vitro test inter alia is used: An extract of human renin from the kidney (0.5 mGU [milli Goldblatt units]/ml) is incubated for one hour at 37° C. and pH 7.2 in 1 molar aqueous 2-N-(trishydroxymethyl-methyl)-amino-ethanesulphonic acid-buffer solution with 23 μg/ml of synthetic renin substrate, the tetradecapeptide H-Asp-Arg-Val-Tyr-Ile-His-Pro-Phe-His-Leu-Leu-Val-Tyr-Ser-OH. The amount of angiotensin I formed is determined by a radioimmunoassay. The inhibiting substances according to the invention are each added to the incubation mixture in different concentrations. $IC_{50}$ denotes that concentration of the particular inhibiting substance which reduces the formation of angiotensin I by 50%. In the in vitro systems, the compounds of the present invention exhibit inhibiting actions at minimum concentrations of from approximately $10^{-6}$ to approximately $10^{-9}$ mol/liter.

In animals depleted of salt the renin-inhibitors bring about a fall in blood pressure. Human renin differs from renin of other species. For testing inhibitors of human renin primates (marmosets, *Callithrix jacchus*) are used since human renin and primate renin are to a great extent homologous in the enzymatically active range. The following in vivo test inter alia is used: The test compounds are tested in conscious normotensive marmosets of both sexes having a body weight of approximately 300 g. Blood pressure and heart rate are measured by means of a catheter in the femoral artery. The endogenous release of renin is stimulated by intravenous injection of furosemide (5 mg/kg). 30 minutes after the injection of furosemide, the test substances are administered via a catheter in the lateral caudal vein either by a single injection or by continuous infusion and their effect on the blood pressure and heart rate is evaluated. The compounds of the present invention are effective in the described in vivo test in dosages of from approximately 0.1 to approximately 1.0 mg/kg i.v..

The compounds of the present invention can be used as antihypertensives and also for the treatment of cardiac insufficiency.

The invention relates especially to compounds of the formula I in which $R_1$ represents hydrogen or acyl having the partial formula $R^b$—CO— or $R^a$—O—CO— in which $R^a$ represents an unsubstituted or substituted, saturated or unsaturated aliphatic, cycloaliphatic or cycloaliphatic-aliphatic hydrocarbon radical having up to and including 18, preferably up to and including 10, carbon atoms, or an unsubstituted or substituted aromatic, heteroaromatic, aromatic-aliphatic or heteroaromatic-aliphatic hydrocarbon radical having up to and including 18, preferably up to and including 10, carbon atoms, or an unsubstituted or substituted, five- or six-membered heterocycle, and $R^b$ represents hydrogen or has the meanings of $R^a$, $X_1$ represents a natural amino acid residue that is bonded N-terminally to $R_1$ and C-terminally to $X_2$, $X_2$ represents an optionally N-alkylated natural amino acid residue bonded N-terminally to $X_1$ and C-terminally to the group $-NR_2-$, $R_2$ represents hydrogen or lower alkyl, $R_3$ represents hydrogen, lower alkyl, cycloalkyl, aryl-lower alkyl or aryl, $R_4$ represents hydroxy, $R_5$ represents alkyl, cycloalkyl, aryl-lower alkyl or aryl, and $R_6$ represents amino or an amino or hydroxy group that is substituted by one or optionally two unsubstituted or substituted, saturated or unsaturated aliphatic hydrocarbon radical(s) having up to and including 18, preferably up to and including 10, carbon atoms, or by an aromatic, heteroaromatic, aromatic-aliphatic or heteroaromatic-aliphatic hydrocarbon radical having up to and including 18, preferably up to and including 10, carbon atoms, or a natural $\alpha$-amino acid residue that is bonded N-terminally to the group $-CO-$ and optionally amidated or esterified C-terminally, or a di- or tri-peptide residue that consists of natural $\alpha$-amino acids and, if desired, statin and is bonded N-terminally to the group $-CO-$ and optionally amidated or esterified C-terminally, with the exception of compounds in which $R_1$ represents an optionally N-acylated residue of the amino acid L-proline or in which $X_1$ and $X_2$ together represent -Val-Val-, -Gly-Gly- or -Tyr-Gly-, and to pharmaceutically acceptable salts of compounds of the formula I having salt-forming groups.

The invention relates chiefly to compounds of the formula I in which $R_1$ represents hydrogen, lower alkanoyl having from 1 to 7 carbon atoms, for example formyl, acetyl, propionyl or pivaloyl, hydroxy-lower alkanoyl, for example $\beta$-hydroxypropionyl, lower alkoxy-lower alkanoyl, for example lower alkoxyacetyl or lower alkoxypropionyl, such as methoxyacetyl or $\beta$-methoxypropionyl, lower alkanoyl etherified by a natural sugar that may, if desired, be acetylated or protected as the acetal, for example glucofuranosyl-0-lower alkanoyl, such as mono- or di-isopropylidene-glucofuranosyl-0-acetyl, lower alkanoyloxy-lower alkanoyl, for example lower alkanoyloxyacetyl or lower alkanoyloxypropionyl, such as acetoxyacetyl or $\beta$-acetoxypropionyl, halo-lower alkanoyl, for example haloacetyl, such as $\alpha$-chloro-, $\alpha$-bromo-, $\alpha$-iodo- or $\alpha,\alpha,\alpha$-trichloro-acetyl, or halopropionyl, such as $\beta$-chloro- or $\beta$-bromo-propionyl, hydroxysulphonyloxy-lower alkanoyl, for example hydroxysulphonyloxyacetyl or $\beta$-hydroxysulphonyloxypropionyl, carboxy-lower alkanoyl, for example carboxyacetyl or $\beta$-carboxypropionyl, lower alkoxycarbonyl-lower alkanoyl, for example lower alkoxycarbonylacetyl or lower alkoxycarbonylpropionyl, such as methoxycarbonylacetyl, $\beta$-methoxycarbonylpropionyl, ethoxycarbonylacetyl or $\beta$-ethoxycarbonylpropionyl, carbamoyl-lower alkanoyl, for example carbamoylacetyl or $\beta$-carbamoylpropionyl, lower alkylcarbamoyl-lower alkanoyl, for example methylcarbamoylacetyl, di-lower alkylcarbamoyl-lower alkanoyl, for example dimethylcarbamoylacetyl, aminoalkanoyl having from 1 to 10 carbon atoms, for example aminoacetyl, $\alpha$-aminopropionyl, $\gamma$-aminobutyryl or 8-aminooctanoyl, lower alkylamino-lower alkanoyl, for example methylaminoacetyl, di-lower alkylamino-lower alkanoyl, for example dimethylaminoacetyl, acylaminoalkanoyl, for example lower alkanoylaminoalkanoyl, such as acetylaminoacetyl, $\alpha$-acetylaminopropionyl or pivaloylaminoacetyl, lower alkoxycarbonylaminoalkanoyl, such as tert.-butoxycarbonylaminoacetyl, $\gamma$-tert.-butoxycarbonylaminobutyryl or 8-tert.-butoxycarbonylaminooctanoyl, aryl-lower alkoxycarbonylaminoalkanoyl, such as benzyloxycarbonylaminoacetyl, $\gamma$-benzyloxycarbonylaminobutyryl or 8-benzyloxycarbonylaminooctanoyl, substituted lower alkanoylamino-lower alkanoyl, such as $\gamma$-aminobutyrylaminoacetyl, $\gamma$-benzyloxycarbonylaminobutyrylaminoacetyl, ($\alpha$-amino-$\delta$-guanidinovaleryl)-aminoacetyl or ($\alpha$-benzyloxycarbonylamino-$\delta$-guanidinovaleryl)-aminoacetyl, also mercapto-lower alkanoyl, for example $\beta$-mercaptopropionyl, lower alkylthio-lower alkanoyl, for example $\beta$-methylthiopropionyl, oxo-lower alkanoyl, for example acetoacetyl or propionylacetyl, hydroxy-carboxy-lower alkanoyl, for example $\alpha$-hydroxy-$\alpha$-carboxyacetyl or $\alpha$-hydroxy-$\beta$-carboxypropionyl, hydroxy-lower alkoxycarbonyl-lower alkanoyl, for example $\alpha$-hydroxy-$\alpha$-ethoxy- or -methoxy-carbonylacetyl or $\alpha$-hydroxy-$\beta$62 -ethoxy- or -methoxy-carbonylpropionyl, esterified hydroxy-lower alkoxycarbonyl-lower alkanoyl, for example $\alpha$-acetoxy-$\alpha$-methoxycarbonylacetyl, dihydroxy-carboxy-lower alkanoyl, for example $\alpha,\beta$-dihydroxy-$\beta$-carboxypropionyl, dihydroxy-lower alkoxycarbonyl-lower alkanoyl, for example $\alpha,\beta$-dihydroxy-$\beta$-ethoxy- or -methoxy-carbonylpropionyl, esterified dihydroxy-lower alkoxycarbonyl-lower alkanoyl, for example $\alpha,\beta$-diacetoxy-2-ethoxy- or -methoxy-carbonylpropionyl, hydroxy-amino-lower alkanoyl, for example $\beta$-hydroxy-$\alpha$-aminopropionyl, $\beta$-hydroxy-$\alpha$-aminobutyryl or 3-hydroxy-4-amino-6-methylheptanoyl, hydroxy-acylamino-lower alkanoyl, for example $\beta$-hydroxy-$\alpha$-benzyloxycarbonylaminopropionyl or 3-hydroxy-4-benzyloxycarbonylamino-6-methylheptanoyl, carboxy-amino-lower alkanoyl, for example $\alpha$-carboxy-$\alpha$-aminoacetyl, $\beta$-carboxy-$\alpha$-aminopropionyl or $\gamma$-carboxy-$\alpha$-aminobutyryl, lower alkoxycarbonyl-amino-lower alkanoyl, for example $\alpha$-methoxy- or ethoxy-carbonyl-$\alpha$-aminoacetyl, carboxy-acylamino-lower alkanoyl, for example $\beta$-carboxy-$\alpha$-benzyloxycarbonylaminopropionyl or $\gamma$-carboxy-$\alpha$-benzyloxycarbonylaminobutyryl, lower alkoxycarbonyl-acylamino-lower alkanoyl, for example $\alpha$-methoxy- or ethoxy-carbonyl-$\alpha$-benzyloxycarbonylaminoacetyl or $\alpha$-methoxy- or ethoxy-carbonyl-$\alpha$-tert.-butoxycarbonylaminoacetyl, diamino-lower alkanoyl, for example 2,6-diaminohexanoyl, diacylamino-lower alkanoyl, for example 2,6-bis(benzyloxycarbonylamino)-hexanoyl, lower alkenoyl having from 3 to 7 carbon atoms, for example acryloyl, vinylacetyl, crotonoyl or 3- or 4-pentenoyl, lower alkynoyl having from 3 to 7 carbon atoms, for example propiolyl or 2- or 3-butynoyl, cycloalkylcarbonyl having from 4 to 9 carbon atoms, for example cyclopropylcarbonyl, cyclobutylcarbonyl, cyclopentylcarbonyl or cyclohexylcarbonyl, bicycloalkylcarbonyl having from 6 to 11 carbon atoms, for example bicyclo[3.1.0]hex-1-, -2- or -3-ylcarbonyl, bicyclo[4.1.0]hept-1- or -4-ylcarbonyl, bicyclo[3.3.0]-oct-3-ylcarbonyl or bicyclo[3.3.1]non-9-ylcarbonyl, tricycloalkylcarbonyl having from 9 to 11 carbon atoms, for example tricyclo[5.2.1.0$^{2,6}$]dec-8-ylcarbonyl or adamantylcarbonyl, monocycloalkenylcarbonyl having from 4 to 9 carbon atoms, for example 1-cyclohexenylcarbonyl or 1,4-cyclohexadienylcarbonyl, bicycloalkenylcarbonyl having from 6 to 11 carbon atoms, for example 5-norbornen-2-ylcarbonyl, bicyclo[2.2.2]octen-2-ylcarbonyl or hexahydro-4,7-methano-ind-1-en-6-ylcarbonyl, cycloalkyl-lower alkanoyl having from 5 to 11 carbon atoms, for example cyclopropylacetyl, cyclobutylacetyl, cyclopentylacetyl or cyclohexylacetyl, cycloalkyl-lower alkenoyl having from 6 to 11 carbon atoms, for example cyclohexylacryloyl, cycloalkenyl-lower alkanoyl having from 5 to 11 carbon atoms, for example 1-cyclohexenylacetyl or 1,4-cyclohexadienylacetyl, hydroxycycloalkylcarbonyl, for example 4-hydroxycyclohexylcarbonyl or 3,4,5-trihydroxycyclohexylcarbonyl, carboxycycloalkylcarbonyl, for example 4-carboxycyclohexylcarbonyl, aminocycloalkylcarbonyl, for example 1-aminocyclopropylcarbonyl or 4-aminocyclohexylcarbonyl, acylaminocycloalkylcarbonyl, for example 1-tert.-butoxycarbonylaminocyclopropylcarbonyl or 1-benzyloxycarbonylaminocyclopropylcarbonyl, hydroxycycloalkenylcarbonyl, for example 3,4,5-trihydroxycyclohex-1-enylcarbonyl, benzoyl that is unsubstituted or mono- or poly-substituted by lower alkyl, hydroxy, lower alkoxy, halo and/or by nitro, for example 4-chlorobenzoyl, 4-methoxybenzoyl or 4-nitrobenzoyl, phenyl-lower alkanoyl in which phenyl may be unsubstituted or mono- or poly-substituted by lower alkyl, hydroxy, lower alkoxy, halo and/or nitro, for example phenylacetyl, lower alkyl-phenylacetyl, for example 4-methylphenylacetyl, lower alkoxyphenylacetyl, for example 4-methoxyphenylacetyl, β-phenylpropionyl, β-(p-hydroxyphenyl)-propionyl, diphenylacetyl, di-(4-methoxyphenyl)-acetyl, triphenylacetyl, or also substituted anilinophenylacetyl, for example 2-(o,o-dichloroanilino)-phenylacetyl or 2-(o,o-dichloro-N-benzylanilino)-phenylacetyl, phenyl-lower alkenoyl, for example β-phenylacryloyl or β-phenylvinylacetyl, 2- or 3-pyrrolylcarbonyl, 2-, 3- or 4-pyridylcarbonyl, 2-, 3- or 5-indolylcarbonyl, 2-, 3- or 4-quinolinylcarbonyl-, 1-, 3- or 4-isoquinolinylcarbonyl, phenyl-hydroxy-lower alkanoyl, for example α-phenyl-α-hydroxy-acetyl, unsubstituted or substituted phenyl-amino-lower alkanoyl, for example β-phenyl-α-aminopropionyl or β-(4-hydroxyphenyl)-α-aminopropionyl, unsubstituted or substituted phenyl-acylamino-lower alkanoyl, for example β-phenyl-α-benzyloxycarbonylaminopropionyl or β-(4-acetoxyphenyl)-α-benzyloxycarbonylaminopropionyl, pyrrolidinyl-3-carbonyl, hydroxypyrrolidinylcarbonyl, for example 3- or 4-hydroxypyrrolidinyl-2-carbonyl, hydroxy-1-acylpyrrolidinylcarbonyl, for example 3- or 4-hydroxy-1-benzyloxycarbonylpyrrolidinyl-2-carbonyl, oxopyrrolidinylcarbonyl, for example 5-oxopyrrolidinyl-2-carbonyl, piperidinyl-2-, -3- or -4-carbonyl, 1-lower alkyl-piperidinylcarbonyl, for example 1-methylpiperidinyl-2-, -3- or -4-carbonyl, 1-acylpiperidinylcarbonyl, for example 1-benzyloxycarbonylpiperidinyl-2-, -3- or -4-carbonyl, morpholinyl-2- or -3-carbonyl, thiomorpholinyl-2- or -3-carbonyl, 1-and/or 4-lower alkyl-piperazinylcarbonyl, for example 1,4-dimethylpiperazinyl-2- or -3-carbonyl, or also lower alkoxycarbonyl, for example methoxycarbonyl, ethoxycarbonyl or tert.-lower alkoxycarbonyl, such as tert.-butoxycarbonyl, 2-halo-lower alkoxycarbonyl, for example 2-chloro-, 2-bromo-, 2-iodo- or 2,2,2-trichloro-ethoxycarbonyl, aryl-lower alkoxycarbonyl in which aryl is phenyl or 1- or 2-naphthyl, or phenyl that is mono- or poly-substituted by lower alkyl, for example methyl or tert.-butyl, lower alkoxy, for example methoxy, ethoxy or tert.-butoxy, hydroxy, halogen, for example chlorine or bromine, and/or by nitro, for example benzyloxycarbonyl, 4-methoxybenzyloxycarbonyl, 4-nitrobenzyloxycarbonyl, diphenylmethoxycarbonyl, di-(4-methoxyphenyl)-methoxycarbonyl or trityloxycarbonyl, each of $X_1$ and $X_2$, independently of the other, represents Ala, Arg, Asn, Asp, Cys, Gln, Glu, Gly, His, Ile, Leu, Lys, Met, Phe, Pro, Ser, Thr, Trp, Tyr or Val, but —$X_1$—$X_2$— does not represent -Val-Val-, -Gly-Gly- or -Tyr-Gly-, and in which optionally the carboxy function of the side chain in Asp and Glu is esterified by a lower alkanol, for example methanol or tert.-butanol, and/or the amino function of the side chain in Lys is acylated by lower alkanoyl, for example pivaloyl, by lower alkoxycarbonyl, for example tert.-butoxycarbonyl, or by aryl-lower alkoxycarbonyl, for example benzyloxycarbonyl, $X_1$ is bonded N-terminally to $R_1$ and C-terminally to $X_2$, and $X_2$ is bonded N-terminally to $X_1$ and C-terminally to —$NR_2$—, and $X_2$ may be substituted at the N atom by lower alkyl, $R_2$ represents hydrogen or lower alkyl, $R_3$ represents hydrogen, lower alkyl, for example isopropyl or isobutyl, cycloalkyl, phenyl-lower alkyl or phenyl, $R_4$ represents hydroxy, $R_5$ represents alkyl having from 1 to 10 carbon atoms, for example lower alkyl, such as isopropyl or isobutyl, or n-octyl, cycloalkyl, for example cyclohexyl, phenyl-lower alkyl, for example benzyl, or phenyl, and $R_6$ represents amino, alkylamino having from 1 to 10 carbon atoms, for example methyl-, ethyl-, n-propyl-, n-butyl-, isobutyl-, tert.-butyl-, n-pentyl-, n-hexyl-, n-octyl- or n-decyl-amino, di-lower alkylamino, for example dimethylamino or diethylamino, hydroxy-lower alkylamino, for example 2-hydroxyethylamino, 3-hydroxypropylamino or tris-(hydroxymethyl)-methylamino, di-(hydroxy-lower alkyl)-amino, for example di-(2-hydroxyethyl)-amino, lower alkoxy-lower alkylamino, for example methoxymethylamino or 2-methoxyethylamino, lower alkanoyloxy-lower alkylamino, for example acetoxymethylamino or 2-acetoxyethylamino, halo-lower alkylamino, for example halomethyl- or haloethyl-amino, such as trifluoromethyl-, chloromethyl-, bromomethyl-, 2-chloroethyl-, 2-bromoethyl- or 2,2,2-trichloroethylamino, hydroxysulphonyloxy-lower alkylamino, for example hydroxysulphonyloxymethylamino or 2-hydroxysulphonyloxyethylamino, phenoxy-lower alkylamino or phenoxyhydroxy-lower alkylamino in which phenyl is optionally substituted by lower alkyl, lower alkoxy, hydroxy, carboxy, lower alkoxycarbonyl or by carbamoyl, for example 2-phenoxyethyl-, 2-(3-carbamoyl-4-hydroxyphenoxy)-ethyl- or 3-(3-carbamoylphenoxy)-2-hydroxypropylamino, carboxyalkylamino, for example 4-carboxy-n-butyl-, 5-carboxy-n-pentyl-, 6-carboxy-n-hexyl-, 7-carboxy-n-heptyl-, 8-carboxy-n-octyl-, 2-carboxyethyl-, 2-carboxy-n-propyl- or 1- or 2-carboxyprop-2-yl-amino, lower alkoxycarbonylalkylamino, for example 4-tert.-butoxycarbonyl-n-butyl-, 7-tert.-butoxycarbonyl-n-heptyl-, 8-tert.-butoxycarbonyl-n-octyl-, 2-tert.-butoxycarbonylethyl- or 1-tert.-butoxycarbonylprop-2-yl-amino, physiologically cleavable esterified carboxyalkylamino, for example 4-pivaloyloxymethoxycarbonyl-n-butylamino, 7-(1-ethoxy-carbonyloxyethoxycarbonyl)-n-heptylamino or 7-pivaloyloxymethoxycarbonyl-n-heptylamino, carbamoyl-lower alkylamino, for example carbamoylmethylamino, 2-carbamoylethylamino or dicarbamoylmethylamino, lower alkylcarbamoyl-lower alkylamino, for example methylcarbamoylmethylamino, hydroxy-lower alkylcarbamoyl-lower alkylamino, for example 7-(2-hydroxyethyl)-carbamoyl-n- heptyl-, 4-(2-hydroxyethyl)-carbamoyl-n-butyl-, 7-(tris-[hydroxymethyl]-methyl)-carbamoyl-n-heptyl- or 4-(tris-[hydroxymethyl]-methyl)-carbamoyl-n-butyl-amino, tri-lower alkylsilyloxy-lower alkylcarbamoyl-lower alkylamino, for example 4-(tris-[tert.-butyldimethylsilyloxymethyl]-methyl)carbamoyl-n-butylamino, lower alkoxycarbonyl-hydroxy-lower alkylcarbamoyl-lower alkylamino, for example α-carbamoyl-α-(2-hydroxy-1-isobutyl-3-methoxycarbonylpropyl)-carbamoyl-methylamino, di-lower alkylcarbamoyl-lower alkylamino, for example dimethylcarbamoylmethylamino or bis-dimethylcarbamoylmethylamino, sulphosulphoethylamino, aminoalkylamino, for example 4-amino-n-butyl-, 5-amino-n-pentyl-, 6-amino-n-hexyl-, 7-amino-n-heptyl-, 8-amino-n-octyl-, 2-amino-ethyl- or 1-amino-prop-2-yl-amino, lower alkylamino-lower alkylamino, for example 2-methylaminoethylamino or 3-methylamino-n-propylamino, hydroxy-lower alkylamino-lower alkylamino, for example 2-(2-hydroxyethylamino)-ethylamino or 3-(2-hydroxyethylamino)-n-propylamino, di-lower alkylamino-lower alkylamino, for example 2-dimethylaminoethylamino or 3-dimethylamino-n-propylamino, 1-piperidinyl-lower alkylamino, for example 2-(1-piperidinyl)-ethylamino or 3-(1-piperidinyl)-propylamino, 4-morpholinyl-lower alkylamino, for example 2-(4-morpholinyl)-ethylamino or 3-(4-morpholinyl)-propylamino, 1-pyrrolidinyl-lower alkylamino in which pyrrolidine is optionally substituted by hydroxy and/or oxo, for example 2-(2-oxopyrrolidin-1-yl)-ethylamino or 3-(2-oxopyrrolidin-1-yl)-propylamino, acylaminoalkylamino, for example lower alkanoylaminoalkylamino, for example pivaloylaminoalkylamino or acetylaminoalkylamino, such as 4-pivaloylamino-n-butylamino, 2-pivaloylaminoethylamino or 4-acetylamino-n-butylamino, lower alkoxycarbonyl-aminoalkylamino, such as 4-tert.-butoxycarbonyl-amino-n-butyl-, 5-tert.-butoxycarbonylamino-n-pentyl-, 6-tert.-butoxycarbonylamino-n-hexyl-, 7-tert.-butoxycarbonylamino-n-heptyl- or 2-tert.-butoxycarbonylaminoethyl-amino, lower alkenylamino, for example allylamino or 2- or 3-butenylamino, lower alkynylamino, for example propargylamino, phenylamino or phenyl-lower alkylamino in which phenyl is optionally mono- or poly-substituted by lower alkyl, for example methyl, hydroxy, lower alkoxy, for example methoxy or tert.-butoxy, lower alkanoyloxy, for example acetoxy, halogen, for example fluorine or chlorine, carboxy, lower alkoxycarbonyl, for example tert.-butoxycarbonyl, carbamoyl, amino, lower alkylamino, for example methylamino, di-lower alkylamino, for example dimethylamino, acylamino, for example tert.-butoxycarbonylamino, and/or by nitro, for example phenyl-, 2-, 3- or 4-methylphenyl-, 4-hydroxyphenyl-, 4-methoxyphenyl-, 2,3-, 2,4- or 2,5-dimethoxyphenyl-, 4-chlorophenyl-, 2-, 3- or 4-carboxyphenyl-, 2-, 3- or 4-methoxy- or tert.-butoxycarbonylphenyl-, 2-, 3- or 4-carbamoylphenyl-, 4-aminophenyl-, 4-tert.-butoxycarbonylaminophenyl- or 4-nitrophenyl-amino, or also, for example, benzylamino, 4-methylbenzylamino, 4-methoxybenzylamino, 2-, 3- or 4-carboxybenzylamino, 2-, 3- or 4-tert.-butoxycarbonylbenzylamino, 2-, 3- or 4-carbamoylbenzylamino, 2-phenylethylamino, 2-phenylprop-2-ylamino or 3-phenylpropylamino, phenyl-lower alkylamino in which lower alkyl is substituted by hydroxy, cyano, carboxy, lower alkoxy and/or by carbamoyl, for example 1-hydroxymethyl-2-phenylethylamino, 2-hydroxy-1- or -2-phenylethylamino, or 1-(2-cyano- or -2-carboxy-1-hydroxyethyl)-2-phenylethylamino, oxazolylamino, for example 2-oxazolylamino, thiazolylamino that is optionally substituted by carboxy-lower alkyl, for example carboxymethyl, lower alkoxycarbonyl-lower alkyl, for example methoxycarbonylmethyl, or by carbamoyl-lower alkyl, for example carbamoylmethyl, for example 4- or 5-carboxymethyl-2-thiazolylamino or 4- or 5-carbamoylmethyl-2-thiazolylamino, pyridyl-lower alkylamino, for example 2-, 3- or 4-pyridylmethyl-, 2-(2-, 3- or 4-pyridyl)ethyl- or 3-(2-, 3- or 4-pyridyl)-propyl-amino, imidazolyl-lower alkylamino, for example 4-imidazolylmethylamino or 2-(4-imidazolyl)-ethylamino, indolyl-lower alkylamino, for example 3-indolylmethylamino or 2-(3-indolyl)-ethylamino, 1-benzylpiperidinylamino, for example 1-benzylpiperidin-4-ylamino, 1-lower alkoxycarbonylpiperidinylamino, for example 1-ethoxy- or 1-n-butoxy-carbonylpiperidin-2-, -3- or -4-ylamino, or also lower alkoxy, for example methoxy, ethoxy, n-propoxy, isopropoxy, butoxy, isobutoxy, tert.-butoxy or tert.-pentoxy, phenoxy, phenyl-lower alkoxy, for example benzyloxy or diphenylmethoxy, or physiologically cleavable alkoxy, for example pivaloyloxymethoxy, or also -His-, -Phe-, -Ala- or -Ile- C-terminally substituted by amino, alkylamino, for example methyl-, ethyl-, n-propyl-, n-butyl- or n-octyl-amino, di-lower alkylamino, for example dimethylamino, hydroxy-lower alkylamino, for example 2-hydroxyethylamino or tris-(hydroxymethyl)-methylamino, carboxyalkylamino, for example 4-carboxy-n-butylamino or 1-carboxyprop-2-ylamino, lower alkoxycarbonylalkylamino, for example 4-tert.-butoxycarbonyl-n-butylamino or 7-tert.-butoxycarbonyl-n-heptylamino, physiologically cleavable, esterified carboxyalkylamino, for example 4-pivaloyloxymethoxycarbonyl-n-butylamino, carbamoyl-lower alkylamino, for example carbamoylmethylamino or dicarbamoylmethylamino, hydroxy-lower alkylcarbamoyl-lower alkylamino, for example 2-hydroxyethylcarbamoyl-methylamino or di-(2-hydroxyethylcarbamoyl)-methylamino, aminoalkylamino, for example 4-amino-n-butylamino, 5-amino-n-pentylamino or 8-amino-n-octylamino, hydroxy-lower alkylamino-lower alkylamino, for example 2-(2-hydroxyethylamino)-ethylamino, di-lower alkylamino-lower alkylamino, for example 2-dimethylaminoethylamino, five-or six-membered heterocyclyl-lower alkylamino bonded by way of a nitrogen atom, for example 3-(4-morpholinyl)-propylamino, 2-(4-morpholinyl)-ethylamino or 3-(2-oxo-1-pyrrolidinyl)-propylamino, acylamino-lower alkylamino, for example lower alkoxycarbonylamino-lower alkylamino, such as 4-tert.-butoxycarbonylamino-n-butylamino, phenyl-lower alkylamino in which phenyl may be substituted by carboxy, lower alkoxycarbonyl or carbamoyl, and lower alkyl may be substituted by hydroxy, cyano or by carboxy, for example benzylamino, carboxybenzylamino, for example 3-carboxybenzylamino, lower alkoxycarbonylbenzylamino, for example 3-tert.-butoxycarbonylbenzylamino, carbamoylbenzylamino, for example 3-carbamoylbenzylamino, 2-phenylethylamino, 1-phenylprop-2-yl-amino, 3-phenylpropylamino, 1-hydroxymethyl-2-phenylethylamino, 2-hydroxy-1- or -2-phenylethylamino, 1-(2-cyano- or 2-carboxy-1-hydroxyethyl)-2-phenylethylamino, unsubstituted or substituted thiazolylamino, for example 2-thiazolylamino or 4- or 5-carbamoylmethyl-2-thiazolylamino, pyridyl-lower alkylamino, for example 2-, 3- or 4-pyridylmethylamino, 2-(2-, 3- or 4-pyridyl)-ethylamino, 3-(2-, 3- or 4-pyridyl)-propylamino, imidazolyl-lower alkylamino, for example 4-imidazolylmethylamino or 2-(4-imidazolyl)-ethylamino, indolyl-lower alkylamino, for example 3-indolylmethylamino or 2-(3-indolyl)-ethylamino, piperidinylamino, for example 1-benzyl-piperidin-2-, -3- or -4-ylamino, 1-lower alkoxycarbonyl-piperidinylamino, for example 1-ethoxy- or 1-n-butoxy-carbonylpiperidin-2-, -3- or -4-ylamino, or also by lower alkoxy, for example methoxy, ethoxy or tert.-butoxy, or physiologically cleavable substituted alkoxy, for example pivaloyloxymethoxy, also -Ile-His-, -Ile-Phe-, -Ala-His-, -Gly-Gly-, -Gly-His-, -Gly-Ala-, -Gly-Ser-, -Ala-Sta-, -Ile-Sta-, -Gly-Gly-Gly-, -Gly-His-Lys-, -Gly-Ala-Gly- or -Ile-His-Lys- in which the amino function in the side chain of -Lys- is optionally acylated by lower alkanoyl, for example pivaloyl, lower alkoxycarbonyl, for example tert.-butoxycarbonyl, or by phenyl-lower alkoxycarbonyl, for example benzyloxycarbonyl, C-terminally substituted by amino, lower alkylamino, for example methyl-, ethyl-, n-propyl- or n-butyl-amino, di-lower alkylamino, for example dimethylamino, hydroxy-lower alkylamino, for example 2-hydroxyethylamino or tris-(hydroxymethyl)-methylamino, or also by lower alkoxy, for example methoxy, ethoxy or tert.-butoxy, or by physiologically cleavable substituted alkoxy, for example pivaloyloxymethoxy, and to pharmaceutically acceptable salts of these compounds having salt-forming groups.

The invention relates most especially to compounds of the formula I in which $R_1$ represents hydrogen, lower alkanoyl, for example formyl, acetyl, propionyl or pivaloyl, lower alkoxy-lower alkanoyl, for example methoxyacetyl, mono- or di-isopropylidene-gluco- furanosyl-O-acetyl, for example 1,2-mono- or 1,2:5,6-di-isopropylidene-glucofurano-syl-3-0-acetyl, halo-lower alkanoyl, for example $\alpha$-haloacetyl, for example $\alpha$-chloro-, $\alpha$-bromo-, $\alpha$-iodo- or $\alpha,\alpha,\alpha$-trichloro-acetyl, carboxy-lower alkanoyl, for example carboxyacetyl, lower alkoxycarbonyl-lower alkanoyl, for example methoxycarbonylacetyl, aminoalkanoyl, for example aminoacetyl, $\alpha$-aminopropionyl, $\gamma$-aminobutyryl or 8-aminooctanoyl, acylaminoalkanoyl, for example lower alkanoylaminoalkanoyl, such as acetylaminoacetyl or pivaloylaminoacetyl, lower alkoxycarbonylaminoalkanoyl, such as tert.-butoxycarbonylaminoacetyl, $\gamma$-(tert. -butoxycarbonylamino)-butyryl or 8-(tert.-butoxycarbonylamino)-octanoyl, phenyl-lower alkoxycarbonylaminoalkanoyl, such as benzyloxycarbonylaminoacetyl, $\gamma$-(benzyloxycarbonylamino)-butyryl or 8-(benzyloxycarbonylamino)-octanoyl, $\gamma$-aminobutyryl-aminoacetyl, $\gamma$benzyloxycarbonylaminobutyryl-aminoacetyl, ($\alpha$-amino$\delta$-guanidinovaleryl)-aminoacetyl or ($\alpha$-benzyloxycarbonylamino-$\delta$-guanidinovaleryl)-aminoacetyl, oxo-lower alkanoyl, for example acetoacetyl, hydroxycarboxy-lower alkanoyl, for example $\alpha$-hydroxy-$\beta$-carboxypropionyl, hydroxy-lower alkoxycarbonyl-lower alkanoyl, for example $\alpha$-hydroxy-$\beta$-ethoxy- or -methoxycarbonylpropionyl, dihydroxy-carboxy-lower alkanoyl, for example $\alpha,\beta$-dihydroxy-$\beta$-carboxypropionyl, dihydroxylower alkoxycarbonyl-lower alkanoyl, for example $\alpha,\beta$-dihydroxy-$\beta$-ethoxy- or -methoxy-carbonylpropionyl, esterified dihydroxy-lower alkoxycarbonyl-lower alkanoyl, for example $\alpha,\beta$-diacetoxy-$\beta$-methoxycarbonylpropionyl, hydroxy-amino-lower alkanoyl, for example $\beta$-hydroxy-$\alpha$-aminopropionyl or 3-hydroxy-4-amino-6-methylheptanoyl, hydroxyacylamino-lower alkanoyl, for example $\beta$-hydroxy-$\alpha$-benzyloxycarbonylaminopropionyl or 3-hydroxy-4-benzyloxycarbonylamino-b 6-methylheptanoyl, carboxy-amino-lower alkanoyl, for example $\alpha$-carboxy-$\alpha$-aminoacetyl, lower alkoxycarbonyl-amino-lower alkanoyl, for example $\alpha$-methoxy- or ethoxy-carbonyl-$\alpha$-aminoacetyl, lower alkoxycarbonyl-acylamino-lower alkanoyl, for example $\alpha$-methoxy- or ethoxy-carbonyl-$\alpha$-benzyloxycarbonylaminoacetyl, lower alkenoyl, for example acryloyl or crotonoyl, lower alkynoyl, for example propiolyl, cyclopentyl- or cyclohexyl-carbonyl, hydroxycyclohexylcarbonyl, for example 3,4,5-trihydroxycyclohexylcarbonyl, acylaminocycloalkylcarbonyl, for example 1-tert.-butoxycarbonylaminocyclopropylcarbonyl or 1-benzyloxycarbonylaminocyclopropylcarbonyl, 3,4,5-trihydroxycyclohex-1-enylcarbonyl, benzoyl or benzoyl that is substituted by halogen, for example chlorine, lower alkoxy, for example methoxy, and/or by nitro, for example 4-chloro-, 4-methoxy- or 4-nitro-benzoyl, 2-(o,o-dichloroanilino)-phenylacetyl, 2-(o,o-dichloro-N-benzylanilino)-phenylacetyl, hydroxypyrrolidinylcarbonyl, for example 3- or 4-hydroxypyrrolidinyl-2-carbonyl, hydroxy-1-acyl-pyrrolidinylcarbonyl, for example 3- or 4-hydroxy-1-benzyloxycarbonylpyrrolidinyl-2-carbonyl, oxopyrrolidinylcarbonyl, for example 5-oxopyrrolidinyl-2-carbonyl, lower alkoxycarbonyl, for example tert.-butoxycarbonyl, 2-halo-lower alkoxycarbonyl, for example 2-chloro-, 2-bromo-, 2-iodo- or 2,2,2-trichloro-ethoxycarbonyl, arylmethoxycarbonyl having one or two aryl radicals in which aryl is phenyl optionally mono-, di- or trisubstituted by lower alkyl, for example methyl or tert.-butyl, lower alkoxy, for example methoxy, hydroxy, halogen, for example chlorine, and/or by nitro, for example benzyloxycarbonyl, 4-nitrobenzyloxycarbonyl, diphenylmethoxycarbonyl or di-(4-methoxyphenyl)methoxycarbonyl, $X_1$ and $X_2$ together represent -Phe-His-, -Phe-Phe-, -Phe-(N-methyl-Phe)-, -Phe-Leu-, -Phe-Ala-, -Phe-Arg-, -Phe-Gly-, -His-His-, -Arg-Arg-, -Arg-His-, -Arg-Phe- or -Glu-His- which are bonded N-terminally to $R_1$ and C-terminally to the group -NR$_2$-, $R_2$ represents hydrogen, $R_3$ represents lower alkyl, for example isopropyl or isobutyl, $R_4$ represents hydroxy, $R_5$ represents alkyl, for example lower alkyl, such as isopropyl or isobutyl, or n-octyl, cyclohexyl or phenyl, and $R_6$ represents amino, alkylamino, for example methyl-, ethyl-, n-propyl-, n-butyl-, isobutyl-, tert.-butyl-, n-pentyl-, n-hexyl-, n-octyl-or n-decyl-amino, di-lower alkylamino, for example dimethylamino, hydroxy-lower alkylamino, for example 2-hydroxyethylamino or tris-(hydroxymethyl)-methylamino, lower alkoxy-lower alkylamino, for example 2-methoxyethylamino, substituted phenoxy-lower alkylamino, for example 2-(3-carbamoyl-4-hydroxyphenoxy)ethylamino, substituted phenoxy-hydroxy-lower alkylamino, for example 3-(3-carbamoylphenoxy)-2-hydroxypropylamino, carboxyalkylamino, for example 4-carboxy-n-butylamino, 5-carboxy-n-pentylamino, 6-carboxy-n-hexylamino, 7-carboxy-n-heptylamino, 8-carboxy-n-octylamino or 1-carboxyprop-2-ylamino, lower alkoxycarbonylalkylamino, for example 4-tert.-butoxycarbonyl-n-butylamino, 7-tert.-butoxycarbonyl-n-heptylamino or 8-tert.-butoxycarbonyl-n-octylamino, physiologically cleavable esterified carboxyalkylamino, for example 4-pivaloyloxymethoxycarbonyl-n-butylamino, 7-(1-ethoxycarbonyloxyethoxycarbonyl)-n-heptylamino or 7-pivaloyloxymethoxycarbonyl-n-heptylamino, carbamoyl-lower alkylamino, for example carbamoylmethylamino or dicarbamoylmethylamino, hydroxy-lower alkylcarbamoyllower alkylamino, for example 4-(tris[hydroxymethyl]methyl)-carbamoyl-n-butylamino, lower alkoxycarbonylhydroxy -lower alkylcarbamoyl-lower alkylamino, for example α-carbamoyl-α-(2-hydroxy-1-isobutyl-3-methoxycarbonylpropyl) -carbamoyl-methylamino, aminoalkylamino, for example 4-amino-n-butylamino, 5-amino-n-pentylamino, 6-amino-n-hexylamino, 7-amino-n-heptylamino or 8-amino-n-octylamino, hydroxy-lower alkylamino-lower alkylamino, for example 2-(2-hydroxyethylamino)-ethylamino, di-lower alkylamino-lower alkylamino, for example 2-dimethylaminoethylamino, five- or six-membered heterocyclyl-lower alkylamino bonded by way of a nitrogen atom, for example 3-(4-morpholinyl)-propylamino or 3-(2-oxo-1-pyrrolidinyl)- propylamino, acylamino-lower alkylamino, for example lower alkanoylamino-lower alkylamino, such as 4-pivaloylamino-n-butylamino, or lower alkoxycarbonylamino-lower alkylamino, such as 4-tert.-butoxycarbonylamino-n-butylamino, 5-tert.-butoxycarbonylaminon-pentylamino, 6-tert.-butoxycarbonylamino-n-hexylamino, 7-tert.-butoxycarbonylamino-n-heptylamino or 8-tert.-butoxycarbonylamino-n-octylamino, benzylamino, carboxybenzylamino, for example 3-carboxybenzylamino, lower alkoxycarbonylbenzylamino, for example 3-tert.-butoxycarbonylbenzylamino, or also lower alkoxy, for example methoxy, ethoxy, n-propoxy, isopropoxy, butoxy, isobutoxy, tert.-butoxy or tert.-pentoxy, or physiologically cleavable alkoxy, for example pivaloyloxymethoxy, or also -Ala- or -Ile- C-terminally substituted by amino, alkylamino, for example methyl-, ethyl-, n-propyl-, n-butyl- or n-octyl-amino, di-lower alkylamino, for example dimethylamino, hydroxy-lower alkylamino, for example 2-hydroxyethylamino or tris-(hydroxymethyl)-methylamino, carboxyalkylamino, for example 4-carboxy-n-butylamino or 1-carboxyprop-2-ylamino, carbamoyl-lower alkylamino, for example carbamoylmethylamino or dicarbamoylmethylamino, hydroxy-lower alkylcarbamoyl-lower alkylamino, for example 2-hydroxyethylcarbamoylmethylamino or di-(2-hydroxethylcarbamoyl)-methylamino, aminoalkylamino, for example 4-amino-n-butylamino, 5-amino-n-pentylamino or 8-amino-n-octylamino, hydroxy-lower alkylamino-lower alkylamino, for example 2-(2-hydroxyethylamino)-ethylamino, di-lower alkylamino-lower alkylamino, for example 2-dimethylaminoethylamino, 4-morpholinyl-lower alkylamino, for example 3-(4-morpholinyl)-propylamino or 2-(4-morpholinyl)-ethylamino, phenyl-lower alkylamino, for example benzylamino, carboxybenzylamino, for example 3-carboxybenzylamino, lower alkoxycarbonylbenzylamino, for example 3-tert.-butoxycarbonylbenzylamino, carbamoylbenzylamino, for example 3-carbamoylbenzylamino, 2-phenylethylamino, 1-phenylprop-2-ylamino, 3-phenylpropylamino, 1-hydroxymethyl-2-phenylethylamino, 2-hydroxy-1- or -2-phenylethylamino, 1-(2-cyano- or 2-carboxy-1-hydroxyethyl)-2-phenylethylamino, thiazolylamino, for example 4- or 5-carbamoylmethyl-2-thiazolylamino, pyridyl-lower alkylamino, for example 2-, 3- or 4-pyridylmethylamino, 2-(2-, 3- or 4-pyridyl)-ethylamino, 3-(2-, 3- or 4-pyridyl)-propylamino, imidazolyl-lower alkylamino, for example 4-imidazolylmethylamino or 2-(4-imidazolyl)-ethylamino, indolyl-lower alkylamino, for example 3-indolylmethylamino or 2-(3-indolyl)-ethylamino, 1-lower alkoxycarbonylpiperidinylamino, for example 1-ethoxycarbonylpiperidin-4-ylamino, lower alkoxy, for example methoxy, ethoxy or tert.-butoxy, or by physiologically cleavable substituted alkoxy, for example pivaloyloxymethoxy, or also -Ile-His-, -Ile-Phe-, -Ile-Sta-, -Ala-His-, -Ala-Sta- or -Ile-His-Lys- in which the amino function in the side chain of -Lys- is optionally acylated by lower alkanoyl, for example pivaloyl, lower alkoxycarbonyl, for example tert.-butoxycarbonyl, or by phenyl-lower alkoxycarbonyl, for example benzyloxycarbonyl, C-terminally substituted by amino, lower alkylamino, for example methyl-, ethyl-, n-propyl- or n-butyl-amino, di-lower alkylamino, for example dimethylamino, hydroxy-lower alkylamino, for example 2-hydroxyethylamino or tris-(hydroxymethyl)-methylamino, or also by lower alkoxy, for example methoxy, ethoxy or tert.-butoxy, or by physiologically cleavable substituted alkoxy, for example pivaloyloxymethoxy, and to pharmaceutically acceptable salts of these compounds having salt-forming groups.

The invention relates preferably to compounds of the formula I in which $R_1$ represents hydrogen, lower alkanoyl, for example formyl, acetyl, propionyl or pivaloyl, mono- or di-isopropylidene-glucofuranosyl O-acetyl, for example 1,2-mono- or 1,2:5,6-di-isopropylidene-glucofuranosyl-3-0-acetyl, aminoalkanoyl, for example aminoacetyl, α-aminopropionyl, γ-aminobutyryl or 8-aminooctanoyl, acylaminoalkanoyl, for example lower alkanoylaminoalkanoyl, such as acetylaminoacetyl or pivaloylaminoacetyl, lower alkoxycarbonylaminoalkanoyl, such as tert.-butoxycarbonylaminoacetyl, γ-(tert.-butoxycarbonylamino)-butyryl or 8-(tert.-butoxycarbonylamino)-octanoyl, phenyl-lower alkoxycarbonylaminoalkanoyl, such as benzyloxycarbonylaminoacetyl, γ-(benzyloxycarbonylamino)-butyryl or 8-(benzyloxycarbonylamino)-octanoyl, γ-aminobutyrylaminoacetyl, γ-benzyloxycarbonylaminobutyryl-aminoacetyl, (α-amino-δ-guanidinovaleryl)-aminoacetyl or (α-benzyloxycarbonylamino-δ-guanidinovaleryl)-aminoacetyl, hydroxy-carboxy-lower alkanoyl, for example α-hydroxyβ-carboxypropionyl, hydroxy-lower alkoxycarbonyllower alkanoyl, for example α-hydroxy-β-ethoxy- or -methoxy-carbonylpropionyl, dihydroxycarboxy lower alkanoyl, for example α,β-dihydroxy-β-carboxypropionyl, dihydroxy-lower alkoxycarbonyl-lower alkanoyl, for example α,β-dihydroxy-β-ethoxy- or -methoxy-carbonylpropionyl, esterified dihydroxy-lower alkoxycarbonyllower alkanoyl, for example α,β-diacetoxy-β-methoxycarbonylpropionyl, hydroxy-amino-lower alkanoyl, for example β-hydroxy-α-aminopropionyl or 3-hydroxy-4-amino-6-methylheptanoyl, lower alkoxycarbonylacylamino-lower alkanoyl, for example α-methoxy- or ethoxy-carbonyl-α-benzyloxycarbonylaminoacetyl, hydroxycyclohexylcarbonyl, for example 3,4,5-trihydroxycyclohexylcarbonyl, hydroxycyclohexenylcarbonyl, for example 3,4,5-trihydroxycyclohex-1-enylcarbonyl, 2-(o,o-dichloroanilino)-phenylacetyl, 2-(o,o-dichloro-N-benzylanilino)-phenylacetyl, hydroxypyrrolidinylcarbonyl, for example 3- or 4-hydroxypyrrolidinyl-2-carbonyl, hydroxy-1-acylpyrrolidinylcarbonyl, for example 3- or 4-hydroxy-1benzyloxycarbonylpyrrolidinyl-2-carbonyl, oxopyrrolidinylcarbonyl, for example 5-oxopyrrolidinyl-2-carbonyl, lower alkoxycarbonyl, for example tert.-butoxycarbonyl, or phenylmethoxycarbonyl having one or two phenyl radicals which are optionally substituted by lower alkyl, for example methyl, lower alkoxy, for example methoxy, and/or by nitro, for example benzyloxycarbonyl, 4-nitrobenzyloxycarbonyl, diphenylmethoxycarbonyl or di-(4-methoxyphenyl)-methoxycarbonyl, $X_1$ and $X_2$ together represent -Phe-His-, -Phe-Phe-, -Phe-Leu-, -Arg-His- or -Arg-Phe- which are bonded N-terminally to $R_1$ and C-terminally to the group —$NR_2$—, $R_2$ represents hydrogen, $R_3$ represents isopropyl or isobutyl, $R_4$ represents hydroxy, $R_5$ represents isopropyl, n-octyl, cyclohexyl or phenyl, and $R_6$ represents amino, alkylamino, for example methyl-, ethyl-, n-propyl-, n-butyl-, isobutyl-, tert.-butyl-, n-pentyl-, n-hexyl-, n-octyl- or n-decyl-amino, di-lower alkylamino, for example dimethylamino, hydroxy-lower alkylamino, for example 2-hydroxyethylamino or tris-(hydroxymethyl)-methylamino, lower alkoxy-lower alkylamino, for example 2-methoxyethylamino, substituted phenoxy-lower alkylamino, for example 2-(3-carbamoyl-4-hydroxyphenoxy)-ethylamino, substituted phenoxy-hydroxylower alkylamino, for example 3-(3-carbamoylphenoxy)-2-hydroxypropylamino, carboxyalkylamino, for example 4-carboxy-n-butylamino, 5-carboxy-n-pentylamino, 6-carboxy-n-hexylamino, 7-carboxy-n-heptylamino, 8-carboxy-n-octylamino or 1-carboxyprop-2-ylamino, lower alkoxycarbonylalkylamino, for example 4-tert.-butoxy-carbonyl-n-butylamino, 7-tert.-butoxycarbonyl-n-heptylamino or 8-tert.-butoxycarbonyl-n-octylamino, physiologically cleavable esterified carboxyalkylamino, for example 4-pivaloyloxymethoxycarbonyl-n-butylamino, 7-(1-ethoxycarbonyloxyethoxycarbonyl)-n-heptylamino or 7-pivaloyloxymethoxycarbonyl-n-heptylamino, carbamoyllower alkylamino, for example carbamoylmethylamino or dicarbamoylmethylamino, hydroxy-lower alkylcarbamoyllower alkylamino, for example 4-(tris[hydroxymethyl]methyl)-carbamoyl-n-butylamino, lower alkoxycarbonylhydroxy-lower alkoxycarbamoyl-lower alkylamino, for example $\alpha$-carbamoyl-$\alpha$-(2-hydroxy-1-isobutyl-3-methoxycarbonylpropyl) -carbamoyl-methylamino, aminoalkylamino, for example 4-amino-n-butylamino, 5-amino-n-pentylamino, 6-amino-n-hexylamino, 7-aminon-heptylamino or 8-amino-n-octylamino, hydroxy-lower alkylamino-lower alkylamino, for example 2-(2-hydroxyethylamino)-ethylamino, di-lower alkylamino-lower alkylamino, for example 2-dimethylaminoethylamino, five- or six-membered heterocyclyl-lower alkylamino bonded by way of a nitrogen atom, for example 3-(1-morpholinyl)-propylamino or 3-(2-oxo-1-pyrrolidinyl)-propylamino, acylamino-lower alkylamino, for example lower alkanoylamino-lower alkylamino, such as 4-pivaloylamino-n-butylamino, or lower alkoxycarbonylamino-lower alkylamino, such as 4-tert.-butoxycarbonylamino-n-butylamino, 5-tert.-butoxycarbonylamino-n-pentylamino, 6-tert.-butoxycarbonylamino-n-hexylamino, 7-tert.-butoxycarbonylamino-n-heptylamino or 8-tert.-butoxycarbonylamino-n-octylamino, benzylamino, carboxybenzylamino, for example 3-carboxybenzylamino, or also lower alkoxycarbonylbenzylamino, for example 3-tert.-butoxycarbonylbenzylamino, lower alkoxy, for example methoxy, ethoxy, n-propoxy, isopropoxy, butoxy, isobutoxy, tert.-butoxy or tert.-pentoxy, or physiologically cleavable alkoxy, for example pivaloyloxymethoxy, or also -Ala- or -Ile- C-terminally substituted by amino, alkylamino, for example methyl-, ethyl-, n-propyl-, n-butyl- or n-octyl-amino, di-lower alkylamino, for example dimethylamino, hydroxy-lower alkylamino, for example 2-hydroxyethylamino or tris-(hydroxymethyl)-methylamino, carboxyalkylamino, for example 4-carboxy-n-butylamino or 1-carboxyprop-2-ylamino, carbamoyl-lower alkylamino, for example carbamoylmethylamino or dicarbamoylmethylamino, hydroxy-lower alkylcarbamoyl-lower alkylamino, for example 2-hydroxyethylcarbamoylmethylamino or di-(2-hydroxyethylcarbamoyl)-methylamino, aminoalkylamino, for example 4-amino-n-butylamino, 5-aminon-n-pentylamino or 8-amino-n-octylamino, hydroxy-lower alkylamino-lower alkylamino, for example 2-(2-hydroxyethylamino)-ethylamino, 4-morpholinyl-lower alkylamino, for example 2-(4-morpholinyl)-ethylamino, carboxybenzylamino, for example 3-carboxybenzylamino, carbamoylbenzylamino, for example 3-carbamoylbenzylamino, thiazolylamino, for example 4- or 5-carbamoylmethyl-b 2-thiazolylamino, pyridyl-lower alkylamino, for example 2-, 3- or 4-pyridylmethylamino, 2-(2-, 3- or 4-pyridyl)-ethylamino, 3-(2-, 3- or 4-pyridyl)-propylamino, imidazolyl-lower alkylamino, for example 4-imidazolylmethylamino or 2-(4-imidazolyl)-ethylamino, indolyl-lower alkylamino, for example 3-indolylmethylamino or 2-(3-indolyl)-ethylamino, lower alkoxy, for example methoxy, ethoxy or tert.-butoxy, or by physiologically cleavable substituted alkoxy, for example pivaloyloxymethoxy, or also -Ile-His-, -Ile-Sta- or -Ala-Sta- C-terminally substituted by amino, lower alkylamino, for example methyl-, ethyl-, n-propyl- or n-butyl-amino, di-lower alkylamino, for example dimethylamino, hydroxy-lower alkylamino, for example 2-hydroxyethylamino or tris-(hydroxymethyl)-methylamino, or also by lower alkoxy, for example methoxy, ethoxy or tert.-butoxy, or by physiologically cleavable substituted alkoxy, for example pivaloyloxymethoxy, and to pharmaceutically acceptable salts of these compounds having salt-forming groups.

The invention relates especially to compounds of the formula I in which $R_1$ represents hydrogen, lower alkanoyl, for example formyl, acetyl, propionyl or pivaloyl, aminoalkanoyl, for example aminoacetyl, $\gamma$-aminobutyryl or 8-aminooctanoyl, lower alkoxycarbonylaminoalkanoyl, for example tert.-butoxycarbonylaminoacetyl, $\gamma$-tert.-butoxycarbonylaminobutyryl or 8-tert.-butoxycarbonylaminooctanoyl, benzyloxycarbonylamino-lower alkanoyl, for example $\gamma$-benzyloxycarbonylaminobutyryl or 8-benzyloxycarbonylaminooctanoyl, amino- or acylamino-lower alkanoylaminoacetyl, for example $\gamma$-aminobutyrylaminoacetyl, $\gamma$-tert.-butoxycarbonylaminobutyrylaminoacetyl or $\gamma$-benzyloxycarbonylaminobutyrylaminoacetyl, dihydroxy-carboxylower alkanoyl, for example $\alpha,\beta$-dihydroxy-$\beta$-carboxypropionyl, dihydroxy-lower alkoxycarbonyl-lower alkanoyl, for example $\alpha,\beta$-dihydroxy-$\beta$-methoxycarbonylpropionyl, esterified dihydroxy-lower alkoxycarbonyl-lower alkanoyl, for example $\alpha,\beta$-diacetoxy-$\beta$-methoxycarbonylpropionyl, hydroxycyclohexenylcarbonyl, for example 3,4,5-trihydroxycyclohex-1-enylcarbonyl, 2-(o,o-dichloroanilino)-phenylacetyl, 2-(o,o-dichloro-N-benzylanilino)-phenylacetyl, hydroxypyrrolidinylcarbonyl, for example 3- or 4-hydroxypyrrolidinyl-2-carbonyl, hydroxy-1-acylpyrrolidinylcarbonyl, for example 3- or 4-hydroxy-1-benzyloxycarbonylpyrrolidinyl-2-carbonyl, 5-oxopyrrolidinyl-2-carbonyl, lower alkoxycarbonyl, for example tert.-butoxycarbonyl, or phenylmethoxycarbonyl having one or two phenyl radicals which are optionally substituted by lower alkyl, for example methyl, lower alkoxy, for example methoxy, and/or by nitro, for example benzyloxycarbonyl, 4-nitrobenzyloxycarbonyl, diphenylmethoxycarbonyl or di-(4-methoxyphenyl)-methoxycarbonyl, $X_1$ and $X_2$ together represent -Phe-His- or -Phe-Phe- which are bonded N-terminally to $R_1$ and C-terminally to the group —$NR_2$—, $R_2$ represents hydrogen, $R_3$ represents isobutyl, $R_4$ represents hydroxy, $R_5$ represents isopropyl, n-octyl, cyclohexyl or phenyl, and $R_6$ represents amino, lower alkylamino, for example methyl-, ethyl- or n-butyl-amino, di-lower alkylamino, for example dimethylamino, hydroxy-lower alkylamino, for example 2-hydroxyethylamino or tris-(hydroxymethyl)methylamino, carboxyalkylamino, for example 4-carboxy-n-butylamino, 7-carboxy-n-heptylamino or 8-carboxy-n-octylamino, lower alkoxycarbonylalkylamino, for example 4-tert.-butoxycarbonyl-n-butylamino or 7-tert.-butoxycarbonyl-n-heptylamino, physiologically cleavable esterified carboxyalkylamino, for example 4-pivaloyloxymethoxycarbonyl-n-butylamino or 7-pivaloyloxymethoxycarbonyl-n-heptylamino, aminoalkylamino, for example 4-amino-n-butylamino or 8-amino-n-butylamino, hydroxy-lower alkylamino-lower alkylamino, for example 2-(2-hydroxyethylamino)-ethylamino, di-lower alkylamino-lower alkylamino, for example 2-dimethylaminoethylamino, 4-morpholinyl-lower alkylamino, for example 3-(4-morpholinyl)-propylamino, 2-oxo-1-pyrrolidinyl-lower alkylamino, for example 3-(2-oxo-1-pyrrolidinyl)-propylamino, or also -Ala- or -Ile- C-terminally substituted by amino, lower alkylamino, for example methylamino, ethylamino or n-butylamino, di-lower alkylamino, for example dimethylamino, hydroxy-lower alkylamino, for example 2-hydroxyethylamino, dicarbamoylmethylamino, hydroxy-lower alkylamino-lower alkylamino, for example 2-(2-hydroxyethylamino)-ethylamino, 4-morpholinyl-lower alkylamino, for example 2-(4-morpholinyl)-ethylamino, 3-carbamoylbenzylamino, 4-carbamoylmethyl-2-thiazolylamino, pyridyl-lower alkylamino, for example 2-pyridylmethylamino, 2-(2-pyridyl)-ethylamino or 3-(2-pyridyl)-propylamino, or imidazolyl-lower alkylamino, for example 2-(4-imidazolyl)-ethylamino or 2-(3-indolyl)-ethylamino, or also -Ile-His- or -Ile-Sta- C-terminally substituted by amino, or -Ala-Sta- C-terminally substituted by lower alkoxy, for example methoxy, and to pharmaceutically acceptable salts of these compounds having salt-forming groups.

The invention relates above all to compounds of the formula I in which $R_1$ represents hydrogen, acetyl, pivaloyl, γ-aminobutyryl, 8-aminooctanoyl, γ-tert.-butoxycarbonylaminobutyryl, 8-tert.-butoxycarbonylaminooctanoyl, γ-benzyloxycarbonylaminobutyryl, 8-benzyloxycarbonylaminooctanoyl, γ-aminobutyrylaminoacetyl, γ-tert.-butoxycarbonylaminobutyrylaminoacetyl, γ-benzyloxycarbonylaminobutyrylaminoacetyl, α,β-dihydroxy-β-carboxypropionyl, α,β-dihydroxy-β-methoxycarbonylpropionyl, 4-hydroxypyrrolidinyl-2-carbonyl, 1-benzyloxycarbonyl-4-hydroxypyrrolidinyl-2-carbonyl, 5-oxopyrrolidinyl-2-carbonyl, tert.-butoxycarbonyl or benzyloxycarbonyl, $X_1$ and $X_2$ together represent -Phe-His- bonded N-terminally to $R_1$ and C-terminally to the group —$NR_2$—, $R_2$ represents hydrogen, $R_3$ represents isobutyl, $R_4$ represents hydroxy, $R_5$ represents isopropyl, and $R_6$ represents amino, lower alkylamino, for example methylamino, ethylamino or n-butylamino, dimethylamino, 4-carboxy-n-butylamino, 7-carboxy-n-heptylamino, 4-tert.-butoxycarbonyl-n-butylamino, 7-tert.-butoxycarbonyl-n-heptylamino, 7-pivaloyloxymethoxycarbonyl-n-heptylamino, 3-(2-oxo-1-pyrrolidinyl)-propylamino, -Ala- C-terminally substituted by 2-(4-imidazolyl)-ethylamino or 2-(2-pyridyl)-ethylamino, -Ile-C-terminally substituted by dicarbamoylmethylamino, 3-carbamoylbenzylamino, 4-carbamoylmethyl-2-thiazolylamino, 2-(2-pyridyl)-ethylamino, 2-pyridylmethylamino or 2-(3-indolyl)-ethylamino, -Ile-His- or -Ile-Sta-C-terminally substituted by amino, or -Ala-Sta-C-terminally substituted by methoxy, and to pharmaceutically acceptable salts of these compounds having salt-forming groups.

The invention relates primarily to the compounds mentioned in the Examples and to their pharmaceutically acceptable salts.

The invention relates above all to the following compounds which are described in the Examples:

benzyloxycarbonyl-Phe-His-[5(S)-amimo-4(S)-hydroxy-2(S)-isopropyl-7-methyloctanoyl]-Ile-His-NH$_2$, benzyloxycarbonyl-Phe-Phe-[5(S)-amino-4(S)-hydroxy-2(S)-isopropyl-7-methyloctanoyl]-Ile-His-NH$_2$, H-Phe-His-[5(S)-amino-4(S)-hydroxy-2(S)-isopropyl-7-methyloctanoyl]-Ile-His-NH$_2$,

[(2S,4R)-4-hydroxypyrrolidinyl-2-carbonyl]-Phe-His-[5(S)-amino-4(S)-hydroxy-2(S)-isopropyl-7-methyloctanoyl]-Ile-His-NH$_2$,

[(2S) -5-oxopyrrolidinyl-2-carbonyl]-Phe-His-[5(S)-amino-4(S)-hydroxy-2(S)-isopropyl-7-methyloctanoyl]-Ile-His-NH$_2$, tert.-butoxycarbonyl-Phe-His-[5(S)-amino-4(S)-hydroxy-2(S)-isopropyl-7-methyloctanoyl]-Ala-Sta-OCH$_3$, benzyloxycarbonyl-Phe-His-[5(S)-amino-4(S)-hydroxy-2(S)-isopropyl-7-methyloctanoyl]-Ala-Sta-OCH$_3$, γ-benzyloxycarbonylaminobutyrylaminoacetyl-Phe-His-[5(S)-amino-4(S)-hydroxy-2(S)-isopropyl-7-methyloctanoyl]-Ile-His-NH$_2$, γ-aminobutyrylaminoacetyl-Phe-His-[5(S)-amino-4(S)-hydroxy-2(S)-isopropyl-7-methyloctanoyl]-Ile-His-NH$_2$, 8-aminooctanoyl-Phe-His-[5(S)-amino-4(S)-hydroxy-(2S)-isopropyl-7-methyloctanoyl]-Ile-His-NH$_2$, benzyloxycarbonyl-Phe-His-[5(S)-amino-4(S)-hydroxy-(2S)-isopropyl-7-methyloctanoyl]-Ile-dicarbamoylmethyl amide, benzyloxycarbonyl-Phe-His-[5(S)-amino-4(S)-hydroxy-2(S)-isopropyl-7-methyloctanoyl]-2-(3-carbamoyl-4-hydroxy-phenoxy)-ethyl amide, α-benzyloxycarbonylamino-α-methoxycarbonyl-acetyl-Phe-His-[5(S)-amino-4(S)-hydroxy-2(S)-isopropyl-7-methyloctanoyl]-3-(2-pyrrolidinon-1-yl)-propyl amide, benzyloxycarbonyl-Phe-His-[5(S)-amino-4(S)-hydroxy-2(S)-isopropyl-7-methyloctanoyl]-methyl amide, benzyloxycarbonyl-Phe-His-[5(S)-amino-4(S)-hydroxy-2(S)-isopropyl-7-methyloctanoyl]-4-[tris-(hydroxymethyl)-methylaminocarbonyl]-butyl amide, benzyloxycarbonyl-Glu(O-tert.-butyl)-His-[5(S)-amino-4(S)-hydroxy-2(S)-isopropyl-7-methyloctanoyl]-Ile-His-NH$_2$ and benzyloxycarbonyl-Phe-His-[5(S)-amino-4(S)-hydroxy-2(S)-isopropyl-7-methyloctanoyl]-carbamoyl-(3-methoxycarbonyl-2-hydroxy-1-isobutylpropyl-aminocarbonyl)-methyl amide.

Processes

The compounds of the formula I according to the invention and salts of such compounds having at least one salt-forming group are obtained according to processes that are known per se, for example as follows:

(a) a fragment of a compound of the formula I having a terminal carboxy group or a reactive acid derivative of that fragment is condensed with a fragment that is complementary to the compound of the formula I and has a free amino group or with a reactive derivative thereof having an activated amino group to form an amide bond, any free functional groups present in the reactants, with the exception of the groups participating in the reaction, optionally being in protected form, or (b) for the manufacture of a compound of the formula I in which R$_4$ represents hydroxy, the keto group in a compound of the formula

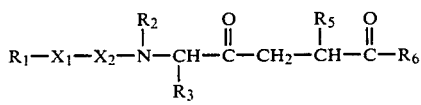

in which the substituents have the meanings mentioned and free functional groups, with the exception of the keto group participating in the reaction, are optionally in protected form, is reduced to a hydroxy group by reaction with a suitable reducing agent, or (c) for the manufacture of a compound of the formula I in which R$_4$ represents hydroxy, an aldehyde compound of the formula

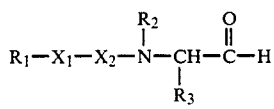

in which the substituents have the meanings mentioned and free functional groups, with the exception of the aldehyde group, are optionally in protected form, is reacted with an organometal compound of the formula

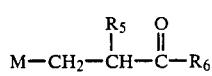

in which the substituents have the meanings mentioned and M represents a metal radical, and the resulting addition product is hydrolysed, or (d) a compound of the formula

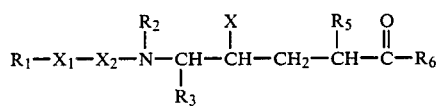

in which X represents a nucleofugal leaving group, the other substituents have the meanings given above and free functional groups are optionally in protected form, the substituent X is exchanged for R$_4$ with a reagent that introduces the substituent R$_4$ in nucleophilic form, or (e) for the manufacture of a compound of the formula I in which R$_6$ represents unsubstituted or substituted amino, in a compound of the formula

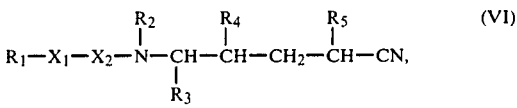

in which the substituents have the meanings mentioned, or in a compound of the formula

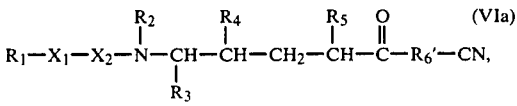

in which the group R$_6'$—CN represents the residue of a naturally occurring α-amino acid, or a di- or a tripeptide residue in each of which the terminal —COOH group has been replaced by —CN, and in which formula the other substituents have the meanings mentioned and any functional groups are optionally in protected form, the cyano group is converted into an unsubstituted or N-substituted carboxamido group, or (f) for the manufacture of a compound of the formula I in which R$_4$ represents free hydroxy, an epoxide of the formula

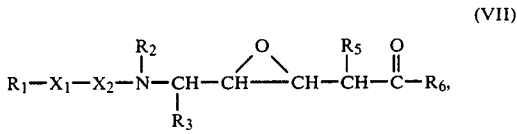

in which the substituents have the meanings mentioned and free functional groups are optionally in protected form, is reduced to the corresponding alcohol with a regioselective reducing agent, and, if desired, any protecting groups in a resulting compound are removed and/or, if desired, after carrying out one of the processes (a) - (f) mentioned above or any other process for the manufcture of a compound of the formula I, a resulting compound of the formula I having a salt-forming group is converted into its salt or a resulting salt is converted in the free compound or into a different salt and/or isomeric mixtures that may be obtained are separated and/or, in a resulting compound of the formula I, the configuration of a chiral carbon atom is reversed and/or a compound of the formula I according to the invention is converted into a different compound of the formula I according to the invention.

The invention relates also to the compounds other than compounds of the formula I, obtainable according to any one of the processes mentioned above (by-product), and to compounds of the formula I and salts thereof that have been manufactured by a process other than one of those mentioned hereinbefore.

Process (a)

(Production of an amide bond)

Fragments of a compound of the formula I having a terminal carboxy group that can be condensed with a fragment complementary to a compound of the formula I to form an amide bond are, for example, compounds of the formulae: $R_1$—OH, $R_1$—$X_1$—OH, $R_1$—$X_1$—$X_2$—OH,

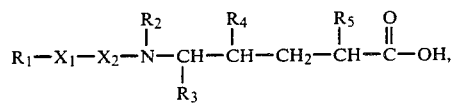

and, optionally,

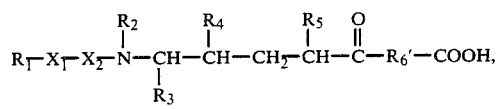

in which the group $R_6'$—COOH represents the residue of an α-amino acid or of a dipeptide or tripeptide as defined above for $R_6$, or the activated esters or reactive anhydrides derived from these compounds, and also reactive cyclic amides. The reactive acid derivatives can also be formed in situ.

Activated esters are especially esters that are unsaturated at the linking carbon atom of the esterifying radical, for example of the vinyl ester type, such as vinyl esters (obtainable, for example, by transesterification of a corresponding ester with vinyl acetate; activated vinyl esters method), carbamoylvinyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexyl carbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexyl carbodiimide; activated aryl esters method), cyanomethyl esters (obtainable, for example, by treatment of the corresponding acid with chloroacetonitrile in the presence of a base; cyanomethyl esters method), thio esters, especially phenylthio esters optionally substituted, for example, by nitro (obtainable, for example, by treatment of the corresponding acid with thiophenols that are optionally substituted, for example, by nitro, inter alia with the aid of the anhydride or carbodiimide method; activated thio esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide, 1-hydroxybenzotriazole or 3-hydroxy-3,4-dihydro-1,2,3-benzotriazin-4-one, for example according to the anhydride or carbodiimide method; activated N-hydroxyesters method).

Anhydrides of acids may be symmetric or preferably mixed anhydrides of these acids, for example, anhydrides with inorganic acids, such as acid halides, especially acid chlorides (obtainable, for example, by treating the corresponding acid with thionyl chloride, phosphorus pentachloride or oxalyl chloride; acid chloride method), azides (obtainable, for example, from a corresponding acid ester by way of the corresponding hydrazide and the treatment of the latter with nitrous acid; azide method), anhydrides with carbonic acid semi-esters, for example carbonic acid lower alkyl semi-esters (obtainable, for example, by treating the corresponding acid with chloroformic acid lower alkyl esters, or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (obtainable, for example, by treating the corresponding acid with phosphorus oxychloride; phosphorus oxychloride method), anhydrides with other phosphoric acid derivatives (for example those which can be obtained with phenyl-N-phenylphosphoramidochloridate) or with phosphorous acid derivatives, or anhydrides with organic acids, such as mixed anhydrides with organic carboxylic acids (obtainable, for example, by treating the corresponding acid with an optionally substituted lower alkanecarboxylic acid halide or phenyl-lower alkanecarboxylic acid halide, for example phenylacetic acid chloride, pivalic acid chloride or trifluoroacetic acid chloride; mixed carboxylic acid anhydrides method) or with organic sulphonic acids (obtainable, for example, by treating a salt, such as an alkali metal salt, of the corresponding acid with a suitable organic sulphonic acid halide, such as a lower alkanesulphonic acid chloride or arylsulphonic acid chloride, for example methane- or p-toluene-sulphonic acid chloride; mixed sulphonic acid anhydrides method), and symmetric anhydrides (obtainable, for example, by condensing the corresponding acid in the presence of a carbodiimide or of 1-diethylaminopropyne; symmetric anhydrides method).

Suitable cyclic amides are especially amides having five-membered diazacycles of aromatic character, such as amides with imidazoles, for example imidazole (obtainable, for example, by treating the corresponding acid with N,N'-carbonyldiimidazole; imidazole method), or pyrazole, for example 3,5-dimethylpyrazole (obtainable, for example, by way of the acid hydrazide by treatment with acetylacetone; pyrazolide method).

Fragments having a free amino group that are complementary to the compound of the formula I are, for example, depending on the meaning of $R_6$, ammonia, a primary or secondary amine, an α-amino acid, a dipeptide or a tripeptide having a free α-amino group, also compounds of the formula:

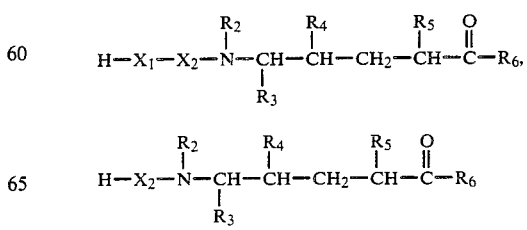

or

-continued

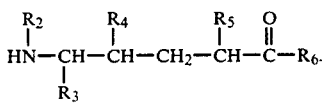

The amino group participating in the reaction in a fragment complementary to the compound of the formula I is preferably in free form, especially if the carboxy group reacting therewith is in reactive form; it can also, however, itself be derivatised, for example by reaction with a phosphite, such as diethylchlorophosphite, 1,2-phenylenechlorophosphite, ethyldichlorophosphite, ethylenechlorophosphite or tetraethylpyrophosphite. A derivative of such a complementary fragment having an amino group is, for example, also a carbamic acid halide or an isocyanate, the amino group participating in the reaction being substituted by halocarbonyl, for example chlorocarbonyl, or modified as the isocyanate group, it being possible in the latter case to obtain only compounds of the formula I that have a hydrogen atom at the nitrogen atom of the amide group formed by the reaction.

If the complementary fragment having an amino group is ammonia itself or an amine mono- or di-substituted by lower alkyl or aryl-lower alkyl then a corresponding urea compound also constitutes a reactive derivative. For example, on heating equimolar amounts of this urea compound and the component having a free carboxy group, corresponding compounds of the formula I are obtained, in some cases in good yields.

If the complementary fragment is dimethylamine then dimethylformamide is also a reactive derivative.

Functional groups in starting materials, the reaction of which is to be avoided, especially carboxy, amino, hydroxy and mercapto groups, can be protected by suitable protecting groups (conventional protecting groups) that are customarily used in the synthesis of peptide compounds and also of cephalosporins and penicillins. These protecting groups may already be present in the precursors and are intended to protect the functional groups in question against undesired side-reactions, such as acylation, etherification, esterification, oxidation, solvolysis, etc.. Protecting groups may, however, also be present in the end products. Compounds of the formula I having protected functional groups can have a higher metabolic stability than can the corresponding compounds having free functional groups.

The protection of functional groups by such protecting groups, the protecting groups themselves and deprotection reactions are described, for example, in standard works, such as in J. F. W. McOmie, "Protective Groups in Organic Chemistry", Plenum Press, London and New York 1973, in Th. W. Greene, "Protective Groups in Organic Synthesis", Wiley, N.Y. 1981, in "The Peptides", volume 3 (edited by E. Gross and J. Meienhofer), Academic Press, London and New York 1981, and in "Methoden der organischen Chemie", Houben-Weyl, 4th edition, vol. 15/1, Georg Thieme Verlag, Stuttgart 1974.

A carboxy group is protected, for example, in the form of an ester group that is selectively cleavable under mild conditions. A carboxy group protected in esterified form is esterified especially by a lower alkyl group that is branched in the 1-position of the lower alkyl group or substituted by suitable substituents in the 1- or 2-position of the lower alkyl group.

A protected carboxy group esterified by a lower alkyl group that is branched in the 1-position of the lower alkyl group is, for example, tert.-lower alkoxycarbonyl, for example tert.-butoxycarbonyl, arylmethoxycarbonyl having one or two aryl radicals in which aryl is unsubstituted phenyl or phenyl mono-, di- or tri-substituted by lower alkyl, for example tert.-lower alkyl, such as tert.-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di-(4-methoxyphenyl)-methoxycarbonyl.

A protected carboxy group esterified by a lower alkyl group that is substituted by suitable substituents in the 1- or 2-position of the lower alkyl group is, for example, 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, and also 2-tri-lower alkylsilyl-lower alkoxycarbonyl, for example 2-trimethylsilylethoxycarbonyl.

A carboxy group can also be protected as an organic silyloxycarbonyl group. An organic silyloxycarbonyl group is, for example, a tri-lower alkylsilyloxycarbonyl group, for example trimethylsilyloxycarbonyl. The silicon atom of the silyloxycarbonyl group may also be substituted by two lower alkyl groups, for example methyl groups, and by the amino group or the carboxy group of a second molecule of the formula I. Compounds having such protecting groups can be manufactured, for example, with dimethylchlorosilane as the silylating agent.

A protected carboxy group is preferably tert.-lower alkoxycarbonyl, for example tert.-butoxycarbonyl, benzyloxycarbonyl, 4-nitrobenzyloxycarbonyl and diphenylmethoxycarbonyl.

An amino group can be protected, for example, in the form of an acylamino, arylmethylamino, etherified mercaptoamino or silylamino group or in the form of an azido group.

In a corresponding acylamino group, acyl is, for example, the acyl radical of an organic carboxylic acid having, for example, up to 18 carbon atoms, especially of a lower alkanecarboxylic acid that is optionally substituted, for example by halogen or aryl, or of benzoic acid that is optionally substituted, for example by halogen, lower alkoxy or nitro, or preferably of a carbonic acid semi-ester. Such acyl groups are, for example, lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloro-acetyl, benzoyl optionally substituted, for example, by halogen, lower alkoxy or nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, for example tert.-lower alkoxycarbonyl, such as tert.-butoxycarbonyl, arylmethoxycarbonyl having one or two aryl radicals which are phenyl optionally mono-or poly-substituted, for example, by lower alkyl, for example tert.-lower alkyl, such as tert.-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl or di-(4-methoxyphenyl)-methoxycarbonyl, aroylmethoxycarbonyl, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-tri-lower alkylsilyl-lower alkoxycarbonyl, for example 2-trimethylsilylethoxycarbonyl, or 2-triarylsilyl-lower alkoxycarbonyl, for example 2-triphenylsilylethoxycarbonyl.

An arylmethylamino group is, for example, mono-, di- or especially tri-phenylmethylamino, for example benzyl-, diphenylmethyl- or trityl-amino.

In an etherified mercaptoamino group, the etherified mercapto group is especially substituted arylthio, for example 4-nitrophenylthio.

A silylamino group is, for example, a tri-lower alkylsilylamino group, for example trimethylsilylamino. The silicon atom of the silylamino group can also be substituted by only two lower alkyl groups, for example methyl groups, and by the amino group or carboxy group of a second molecule of the formula I. Compounds having such protecting groups can be manufactured, for example, with dimethylchlorosilane as the silylating agent.

Preferred amino-protecting groups are acyl radicals of carbonic acid semi-esters, especially tert.-butoxycarbonyl, optionally substituted benzyloxycarbonyl, for example 4-nitrobenzyloxycarbonyl, diphenylmethoxycarbonyl, 2-halo-lower alkoxycarbonyl, for example 2,2,2-trichloroethoxycarbonyl, and also trityl or formyl.

A hydroxy group can be protected, for example, by an acyl group, for example by halo-substituted, for example chloro-substituted, lower alkanoyl, for example 2,2-dichloroacetyl, or especially by an acyl radical of a carbonic acid semi-ester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A hydroxy group can also be protected by tri-lower alkylsilyl, for example trimethylsilyl or dimethyl-tert.-butylsilyl, a readily removable alkyl group, such as tert.-lower alkyl, for example tert.-butyl, an oxa- or a thia-aliphatic or -cycloaliphatic hydrocarbon radical, for example 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, for example 2-tetrahydrofuryl or 2-tetrahydropyranyl, or a corresponding thia analogue, or also by 1-phenyl-lower alkyl, for example benzyl, diphenylmethyl or trityl, it being possible for the phenyl radicals to be substituted, for example, by halogen, for example chlorine, lower alkoxy, for example methoxy, and/or by nitro.

Two adjacent hydroxy groups can be protected, for example, by a preferably substituted methylene group, for example by lower alkylidene, for example isopropylidene, cycloalkylidene, for example cyclohexylidene, or benzylidene.

A mercapto group, such as, for example, in cysteine, can be protected especially by S-alkylation with optionally substituted alkyl radicals, thioacetal formation, S-acylation or by the formation of asymmetric disulphide groupings. Preferred mercapto-protecting groups are, for example, benzyl optionally substituted in the phenyl radical, for example by methoxy or nitro, such as 4-methoxybenzyl, diphenylmethyl optionally substituted in the phenyl radical, for example by methoxy, such as 4,4'-dimethoxydiphenylmethyl, triphenylmethyl, trimethylsilyl, benzylthiomethyl, tetrahydropyranyl, acylaminomethyl, benzoyl, benzyloxycarbonyl or lower alkylaminocarbonyl, such as ethylaminocarbonyl.

The condensation for the production of the amide bond can be carried out in a manner known per se, for example as described in standard works, such as Houben-Weyl, "Methoden der organischen Chemie", 4th edition, vol. 15/II, Georg Thieme Verlag, Stuttgart 1974, "The Peptides" (edited by E. Gross and J. Meienhofer), volumes 1 and 2, Academic Press, London and New York 1979/1980, or M. Bodanszky, "Principles of Peptide Synthesis", Springer-Verlag, Berlin 1984.

The condensation can be carried out in the presence of one of the customary condensation agents. Customary condensation agents are, for example, carbodiimides, for example diethyl, dipropyl or N-ethyl-N'-(3-dimethylaminopropyl) carbodiimide or especially dicyclohexyl carbodiimide, also suitable carbonyl compounds, for example carbonyldiimidazole, 1,2-oxazolium compounds, for example 2-ethyl-5-phenyl-1,2-oxazolium 3'-sulphonate and 2-tert.-butyl-5-methylisoxazolium perchlorate, or a suitable acylamino compound, for example 2-ethoxy-1-ethoxycarbonyl-1,2-dihydroquinoline, or activated phosphates, for example diphenylphosphoryl azide, diethylphosphoryl cyanide or phenyl-N-phenylphosphoramidochloridate.

If desired, an organic base is added, for example a tri-lower alkylamine having voluminous radicals, for example ethyldiisopropylamine, or a heterocyclic base, for example pyridine, 4-dimethylaminopyridine or preferably N-methylmorpholine.

The condensation of acid anhydrides with amines can be effected, for example, in the presence of alkali metal carbonates, for example alkali metal carbonates or bicarbonates, such as sodium or potassium carbonate or sodium or potassium bicarbonate (customarily together with a sulphate).

The condensation is preferably carried out in an inert, polar, aprotic, preferably anhydrous solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in mixtures thereof, optionally at reduced or elevated temperature, for example within a temperature range of from approximately −40° C. to approximately +100° C., preferably from approximately −10° C. to approximately +50° C., and optionally under an inert gas atmosphere, for example a nitrogen atmosphere.

Reactive acid derivatives can also be formed in situ. Thus, for example, N,N'-disubstituted amidino esters can be formed in situ by reacting the mixture of the fragment having a free carboxy group and the complementary fragment having an amino group in the presence of a suitable disubstituted carbodiimide, for example dicyclohexyl carbodiimide. Amino or amido esters of such acids can also be formed in the presence of the amino component to be acylated, by reacting the mixture of the corresponding acid and amino starting materials in the presence of a disubstituted carbodiimide, for example dicyclohexyl carbodiimide, and an N-hydroxylamine or N-hydroxyamide, for example N-hydroxybenzotriazole, N-hydroxysuccinimide or N-hydroxy-5-norbornene-2,3-dicarboxylic acid imide, optionally in the presence of a suitable base, for example 4-dimethylaminopyridine, N-methylmorpholine or ethyldiisopropylamine.

Process (b)

(Reduction of a keto group)

In a starting material of the formula II functional groups, with the exception of the keto group to be reduced, are optionally protected by one of the protecting groups mentioned under process (a).

For the reduction of the keto group in a compound of the formula II there are suitable those reducing agents which, under the reaction conditions of the process, reduce an isolated keto group selectively or more rapidly than the amide groups present in compounds of the formula I.

There are to be mentioned, especially, suitable borohydrides, such as alkali metal borohydrides, especially sodium borohydride, lithium borohydride or sodium cyanoborohydride, or suitable aluminium hydrides, such as alkali metal lower alkoxyaluminium hydrides having voluminous radicals, for example lithium tris-tert.-butoxyaluminium hydride.

The reduction can also be carried out with hydrogen in the presence of suitable heavy metal catalysts, for example Raney nickel or platinum or palladium catalysts, for example platinum on active carbon or palladium on active carbon, or according to the Meerwein-Pondorf-Verley method with the aid of aluminium alkoxides, preferably aluminium 2-propoxide or 2-ethoxide.

The reduction can preferably be carried out with stoichiometric amounts or, if necessary in the case of simultaneous side-reactions, for example with the solvent, which are, of course, undesired, with a reasonably proportioned excess of the reducing agent, in an inert solvent at temperatures of from $-80°$ C. to the boiling point of the solvent, preferably from $-20°$ C. to $+100°$ C., if necessary under a protective gas, for example nitrogen or argon.

Suitable solvents when using sodium borohydride are polar, protic solvents, for example methanol, ethanol or isopropanol, and, when using the other reducing agents, the polar, aprotic solvents mentioned under process (a), for example tetrahydrofuran.

Process (c)

In a starting material of the formula III functional groups, with the exception of the aldehyde group, are optionally protected by the protecting groups mentioned under process (a). Functional groups present in a compound of the formula IV are likewise optionally protected.

In a compound of the formula IV a metal radical —M is, for example, —Li or —MgHal, for example —MgCl, —MgBr or —MgI.

The reaction of a compound of the formula III with a compound of the formula IV is effected in customary manner in an anhydrous, inert, aprotic solvent, for example in an ether, such as diethyl ether or tetrahydrofuran, or a hydrocarbon, such as benzene or toluene, or mixtures thereof, optionally while cooling, especially after the beginning of the reaction, for example to approximately $-30°$ C., or while heating, for example to the boiling temperature of the reaction mixture, optionally under an inert gas atmosphere, for example a nitrogen atmosphere. A preferred form of the process is the reaction of the aldehyde of the formula III with an excess of the lithium compound of the formula IV.

The hydrolysis of the addition product is effected with solvents that yield $H^+$ ions, for example water (ice-water mixture) or dilute, aqueous acids, for example dilute mineral acids, such as dilute, aqueous sulphuric acid, or dilute organic acids, for example dilute, aqueous acetic acid.

The reaction of a compound of the formula III can also be effected with a compound of the formula IV that has been manufactured in situ and that is obtained, for example, from the corresponding halide, for example chloride, by reaction with a metallating agent, for example magnesium, lithium or tert.-butyllithium.

Process (d)

(Nucleophilic substitution)

In a starting material of the formula V functional groups are optionally protected by the protecting groups mentioned under process (a).

In a compound of the formula V the nucleofugal leaving group X is especially hydroxy esterified by a strong inorganic or organic acid, such as a mineral acid, for example a hydrohalic acid, such as hydrochloric, hydrobromic or hydriodic acid, or also sulphuric acid or halosulphuric acid, for example fluorosulphuric acid, or hydroxy esterified by a strong organic sulphonic acid, such as a lower alkanesulphonic acid optionally substituted, for example, by halogen, such as fluorine, or an aromatic sulphonic acid, for example a benzenesulphonic acid optionally substituted by lower alkyl, such as methyl, halogen, such as bromine, and/or by nitro, for example a methanesulphonic, trifluoromethanesulphonic or p-toluene-sulphonic acid, or hydroxy esterified by hydrazoic acid.

A reagent that introduces the substituent $R_4$ in nucleophilic form is, depending on the meaning of $R_4$, a hydroxide-containing base, for example sodium or potassium hydroxide ($R_4=OH$), an alcohol, for example methanol or ethanol ($R_4=$ etherified hydroxy) or the salt of a carboxylic acid, for example silver acetate ($R_4=$ esterified hydroxy).

The reaction conditions are preferably so chosen that the reaction proceeds substantially as a second-order nucleophilic substitution ($S_N2$). For example, a compound of the formula V in which X represents a leaving group having high polarisability of the electron shell, for example iodine, can be reacted in a polar aprotic solvent, for example acetone, acetonitrile, nitromethane, dimethyl sulphoxide or dimethylformamide, with the silver salt of a carboxylic acid, for example silver acetate. The reaction with a hydroxide-containing base is preferably carried out in water to which there has optionally been added as solution aid an organic solvent, for example ethanol, tetrahydrofuran or acetone, and the reaction with an alcohol preferably in an excess of that alcohol, optionally in the presence of one of the polar aprotic solvents mentioned above. The substitution reaction is carried out optionally at reduced or elevated temperature, for example within a temperature range of from approximately −40° C. to approximately +100° C., preferably from approximately −10° C. to approximately +50° C., and optionally under an inert gas atmosphere, for example a nitrogen atmosphere.

Process (e)

(Conversion of a cyano group into an amide group)

In a starting material of the formula VI or VIa functional groups are optionally protected by the protecting groups mentioned under process (a).

The conversion of a compound of the formula VI or VIa into a compound of the formula I can be effected by partial hydrolysis, by a Ritter reaction or by way of carboxylic acid ester imide salts.

The conditions of the hydrolysis of a compound of the formula VI or VIa can be so chosen that the reaction remains at the amide stage. For this purpose, the nitrile of the formula VI or VIa is hydrolysed with acid, it being possible, depending on the thermal sensitivity of the substituents present in a compound of the formula VI or VIa, to choose especially between 80% sulphuric acid (with heating), polyphosphoric acid (at 110°–150°), hydrogen bromide/glacial acetic acid or formic acid (room temperature), hydrogen chloride gas in ethereal solution followed by water or aqueous hydrochloric acid, or boron halides, for example boron trifluoride/acetic acid complex, followed by water. In some cases, alkaline hydrolysis, especially according to the Radziszewski method, with hydrogen peroxide in the presence of alkali metal hydroxides at moderate temperature, for example room temperature, is also successful.

N-substituted amides can successfully be manufactured from nitriles of the formula VI or VIa with the aid of the Ritter reaction. For this purpose, the nitriles are reacted in the presence of a strong acid, for example 85–90% sulphuric acid, or also polyphosphoric acid, hydrofluoric acid, formic acid, boron trifluoride or other Lewis acids but not aluminium chloride, with compounds that are capable of forming carbenium ions in the acidic medium, that is to say, for example, with olefins, such as propylene, or alcohols, such as benzyl alcohol, in most cases without solvent or, for example, in glacial acetic acid.

In a variant of the Ritter reaction, a nitrile of the formula VI or VIa is reacted with an olefin and mercury(II) nitrate and the organomercury compound is subsequently reduced with sodium borohydride to an N-substituted compound of the formula I.

The carboxylic acid ester imides are obtained, for example, by the acid-catalysed addition of alcohols to the nitriles, preferably in the presence of hydrogen chloride. The amides are obtained from the resulting ester imide salts by thermal rearrangement at temperatures above approximately 80° C.

Process (f)

(Reduction of the epoxide)

In a starting material of the formula VII functional groups are optionally protected by the protecting groups mentioned under process (a).

It is possible to use those reducing agents which, under the reaction conditions of the process, reduce the epoxy group selectively or more rapidly than the amide groups present and which open the epoxide in such a manner that a sufficient, and as large as possible, proportion of the reaction products carries the newly formed hydroxy group in the position corresponding to that of the formula I. Examples of such selective reducing agents are lithium borohydride or sodium cyanoborohydride/boron trifluoride etherate. Using the last-mentioned reagent the reaction can be carried out, for example, by adding a solution of boron trifluoride etherate, $BF_3 \cdot O(C_2H_5)_2$, in tetrahydrofuran to 1 mole of the compound of the formula VII and an excess, for example 1.4–3 moles, of sodium cyanoborohydride in tetrahydrofuran at elevated temperature, for example under reflux, in such a manner that the pH of the reaction solution is maintained close to the turning point of the indicator bromocresol green which has also been added. The reduction with lithium borohydride is preferably carried out in an ether, for example tetrahydrofuran, 1,2-dimethoxyethane or diethylene glycol dimethyl ether, at temperatures of from room temperature to the reflux temperature.

Subsequent operations

In a resulting compound of the formula I in which $R_1$, $X_1$, $X_2$, $R_2$, $R_3$, $R_4$ and $R_5$ have the meanings mentioned and $R_6$ represents the residue of an amino acid or of a dipeptide or tripeptide having a terminal carboxamide, carboxy or carboxylic acid ester group, the terminal carboxamide group can be substituted, the carboxy group present in free or reactive form can be esterified, and an esterified carboxy group can be converted into a carboxamide group.

Substitution of a terminal carboxamide group or another amino group is effected, for example, by alkylation.

Suitable agents for alkylating a terminal carboxamide group in a compound of the formula I are, for example, diazo compounds, for example diazomethane. Diazomethane can be decomposed in an inert solvent and the free methylene formed in so doing reacts with the carboxamide group in the compound of the formula I. The decomposition of diazomethane is preferably effected catalytically, for example in the presence of a noble metal in finely divided form, for example copper, or a noble metal salt, for example copper(I) chloride or copper(II) sulphate.

Further alkylating agents are those mentioned in German Offenlegungsschrift No. 2 331 133, for example alkyl halides, sulpho acid esters, Meerwein salts or 1-substituted 3-aryltriazenes, which can be reacted with a compound of the formula I having a terminal carboxamide group under the conditions described in that specification.

For the esterification of a terminal carboxy group in a compound of the formula I the free acid can be used or the free acid can be converted into one of the reactive derivatives mentioned under process (a) and reacted with an alcohol, or the free acid or a reactive salt, for example the caesium salt, can be reacted with a reactive derivative of an alcohol. For example, the caesium salt of a carboxylic acid can be reacted with the halide of an alcohol.

The esterification of a terminal carboxy group can be effected with the alkylating agents mentioned above for the substitution of the carboxamide group and under the same reaction conditions, for example with diazomethane, alkyl halides, sulphonic acid esters, Meerwein salts, 1-substituted 3-aryltriazenes, etc..

In a resulting compound of the formula I a terminal esterified carboxy group can be converted into an optionally substituted carboxamide group by aminolysis with ammonia or a primary or secondary amine.

The aminolysis can be effected under the reaction conditions mentioned for such reactions in the "Organikum", latest edition, VEB Deutscher Verlag der Wissenschaften, Berlin (East).

In a resulting compound of the formula I in which the substituents have the meanings mentioned and at least one free hydroxy group is present and the other functional groups are optionally in protected form, the free hydroxy group, for example the hydroxy group R$_4$, can be etherified or esterified.

The etherification of this hydroxy group can be effected with the alkylating agents mentioned above and under the same reaction conditions, for example with diazomethane, alkyl halides, sulphonic acid esters, Meerwein salts, 1-substituted 3-aryltriazenes, etc..

The esterification of the free hydroxy group can be effected with the customary acylating agents and the customary reaction conditions indicated in the "Organikum", for example with acetic anhydride.

The mentioned alkylating reactions, etherifications, esterifications, etc. can also be carried out in corresponding manner in a starting material instead of in the end product.

In a resulting compound of the formula I in which one or more functional groups are protected, these groups, for example carboxy, amino, hydroxy and/or mercapto groups, can be freed in a manner known per se, optionally in stages or simultaneously, by means of solvolysis, especially hydrolysis, optionally enzymatic hydrolysis, alcoholysis or acidolysis, or by means of reduction, especially hydrogenolysis, or chemical reduction. The removal of protecting groups is described in the standard works mentioned hereinbefore in the section "protecting groups".

For example, protected carboxy, for example tert.-lower alkoxycarbonyl, lower alkoxycarbonyl substituted in the 2-position by an organic silyl group or in the 1-position by lower alkoxy or lower alkylthio, or optionally substituted diphenylmethoxycarbonyl, can be converted into free carboxy, for example, by treatment with a suitable acid, such as formic acid or trifluoroacetic acid, optionally with the addition of a nucleophilic compound, such as phenol or anisole. Optionally substituted benzyloxycarbonyl can be freed, for example, by means of hydrogenolysis, that is to say by treatment with hydrogen in the presence of a metallic hydrogenation catalyst, such as a palladium catalyst. Suitably substituted benzyloxycarbonyl, such as 4-nitrobenzyloxycarbonyl, can also be converted into free carboxy by reduction, for example by treatment with an alkali metal dithionite, for example sodium dithionite, or with a reducing metal, for example zinc, or a reducing metal salt, such as a chromium(II) salt, for example chromium(II) chloride, customarily in the presence of a hydrogen-yielding agent that together with the metal is capable of producing nascent hydrogen, such as an acid, especially a suitable carboxylic acid, such as an optionally substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or an alcohol or thiol, with water preferably being added. It is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxy by treatment with a reducing metal or a reducing metal salt, as described above. Aroylmethoxycarbonyl can also be cleaved by treatment with a nucleophilic, preferably salt-forming, reagent, such as sodium thiophenolate or sodium iodide. 2-tri-lower alkylsilyl-lower alkoxycarbonyl can also be converted into free carboxy by treatment with a salt of hydrofluoric acid yielding the fluoride anion, such as an alkali metal fluoride, for example sodium or potassium fluoride, optionally in the presence of a macrocyclic polyether ("Crown ether"), or with a fluoride of an organic quaternary base, such as tetralower alkylammonium fluoride or tri-lower alkylarylammonium fluoride, for example tetraethylammonium fluoride or tetrabutylammonium fluoride, in the presence of an aprotic, polar solvent, such as dimethyl sulphoxide or N,N-dimethylacetamide. Carboxy esterified by an organic silyl group, such as tri-lower alkylsilyl, for example trimethylsilyl, can be freed in customary manner by solvolysis, for example by treatment with water, an alcohol or an acid, or also a fluoride, as described above. Esterified carboxy can also be cleaved enzymatically, for example esterified arginine or lysine, such as lysine methyl ester, can be cleaved by means of trypsin.

A protected amino group is freed in a manner known per se and, depending on the nature of the protecting groups, by various methods, but preferably by solvolysis or reduction. 2-halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable reducing agent, such as zinc, in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionite, for example sodium dithionite. Optionally substituted diphenylmethoxycarbonylamino, tert.-lower alkoxycarbonylamino or 2-tri-lower alkylsilyl-lower alkoxycarbonylamino can be freed by treatment with a suitable acid, for example formic acid or trifluoroacetic acid, optionally substituted benzyloxycarbonylamino can be freed, for example, by hydrogenolysis, i.e. by treatment with hydrogen in the presence of a suitable hydrogenation catalyst, such as a palladium catalyst, optionally substituted triarylmethylamino or formylamino can be freed, for example, by treatment with an acid, such as a mineral acid, for example hydrochloric acid, or an organic acid, for example formic acid, acetic acid or trifluoroacetic acid, optionally in the presence of water, and an amino group protected by an organic silyl group can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea and by subsequent solvolysis, such as alcoholysis or hydrolysis, of the resulting condensation product. An amino group protected by 2-tri-lower alkylsilyl-lower alkoxycarbonyl can also be converted into the free amino group by treatment with a salt of hydrofluoric acid yielding fluoride anions, as indicated above in connection with the freeing of a correspondingly protected carboxy group. Silyl, such as trimethylsilyl, that is bonded directly to a hetero atom, such as nitrogen, can also be removed by means of fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, or also by treatment with zinc in the presence of an acid, such as acetic acid. The catalytic hydrogenation is preferably carried out in an inert solvent, such as a halogenated hydrocarbon, for example methylene chloride, or alternatively in water or a mixture of water and an organic solvent, such as an alcohol or dioxan, at approximately from 20° C. to 25° C., or alternatively while cooling or heating.

A hydroxy or mercapto group protected by a suitable acyl group, an organic silyl group or by optionally substituted 1-phenyl-lower alkyl is freed analogously to a correspondingly protected amino group. A hydroxy or mercapto group protected by 2,2-dichloroacetyl is freed, for example, by basic hydrolysis, while a hydroxy or mercapto group protected by tert.-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Two hydroxy groups that are protected together by means of a preferably substituted methylene group, such as by lower alkylidene, for example isopropylidene, cycloalkylidene, for example cyclohexylidene, or benzylidene, can be freed by acid solvolysis, especially in the presence of a mineral acid or a strong organic acid.

Salts of compounds of the formula I having salt-forming groups can be manufactured in a manner known per se. For example, salts of compounds of the formula I having acidic groups can be formed, for example, by treatment with metal compounds, such as alkali metal salts of suitable organic carboxylic acids, for example the sodium salt of 2-ethylhexanoic acid, or with inorganic alkali metal or alkaline earth metal salts, for example sodium bicarbonate, or with ammonia or a suitable organic amine, preferably stoichiometric amounts or only a small excess of the salt-forming agent being used. Acid addition salts of compounds of the formula I are obtained in customary manner, for example by treatment with an acid or a suitable anion exchange reagent. Internal salts of compounds of the formula I that contain, for example, a free carboxy group and a free amino group can be formed, for example, by neutralising salts, such as acid addition salts, to the isoelectric point, for example with weak bases, or by treatment with ion exchangers.

Salts can be converted in customary manner into the free compounds: metal and ammonium salts, for example, by treatment with suitable acids, and acid addition salts, for example, by treatment with a suitable basic agent.

Stereoisomeric mixtures, especially diastereoisomeric mixtures, can be separated into the individual isomers in a manner known per se, for example by fractional crystallisation, chromatography, etc..

Racemates can be split in a manner known per se, for example after converting the optical antipodes into diastereoisomers, for example by reaction with optically active acids or bases.

At individual chirality centres in a compound of the formula I, for example at the CH—$R_4$ C-atom, the configuration can be deliberately reversed. For example, the configuration at the CH—$R_4$ C-atom can be reversed by second order nucleophilic substitution according to process d) after converting the hydroxy group into a leaving group X and reaction with a reagent that introduces the substituent $R_4$.

The invention relates also to those forms of the process in which a compound obtainable as intermediate at any stage is used as starting material and the remaining steps are carried out or in which the process is interrupted at any stage or in which a compound obtainable in accordance with the process according to the invention is produced under the process conditions and further processed in situ.

Pharmaceutical preparations

The pharmacologically acceptable compounds of the present invention can be used, for example, for the manufacture of pharmaceutical preparations that contain an effective amount of the active ingredient together or in admixture with a significant amount of inorganic or organic, solid or liquid, pharmaceutically acceptable carriers.

The pharmaceutical preparations according to the invention are those for enteral, such as nasal, rectal or oral, administration or for parenteral, such as intramuscular or intravenous, administration to warm-blooded animals (humans and animals), which contain an effective dose of the pharmacological active ingredient on its own or together with a significant amount of a pharmaceutically acceptable carrier. The dosage of the active ingredient depends on the species, body weight, age and individual condition of the warm-blooded animal, on the disease to be treated and also on the mode of administration.

The dosages to be administered to warm-blooded animals, for example humans, of approximately 70 kg body weight are from approximately 3 mg to approximately 3 g, preferably from approximately 10 mg to approximately 1 g, for example approximately 300 mg per person per day, preferably distributed over from 1 to 3 single doses which may, for example, be of equal size. Children usually receive half the adult dose.

The novel pharmaceutical preparations contain from approximately 1% to approximately 95%, preferably from approximately 20% to approximately 90%, active ingredient. Pharmaceutical preparations according to the invention may, for example, be in dosage unit form, such as ampoules, phials, suppositories, dra ees, tablets or capsules.

The pharmaceutical preparations of the present invention are produced in a manner known per se, for example by means of conventional dissolving, lyophilising, mixing, granulating or confectioning processes.

There are preferably used solutions of the active ingredient, and also suspensions, especially isotonic aqueous solutions or suspensions, it being possible, for example in the case of lyophilised preparations which contain the active ingredient on its own or together with a carrier, for example mannitol, to prepare these before use. The pharmaceutical preparations may be sterilised and/or contain adjuncts, for example preservatives, stabilisers, wetting agents and/or emulsifiers, solubilisers, salts for regulating the osmostic pressure and/or buffers, and are prepared in a manner known per se, for example by means of conventional dissolving or lyophilising processes. The solutions or suspensions mentioned may contain substances that increase the viscosity, such as sodium carboxymethylcellulose, carboxymethylcellulose, dextran, polyvinylpyrrolidone or gelatine.

Suspensions in oil contain as oily component the vegetable, synthetic or semi-synthetic oils customary for injection purposes. There may be mentioned as such especially liquid fatty acid esters that contain as acid component a long-chained fatty acid having from 8 to 22, especially from 12 to 22, carbon atoms, such as, for example, lauric acid, tridecylic acid, myristic acid, pentadecylic acid, palmitic acid, margaric acid, stearic acid, arachidic acid, behenic acid, or corresponding unsaturated acids, such as, for example, oleic acid, elaidic acid, erucic acid, brassidic acid or linoleic acid. The alcohol component of these fatty acid esters has at most 6 carbon atoms and is a mono- or polyhydric, for example mono-, di- or tri-hydric, alcohol, for example methanol, ethanol, propanol, butanol or pentanol or their isomers, but above all glycol or glycerine. There may therefore be mentioned by way of example as fatty acid esters: ethyl oleate, isopropyl myristate, isopropyl palmitate, "Labrafil M 2735" (polyoxyethylene glycerine trioleate manufactured by Gattefossé, Paris), "Myglyol 812" (triglyceride of saturated fatty acids of chain length $C_8$ to C12, manufactured by Chemische Werke Witten/-Ruhr, Germany), but especially vegetable oils such as cotton seed oil, almond oil, olive oil, castor oil, sesame oil, soya bean oil and, above all, groundnut oil.

The manufacture of the injection preparations is effected in customary manner under sterile conditions, as is the introduction thereof into ampoules or phials and the sealing of the containers.

Pharmaceutical preparations for oral administration can be obtained by combining the active ingredient with solid carriers, optionally granulating a resulting mixture and, if desired or necessary after the addition of suitable adjuncts, processing the mixture or granulate into tablets or dragées cores. They can also be incorporated into plastics carriers which release the active ingredients, or allow them to diffuse, in a controlled manner.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that may be resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

Starting materials

The present invention relates also to novel starting materials and/or intermediates and to processes for the manufacture thereof. The starting materials and the reaction conditions are preferably so chosen that the compounds mentioned as being preferred are obtained.

The starting materials for carrying out process (a) are known or, if novel, can be manufactured according to processes that are known per se, for example from the relevant amino acids or di- or tri-peptide residues by condensation in a manner analogous to that of process (a) described hereinbefore.

For example, a compound of the formula

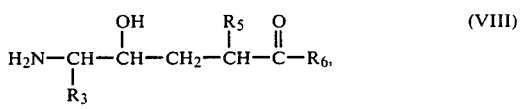

in which $R_3$, $R_5$ and $R_6$ have the meanings mentioned under formula I, can be manufactured by converting a compound of the formula

in which $R_3$ has the meanings mentioned and $Z_1$ is an amino-protecting group, with a sulphur-ylide compound into an epoxide of the formula

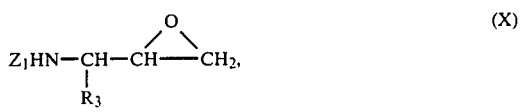

in which $R_3$ and $Z_1$ have the meanings mentioned, and, optionally after separating the isomers, reacting the resulting compound (X) with a reagent that introduces a nucleofugal leaving group X, and reacting the resulting compound of the formula

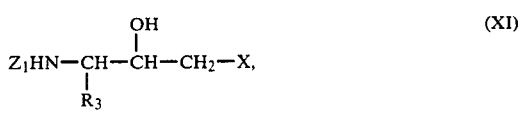

in which $R_3$ and $Z_1$ have the meanings mentioned and X is a nucleofugal leaving group, with a carbonyl compound of the formula

in which each of the radicals $R_a$ and $R_b$, independently of the other, represents hydrogen, lower alkyl, aryl or aryl-lower alkyl, $R_a$ and $R_b$ together represent optionally bridged alkylidene having from 4 to 12 carbon atoms, or with a reactive derivative of that carbonyl compound, in the presence of an acidic reagent, and reacting the resulting compound of the formula

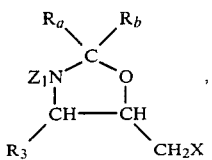

in which the substituents have the meanings mentioned, with a carboxylic acid ester salt of the formula

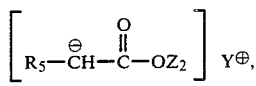

is a carboxy-protecting group and $Y^\oplus$ is a cation, for example an alkali metal ion, for example the sodium, or preferably the lithium, ion, and, in a resulting compound of the formula

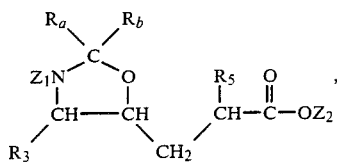

in which the substituents have the meanings mentioned, removing the carboxy-protecting group $Z_2$ and/or separating a resulting isomeric mixture into the individual isomers, and, depending on the meaning of the radical $R_6$ to be introduced, amidating, esterifying or substituting by a C-terminally optionally amidated or esterified residue of an amino acid or of a di- or tri-peptide the resulting compound having a free carboxy group ($Z_2=H$), and, in a resulting compound of the

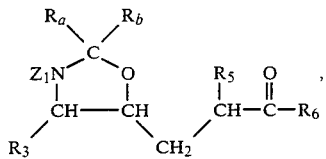

in which the substituents have the meanings mentioned, opening the ring with a suitable solvolysis reagent and optionally removing the protecting group $Z_1$.

The amino-protecting group $Z_1$ is a customary protecting group as mentioned hereinbefore, for example tert.-butoxycarbonyl or benzyloxycarbonyl.

A suitable sulphur-ylide compound is, for example, a dialkylsulphonium methylide, for example dimethylsulphonium methylide, an alkyl- or phenyldialkylaminosulphoxonium methylide, for example methylor phenyl-dimethylaminosulphoxonium methylide, or a dialkylsulphoxonium methylide, for example dimethyl- or diethyl-sulphoxonium methylide.

The sulphur-ylide compound concerned is advantageously manufactured in situ from the corresponding sulphonium or sulphoxonium salt and a base, for example sodium hydride, in a dipolar aprotic solvent, for example dimethyl sulphoxide, or an ether, for example tetrahydrofuran or 1,2-dimethoxyethane, and subsequently reacted with the compound of the formula IX. The reaction is normally effected at room temperature, while cooling, for example down to −20° C., or while heating slightly, for example up to 40° C. The sulphide, sulphinamide or sulphoxide which is formed at the same time is removed during the subsequent aqueous working up operation.

A nucleofugal leaving group X is especially hydroxy esterified by a strong inorganic or organic acid, such as a mineral acid, for example a hydrohalic acid, such as hydrochloric acid, hydrobromic acid or hydriodic acid, or hydroxy esterified by a strong organic sulphonic acid, such as a lower alkanesulphonic acid optionally substituted, for example, by halogen, such as fluorine, or an aromatic sulphonic acid, for example a benzenesulphonic acid optionally substituted by lower alkyl, such as methyl, halogen, such as bromine, and/or by nitro, for example a methanesulphonic acid, trifluoromethanesulphonic acid or p-toluenesulphonic acid, or hydroxy esterified by hydrazoic acid.

A reagent that introduces the nucleofugal leaving group X is, depending on the meaning of X, the free acid HX, for example hydriodic acid or hydrobromic acid, or a salt of that acid, for example sodium or potassium iodide.

The reaction conditions are preferably so chosen that the reaction proceeds substantially as a second-order nucleophilic substitution. For example, for the manufacture of a compound of the formula XI in which X represents a leaving group of high polarisability, for example iodine, a compound of the formula X can be reacted in a dipolar aprotic solvent, for example acetone, acetonitrile, nitromethane or dimethylformamide, with an alkali metal salt of HX, for example sodium iodide.

The reaction may also be carried out in two stages, a compound of the formula X being reacted in water that optionally contains as solubiliser an organic solvent, for example an alcohol, such as ethanol, an ether, for example tetrahydrofuran or dioxan, or acetone, with an alkali metal hydroxide, for example sodium or potassium hydroxide, or with a dilute mineral acid, for example hydrochloric acid or sulphuric acid, or a strong organic sulphonic acid, for example one of the sulphonic acids mentioned above in connection with the leaving group X, and the diol so formed of the formula XI in which X represents OH being reacted with a reagent that introduces the radical X as defined above, for example with a halide of an organic sulphonic acid, for example methanesulphonic acid chloride, benzenesulphonic acid chloride or p-toluenesulphonic acid chloride, with a thionyl halide, for example thionyl chloride, or a phosphorus trihalide, for example phosphorus trichloride or phosphorus tribromide. This reagent that introduces the radical X is preferably reacted in an equimolar amount or slightly in excess in an inert solvent, for example a halogenated hydrocarbon, such as methylene chloride, or an ether, for example diethyl ether, tetrahydrofuran or dioxan, or alternatively in acetonitrile or dimethylformamide, at temperatures of from −20° to +50°, optionally in the presence of an organic or inorganic base, for example triethylamine, ethyldiisopropylamine, pyridine or 4-dimethylaminopyridine, or sodium bicarbonate, calcium carbonate or magnesium carbonate.

Carbonyl compounds of the formula XII are aldehydes or, preferably, ketones in which each of the radicals $R_a$ and $R_b$ represents lower alkyl, preferably having up to 4 carbon atoms, for example methyl or ethyl, aryl or aryl-lower alkyl having up to 10 carbon atoms, for example phenyl or benzyl, especially lower alkanones, for example acetone, or, if $R_a$ and $R_b$ together represent optionally bridged alkylidene, cyclic ketones, especially cycloalkanones, for example cyclohexanone, or bicycloalkanones, for example camphor, and also optically active ketones or aldehydes.

Derivatives of the carbonyl compound of the formula XII are, for example, acetals or enol ethers, above all acetone dimethyl ketal (2,2-dimethoxypropane) or 2-methoxypropene.

Acidic reagents are strong and weak Brönstedt acids, for example mineral acids, for example sulphuric acid or hydrochloric acid, or organic acids, for example p-toluenesulphonic acid, or Lewis acids, for example boron trifluoride etherate, copper sulphate or iron(III) chloride.

Suitable solvents are non-polar, aprotic solvents, for example diethyl ether or hydrocarbons, for example benzene or toluene.

The reaction is preferably carried out at elevated temperatures of from approximately 40° to approximately 150°, above all at the boiling temperature of the particular reaction mixture.

A carboxy-protecting group $Z_2$ is one of the carboxy-protecting groups mentioned hereinbefore under process (a), for example tert.-butyl, benzyl or 4-nitrobenzyl, and also unbranched lower alkyl, for example methyl or ethyl.

The salt of a carboxylic acid ester of the formula XIV is manufactured by reacting the carboxylic acid ester of the formula

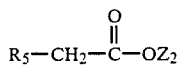

(XIVa)

with a suitable metallating agent.

Suitable metallating agents are substituted and unsubstituted alkali metal amides, alkali metal hydrides or alkali metal lower alkyl compounds in which the alkali metal is sodium or especially lithium, for example sodium or lithium amide, lithium bis-trimethylsilyl amide, sodium hydride, lithium hydride or preferably lithium diisopropyl amide or butyllithium.

Suitable solvents for the metallation reaction must not contain any active hydrogen and are, for example, hydrocarbons, for example hexane, benzene, toluene or xylene, weakly polar ethers, for example diethyl ether, tetrahydrofuran or dioxan, or acid amides, for example hexamethylphosphoric acid triamide. The metallated intermediate of the formula XIV does not need to be isolated but can be reacted with the compound of the formula XIII following the metallation reaction. The metallation reaction is effected at temperatures of from approximately $-100°$ to approximately $0°$, preferably below $-30°$. The further reaction with XV being formed can be effected at the same temperature and, optionally, while slowly heating to the boiling point of the reaction mixture.

The removal of the carboxy-protecting group $Z_2$ is effected under the reaction conditions mentioned hereinbefore for the removal of carboxy-protecting groups. If $Z_2$ is, for example, unbranched lower alkyl, the lower alkyl ester of the formula XV can be cleaved according to customary hydrolysis methods, for example by basic hydrolysis, for example in the presence of potassium tert.-butoxide, in ether or in another organic solvent, optionally in the presence of water. In the case of basic hydrolysis of the lower alkyl ester of the formula XV, the salt of the free carboxylic acid is obtained which can be converted into the free carboxylic acid, for example in aqueous-alcoholic solution. The free carboxylic acid of the formula XV or the salt of that carboxylic acid can be amidated, esterified, or condensed with an amino acid or di- or tri-peptide residue optionally amidated or esterified at the terminal carbon atom, according to the processes described hereinbefore.

The reaction of a resulting compound of the formula XVI with a suitable solvolysis reagent is effected with ring-opening and removal of $R_a(C=O)R_b$ and with the removal of the protecting group $Z_1$ if the latter is a protecting group that can be removed by solvolysis. If $Z_1$ is, for example, a protecting group that can be removed by hydrogenolysis, for example benzyloxycarbonyl, the ring-opening and the removal of this protecting group can also be effected simultaneously by carrying out the hydrogenolysis in the presence of a catalyst, for example palladium-on-carbon, and a solvolysis agent, for example methanol.

Suitable solvolysis agents are, for example, organic acids, for example lower alkanecarboxylic acids, for example glacial acetic acid or formic acid, anhydrides of lower alkanecarboxylic acids, for example acetic anhydride, or sulphonic acids, for example p-toluenesulphonic acid, mineral acids, for example sulphuric or hydrochloric acid, lower alkanols, for example methanol or ethanol, or lower alkanediols, for example ethylene glycol.

The solvolysis reagents mentioned are added undiluted or diluted with water. The solvolysis can also be effected with water alone. The solvolysis with an acidic reagent is effected preferably in an aqueous solution of that reagent and at temperatures of from approximately $-20°$ to approximately the boiling point of the reaction mixture, preferably at room temperature to the boiling point of the reaction mixture.

The entire reaction sequence for the manufacture of the intermediates of the formula VIII can be effected in situ or after isolation of some or all of the preliminary products obtained in accordance with the process.

Compounds of the formula II are novel and the present invention relates also to these compounds. They are manufactured, for example, by reacting a carboxylic acid of the formula

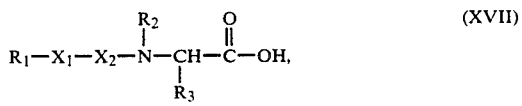

(XVII)

in which the substituents have the meanings mentioned and free functional groups, with the exception of the carboxy group, are optionally in protected form, with an organometal compound of the formula IV in which $R_5$ and $R_6$ have the meanings mentioned and M represents a metal radical, for example -Li or -MgHal, for example -MgCl, -MgBr or -MgI, and solvolysing the addition product formed.

The manufacture of compounds of the formula II can be effected under the reaction conditions specified in process (c).

Compounds of the formula III are known or, if novel, can be manufactured according to processes that are known per se, for example by, in a compound of the formula XVII in which the substituents have the meanings mentioned and free functional groups, with the exception of the carboxy group, are optionally in protected form, reducing the carboxy group to the aldehyde function according to methods that are known per se.

Compounds of the formula IV are known or, if novel, can be manufactured, for example, by reacting a known halide, or a halide that can be manufactured according to methods known per se, of the formula

for example the chloride, with a metallating agent, for example magnesium, lithium or tert.-butyllithium.

Compounds of the formula V are novel and the present invention relates also to these compounds. They are manufactured, for example, by reacting an aldehyde of the formula III with an organometal compound of the formula IV according to process (c) and esterifying the resulting hydroxy compound of the formula I, optionally after separating the isomers, with a strong organic or inorganic acid corresponding to the definition of X, for example as described above for the manufacture of a compound of the formula XI from the corresponding diol.

Nitriles of the formulae VI and VIa are novel and the present invention relates also to these compounds. They are manufactured, for example, by reacting a compound of the formula

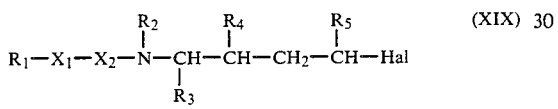

or

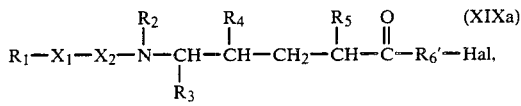

respectively, in which the substituents have the meanings mentioned, with a salt of hydrocyanic acid.

Suitable salts of hydrocyanic acid should be sufficiently soluble in the chosen inert solvent for a reation to take place. Such salts are, for example, ammonium cyanide, alkali metal cyanides or alkaline earth metal cyanides, for example sodium or potassium cyanide, or transition metal cyanides, for example copper cyanide. Owing to their lower basicity as compared with the alkali metal cyanides, the transition metal cyanides are especially suitable.

Depending on the nature of the cyanide used and the solvent, an equilibrium is established between the isomeric nitrile form and the isonitrile form. The nitrile form is preferentially formed if, for example, the reaction is effected with those metal cyanides of which the metal cations have a lower atomic weight than that of copper.

Suitable inert solvents are above all polar, aprotic solvents, for example carboxylic acid amides, for example dimethylformamide or dimethylacetamide, nitriles, for example acetonitrile or propionitrile, or di-lower alkyl sulphoxides, for example dimethyl sulphoxide.

The reaction is effected at room temperature, at reduced or at elevated temperature, for example within a temperature range of from approximately $-40°$ C. to approximately $+100°$ C., preferably from approximately $-10°$ C. to approximately $+50°$ C. and, if desired, under an inert gas atmosphere, for example a nitrogen atmosphere.

Epoxides of the formula VII are novel and the present invention relates also to these compounds. They are manufactured, for example, by reacting a compound of the formula IX with a phosphoranylidene compound of the formula

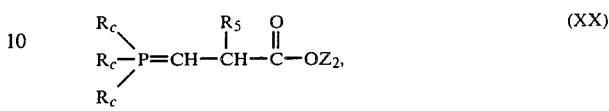

in which $R_c$ represents an optionally substituted hydrocarbon radical, $R_5$ has the meanings mentioned and $Z_2$ is a carboxy-protecting group, and converting a resulting compound of the formula

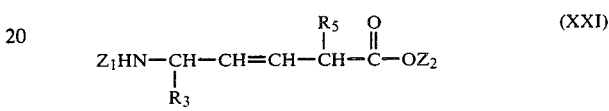

into an epoxide with an oxidising agent containing the peroxo group and, in a resulting compound, removing the protecting groups $Z_1$ and $Z_2$ and replacing them by the groups $R_1—X_1—X_2—$ and $R_6$ in any desired sequence of the reaction steps.

$R_c$ is preferably phenyl. The reaction of a compound of the formula IX with a phosphoranylidene compound of the formula XX is effected under the reaction conditions known for Wittig reactions and described, for example, in the "Organikum". The olefin of the formula XXI which is obtainable in so doing is optionally reacted in situ with the oxidising agent, for example peracetic acid or m-chloroperbenzoic acid. The removal of the protecting groups Z1 and Z2 and the introduction of the groups $R_1—X_1—X_2$ and $R_6$ is described hereinbefore under process a).

The following Examples serve to illustrate the invention. Temperatures are given in degrees Centigrade.

Unless stated otherwise, the $R_f$ values are determined on silica gel thin-layer plates in the following solvent systems:

| | | |
|---|---|---|
| N1 | chloroform/methanol | 9:1 |
| N2 | chloroform/methanol | 95:5 |
| N3 | ethyl acetate/hexane | 1:1 |
| N4 | ethyl acetate/hexane | 1:4 |
| N5 | ethyl acetate/hexane | 1:9 |
| N6 | methylene chloride/ether | 4:1 |
| N7 | methylene chloride/ether | 1:1 |
| N8 | methylene chloride/methanol | 9:1 |
| N9 | methylene chloride/methanol | 6:1 |
| N10 | methylene chloride/methanol | 20:1 |
| N11 | methylene chloride/methanol | 10:1 |
| N12 | methylene chloride/methanol | 5:1 |
| B1 | chloroform/methanol/conc. ammonia | 40:10:1 |
| B2 | chloroform/methanol/conc. ammonia | 350:50:1 |
| B3 | methylene chloride/methanol/-conc. ammonia | 1000:50:1 |
| B4 | methylene chloride/methanol/-conc. ammonia | 350:50:1 |
| B5 | methylene chloride/methanol/-conc. ammonia | 140:10:1 |
| B6 | methylene chloride/methanol/-conc. ammonia | 105:50:1 |
| B7 | methylene chloride/methanol/-conc. ammonia | 90:10:1 |
| B8 | methylene chloride/methanol/-conc. ammonia | 80:10:1 |
| B9 | methylene chloride/methanol/- | 65:10:1 |

| | -continued | |
|---|---|---|
| B10 | methylene chloride/methanol/conc. ammonia | 50:10:1 |
| B11 | methylene chloride/methanol/conc. ammonia | 40:10:1 |
| B12 | methylene chloride/methanol/conc. ammonia | 40:25:1 |
| B13 | methylene chloride/methanol/conc. ammonia | 30:10:1 |
| B14 | methylene chloride/methanol/conc. ammonia | 25:10:1 |
| B15 | methylene chloride/methanol/conc. ammonia | 20:5:1 |
| B16 | methylene chloride/methanol/conc. ammonia | 10:10:1 |
| B17 | ethyl acetate/pyridine/glacial acetic acid/water | 62:21:6:11 |
| B18 | n-butanol/pyridine/glacial acetic acid/water | 38:24:8:30 |
| B19 | pyridine/n-butanol/n-amyl alcohol/methyl ethyl ketone/glacial acetic acid/formic acid/water | 25:20:15:10:3:3:25 |
| B20 | n-butanol/pyridine/formic acid/water | 42:24:4:20 |
| B21 | n-butanol/pyridine/glacial acetic acid/water | 42:24:4:30 |
| B22 | n-butanol/pyridine/formic acid/water | 44:24:2:20 |
| S1 | ethyl acetate/pyridine/glacial acetic acid/water | 62:21:6:11 |
| S2 | ethyl acetate/methanol/glacial acetic acid/water | 67:10:12:23 |
| S3 | chloroform/methanol/water/glacial acetic acid | 300:108:20:2 |
| S4 | chloroform/methanol/water/glacial acetic acid | 75:27:5:0.5 |
| S5 | chloroform/methanol/water/glacial acetic acid | 70:40:10:0.5 |
| S6 | chloroform/methanol/water/glacial acetic acid | 90:10:1:0.5 |
| S7 | chloroform/methanol/water/glacial acetic acid | 55:47:13:0.5 |
| S8 | chloroform/methanol/water/glacial acetic acid | 80:20:3:3 |
| S9 | chloroform/methanol/water/glacial acetic acid | 70:30:3:3 |
| S10 | methylene chloride/methanol/water/glacial acetic acid | 750:270:50:5 |
| S11 | n-butanol/glacial acetic acid/water | 67:10:23 |

For example, the abbreviation "$R_f(N1)$" denotes that the $R_f$ value has been determined in system N1. The ratio of the solvents to one another is given in parts by volume.

The same abbreviations are used for the eluant systems in the flash chromatography and the medium-pressure chromatography.

Abbreviations for amino acids and amino acid derivatives:

| | |
|---|---|
| H—Ala—OH | L-alanine |
| H—Arg—OH | L-arginine |
| H—Glu—OH | L-glutamic acid |
| H—Glu(OR)—OH | L-glutamic acid in which the carboxylic acid function of the side chain has been esterified by the radical R |
| H—Gly—OH | glycine |
| H—His—OH | L-histidine |
| H—Ile—OH | L-isoleucine |
| H—Leu—OH | L-leucine |
| H—Lys—OH | L-lysine |
| H—Lys(R)—OH | L-lysine in which the amino function of the side chain has been substituted by the radical R |
| H—Phe—OH | L-phenylalanine |
| H—(N—methyl-Phe)—OH | N—methyl-L-phenylalanine |
| H—Sta—OH | statin, (3S,4S)4-amino-3-hydroxy-6-methylheptanoic acid |
| H—Val—OH | L-valine |

—NH₂ instead of —OH: C-terminal (carboxylic acid) amide
—OMe instead of —OH: C-terminal (carboxylic acid) methyl ester The fragment referred to as -Leu-Val- denotes the bivalent radical of (2S,4S,5S)-2-isopropyl-4-hydroxy-5-amino-7-methyloctanoic acid and has the formula

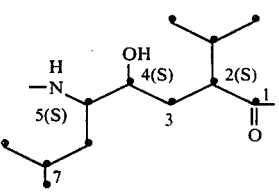

The fragment referred to as -Leu-Val- is derived from the fragment -Leu-Val- by bridging NH and OH by an isopropylidene group and has the formula

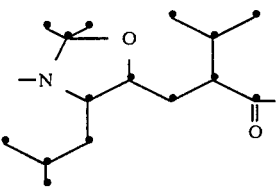

The fragment referred to as -Leu-Gly(R)- denotes the bivalent radical of (4S,5S)-2-R-4-hydroxy-5-amino-7-methyloctanoic acid having the (R)- or (S)-configuration at the C-atom 2 and has the formula

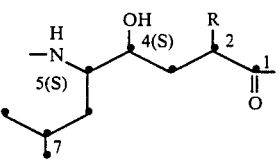

The fragment referred to as -Leu-Gly(R)- is derived from the fragment -Leu-Gly(R)- by bridging NH and OH by an isopropylidene group.

| Other abbreviations: | |
|---|---|
| Ac = | acetyl |
| BOC = | tert.-butoxycarbonyl |
| TLC = | thin-layer chromatography, unless stated otherwise on silica gel |
| DCCI = | dicyclohexyl carbodiimide |
| DCH = | dicyclohexylurea |
| DMF = | dimethylformamide |
| DMSO = | dimethyl sulphoxide |
| HOBt = | 1-hydroxybenzotriazole |
| min. = | minutes |
| b.p. = | boiling point |
| m.p. = | melting point |
| THF = | tetrahydrofuran |
| vol. = | parts by volume |
| Z = | benzyloxycarbonyl |

EXAMPLE 1

Z-Phe-His-Leu-Val-Ile-His-NH₂

1.7 g of Z-Phe-His-OH (produced in accordance with the directions in Chem. Ber. 94, 2768 (1961)), 1.71 g of H-Leu-Val-Ile-His-NH₂ and 544 mg of HOBt (Fluka purum, contains 11-13% of water) are cooled in 60 ml of absolute DMF to 0°. After the addition of 1.03 g of DCCI, the whole is stirred for 15 hours while cooling with an ice bath and then for 2 days at room temperature. The suspension is concentrated in a high vacuum and the residue is stirred for 60 minutes in a mixture of methanol/water/glacial acetic acid (94:3:3) in an oil bath at 60°. After removal of the solvent in a high vacuum, the residue is separated by flash chromatography (1000 g of silica gel 60, 40-63 μm, eluant system B8). The product-containing fractions are concentrated by evaporation. After drying in a high vacuum, Z-Phe-His-Leu-Val-Ile-His-NH₂ is obtained in the form of a colourless powder. R_f(B4)=0.07, R_f(S3)=0.29. The product can be converted into the dihydrochloride by being stirred up in methanol and adding 2 equivalents of aqueous 1N HCl.

The starting material H-Leu-Val-Ile-His-NH₂ can be produced in accordance with the following reaction scheme:

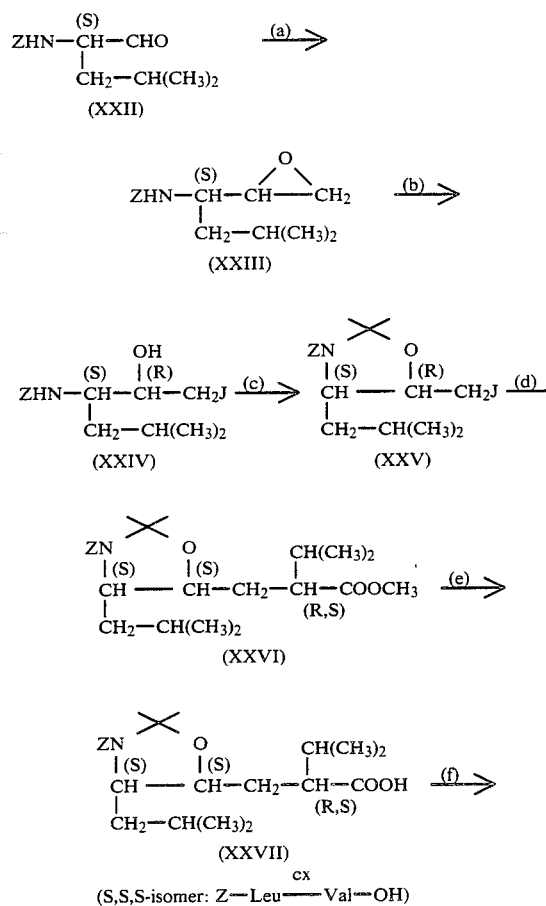

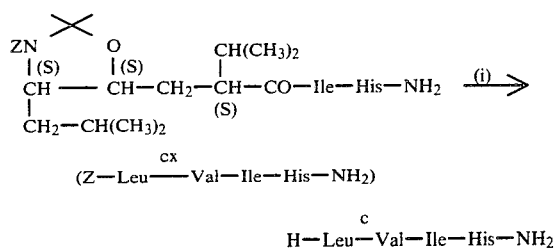

(a) 8.75 g of sodium hydride dispersion (55% in oil) are freed from oil in a dry sulphonating flask under argon by stirring up three times in 85 ml of petroleum ether (boiling point 40°-60°) and subsequently decanting the solvent. After drying in a high vacuum a grey powder is obtained to which there is added dropwise a solution of 44.1 g or trimethylsulphoxonium iodide in 180 ml of dimethyl sulphoxide, the temperature rising to approximately 40°. The grey suspension is stirred at room temperature for 1 hour and then, over a period of 50 minutes at 10°, there is added a solution of 43.4 g of (S)-2-benzyloxycarbonylamino-4-methyl-pentanal (XXII) (manufacture: Helvetica Chimica Acta 66, 450 (1983) in 180 ml of DMSO. The yellow suspension is stirred for 15 minutes at 10° and then for 1.5 hours at room temperature. The yellowish turbid solution is poured onto 500 g of ice. The aqueous solution is extracted with ether, and the organic phase is washed with water and, after being dried over sodium sulphate, concentrated by evaporation. The oily residue is separated by means of flash chromatography over 2 g of silica gel (40-63/μm) with a mixture of methylene chloride/n-hexane/ethyl acetate (5:10:3). The product-containing fractions are combined, concentrated by evaporation and dried in a high vacuum. The epoxide (XXIII) (diastereoisomeric mixture, approximately 3:1) is obtained in the form of a slightly yellowish oil. R_f(B1)=0.57, R_f(N4)=0.16.

(b) 33.8 g of compound (XXIII) are taken up in 255 ml of acetonitrile and the resulting solution is cooled to 0°. After the addition of 19.24 g of sodium iodide, 16.27 ml of trimethylchlorosilane are added dropwise at 0° over a period to 30 minutes. The mixture is stirred for 40 minutes at 0°-3° and then poured into 250 ml of ice-cold water. The aqueous mixture is extracted with ether and the organic phase is washed with 10% strength aqueous sodium thiosulphate solution and saturated aqueous sodium chloride solution. After drying over sodium sulphate and concentration by evaporation, an oily mixture of the desired alcohol (XXIV) and the corresponding trimethylsilyl ether (both diastereoisomeric mixtures) is obtained. The free alcohol is separated by means of flash chromatography (2 kg of silica gel 60, 40-63 μm, eluant ethyl acetate/hexane 1:4). The product-containing fractions are combined and concentrated by evaporation to yield the alcohol (XXIV) in the form of an oil. The fractions containing the trimethylsilyl ether are combined and concentrated by evaporation, the residue is taken up in THF, a solution of 2.67 g of tetrabutylammonium fluoride in water is added, and the resulting mixture is stirred for 3 days at room temperature. The solution is than extracted by shaking with water and ether. The organic phase is washed with water, dried over sodium sulphate and concentrated by evaporation. After drying in a high vacuum, an additional amount of the diastereoisomeric mixture of compound (XXIV) is obtained in the form of an oil. For the purpose of further purification, the total amount of diastereoisomeric mixture (XXIV) is separated into two portions by medium-pressure chromatography (1.4 kg Lichroprep ® Si 60, 25–40 μm, eluant: ethyl acetate/hexane (1:8), fractions of approximately 220 ml). Crystallisation from petroleum ether (b.p. 40°–60°) allows the more strongly polar component to be removed from the crude material and the mixed fractions to be to some extent enriched (m.p. 104°–106°). The two diastereoisomers are obtained in a ratio of approximately 3:1. The less polar, oily component is the desired compound (XXIV). $R_f(N4)=0.16$, $R_f(B1)=0.54$.

(c) 66.6 g of compound (XXIV) and 1.62 of p-toluenesulphonic acid monohydrate are refluxed for 3 hours in 1500 ml of 2,2-dimethoxypropane. After being cooled to room temperature, the mixture is extracted by shaking with 1000 ml of ether and 500 ml of saturated aqueous sodium bicarbonate solution. The organic phase is washed with water, dried over sodium sulphate and concentrated by evaporation. The semi-crystalline crude product is purified by means of flash chromatography (2 kg of silica gel 60, 40–63 μm, eluant ethyl acetate/hexane (1:6), fractions of approximately 400 ml). By concentrating by evaporation the combined product-containing fractions, compound (XXV) is obtained in the form of slightly yellowish crystals. $R_f(N4)=0.48$, $R_f(N5)=0.26$.

(d) 10.82 ml of diisopropylamine are dissolved in 100 ml of absolute tetrahydrofuran under argon and cooled to 0°. Then, at 0°–5°, a 1,6M solution of n-butyllithium in hexane is added dropwise for 20 minutes to the mixture, and the whole is stirred for 15 minutes. Subsequently, at from −70° to −75°, 10.1 ml of isovaleric acid methyl ester are added dropwise and the mixture is stirred for 1.5 hours at −75°. At from −60° to −75°, 190 ml of hexamethylphosphoric acid triamide are added dropwise while stirring. The resulting suspension is stirred for 10 minutes and then, at from −70° to −75°, a solution of 30.0 g of compound (XXV) in 50 ml of tetrahydrofuran is added dropwise over a period of 5 minutes. The reaction mixture is stirred at room temperature for 2.5 hours and then poured into a mixture of 450 ml of saturated aqueous ammonium chloride solution and 500 g of ice. The aqueous phase is extracted with ether and the organic phase is washed with water and dried over sodium sulphate. Concentration by evaporation yields the diastereoisomeric mixture of compound (XXVI) in the form of a yellow oil. $R_f(N5)=0.20$, $R_f(N4)=0.40$ (values for the less polar component).

(e) 1.07 ml of water are added at approximately 5° to 10.7 g of potassium tert.-butoxide in 80 ml of ether. The white suspension is stirred for a further 10 minutes in an ice bath and then 10.0 g of compound (XXVI) (diastereoisomeric mixture) in 80 ml of ether are added, the temperature being maintained below 10°. The reaction mixture is then stirred for 18 hours at room temperature and subsequently poured into 1600 ml of saturated aqueous ammonium chloride solution. The aqueous phase is extracted with ether and the organic phase is washed with saturated aqueous sodium chloride solution, dried over sodium sulphate and concentrated by evaporation. The oily crude product is separated by means of medium-pressure chromatography (740 g of Lichroprep ® Si 60, 25–40 μm, eluant: ethyl acetate/hexane 1:5). Z-Leu-Val-OH, the less polar component of compound (XXVII) with the desired configuration of the C-atom bonded to the isopropyl group (S-configuration), is obtained in the form of a yellow oil. $R_f$ (methylene chloride/methanol/water 500:10:1)=0.13, $R_f$ (N6)=0.58.

(f) Z-Leu-Val-Ile-His-NH$_2$: 1.96 g of Z-Leu-Val-OH, 1.42 g of H-Ile-His-NH$_2$ (for manufacture see g) and 0.74 g of HOBt are cooled to 0° in 15 ml of DMF. After the addition of 1.3 g of DCCI, the whole is stirred for 2 hours at 0° and then 18 hours at room temperature, The resulting DCH is filtered off and the solvent of the filtrate is concentrated by evaporation in a high vacuum. The residue is taken up in a mixture of 25 ml of methanol/water/acetic acid (94:3:3) and stirred for 1 hour at 60°. The whole is then concentrated to dryness by evaporation and the residue is stirred for 30 minutes in 40 ml of methanol in an ice bath. After filtration and removal of the solvent by evaporation, the residue is taken up in n-butanol and washed with saturated sodium bicarbonate solution and saturated sodium chloride solution. The organic phase is dried over sodium sulphate and concentrated by evaporation. The crude product is separated by medium-pressure chromatography (240 g of Lichroprep ® Si 60, 25–40 μm, fractions of approximately 40 ml, pressure approximately 8 bars, eluant: methylene chloride/methanol/water 80:10:1, flow rate 40 ml/min). After approximately 20 minutes the product is eluted. The title compound is obtained by concentrating by evaporation the product-containing fractions. $R_f(S3)=0.19$, $R_f(B4)=0.48$.

(g) H-Ile-His-NH$_2$: 2.5 g of Z-Ile-His-NH$_2$ are dissolved in 25 ml of methanol/water (9:1) and hydrogenated in the presence of 400 mg of palladium-on-carbon (10%) with $CO_2$ absorption until saturation is reached. The catalyst is filtered off, the filtrate is concentrated to dryness and the residue is purified by flash chromatography over silica gel in system S9. The product-containing fractions are concentrated in a rotary evaporator and dried in a high vacuum to yield H-Ile-His-NH$_2$.

(h) Z-Ile-His-NH$_2$: 3.0 g of Z-Ile-His-OCH$_3$ are dissolved in 120 ml of a 5N. methanolic ammonia solution and stirred for 16 hours at room temperature. The colourless precipitate formed is removed by filtration and dried in a high vacuum. $R_f(S5)=0.58$, m.p. 204°–205°.

(i) H-Leu-Val-Ile-His-NH$_2$: 1.352 g of Z-Leu-Val-Ile-His-NH$_2$ are hydrogenated for 1 hour under normal pressure at room temperature in 25 ml of methanol/water (95:5) in the presence of 150 mg of palladium-on-carbon (5%). After removing the catalyst by filtration, the solvent is evaporated off and the residue is stirred for 30 minutes at room temperature in 30 ml of methanol/water (1:1). After evaporating off the solvent and drying in a high vacuum, H-Leu-Val-Ile-His-NH$_2$ is obtained in the form of a colourless powder. $R_f(B4)=0.1$, $R_f(B11)=0.42$.

EXAMPLE 2

BOC- Phe-His-Leu-Val-Ile-His-NH$_2$

In a manner analogous to that described in Example 1, using as starting materials 92 mg of BOC-Phe-His-OH (produced in accordance with the directions given in U.S. Pat. No. 4,025,499) and 100 mg of H-Leu-Val-Ile-His-NH$_2$, the title compound is obtained after the addition of 35 mg of HOBt and 56 mg of DCCI and chromatographic purification over a LOBAR ® prefabricated column (eluant: methylene chloride/methanol/concentrated ammonia 390:60:2). $R_f(B11)=0.32$, $R_f(S3)=0.19$.

EXAMPLE 3

Z-Phe-Phe-Leu-Val-Ile-His-NH$_2$

In a manner analogous to that described in Example 1, using as starting materials 54 mg of Z-Phe-Phe-OH(Bachem AG, Bubendorf, Switzerland) and 75 mg of H-Leu-Val-Ile-His-NH$_2$, the title compound is obtained after the addition of 26 mg of HOBt and 42 mg of DCCI and chromatographic purification over a LOBAR ® prefabricated column (eluant: methylene chloride/methanol/water 50:10:1). $R_f(B10)=0.35$.

EXAMPLE 4

H-Phe-His-Leu-Val-Ile-His-NH$_2$ 3.14 g of the dihydrochloride of Z-Phe-His-Leu-Val-Ile-His-NH$_2$ from Example 1 are hydrogenated for 4 hours at normal pressure in 100 ml of water/methanol (5:95) in the presence of 350 mg of palladium-on-carbon (5%). After removing the catalyst by filtration, evaporating off the solvent and drying in a high vacuum, H-Phe-His-Leu-Val-Ile-His-NH$_2$.2HCl is obtained in the form of a colourless powder. $R_f(B11)=0.26$.

EXAMPLE 5

BOC-Phe-His-Leu-Val-7-tert.-butoxycarbonylheptyl amide

In a manner analogous to that discribed in Example 1, using as starting materials 81 mg of BOC-Phe-His-OH, 79 mg of H-Leu-Val-7-tert.-butoxycarbonyl-heptyl amide, 28 mg of HOBt and 57 mg of DCCI, the title compound is obtained in the form of a colourless powder after flash chromatography (30 g of silica gel 60, 40–63 μm, system: methylene chloride/methanol/concentrated ammonia 800:50:1). $R_f$(methylene chloride/methanol/concentrated ammonia 500:50:1)=0.33.

The starting materials are manufactured in the following manner;

(a) H-Leu-Val-7-tert.-butoxycarbonyl-heptyl amide is obtained by hydrogenation of 213 mg of Z-Leu-Val-7-tert.-butoxycarbonyl-heptyl amide in the presence of 40 mg of pailadium-on-carbon (10%) in a-manner analogous to that described in Example 1i. $R_f(B2)=0.13$.

(b) Z-Leu-Val-7-tert.-butoxycarbonyl-heptyl amide is obtained in a manner analogous to that described in Example 1 using as starting materials 162 mg of Z-Leu-Val-OH and 103 mg of 8-aminooctanoic acid tert.-butyl ester and adding 61 mg of HOBt, 53 μl of 4-methylmorpholine and 107 mg of DCCI. $R_f(N4)=0.20$.

(c) 8-aminooctanoic acid tert.-butyl ester is obtained in the form of a colourless oil by hydrogenation of 1.5 g of 8-benzyloxycarbonylaminooctanoic acid tert.-butyl ester in 15 ml of methanol with the addition of 0.10 g of palladium-on-carbon (10)%, analogously to Example 4. $R_f(B3)=0.08$.

(d) 8-benzyloxycarbonylaminooctanoic acid tert.-butyl ester: In an autoclave, 2 g of 8-benzyloxycarbonylaminooctanoic acid in 12 ml of dioxan are reacted in the presence of 1.2 ml of sulphuric acid with 7.5 g of isobutylene and the whole is left to stand for 48 hours at room temperature. Ice and 40 ml of 1.8N aqueous ammonia solution are added to the reaction mixture. The reaction mixture is extracted with ether. The organic phase is washed with water and saturated aqueous sodium chloride solution, dried over sodium sulphate and concentrated in vacuo. The title compound is obtained in the form of a clear yellow oil. $R_f(N8)=0.44$.

(e) 8-benzyloxycarbonylaminooctanoic acid: 25 ml of 2N NaOH solution are added to 7 g of 8-aminooctanoic acid. There are then added simultaneously, at approximately 0°–5° over a period of 30 minutes, 17.1 g of chloroformic acid benzyl ester (50% in toluene) and 12.5 ml of 4N NaOH solution. A voluminous whitb precipitate is observed. 150 ml of ether and 60 ml of water are added to the reaction mixture. The aqueous phase is extracted with ether, ice is added and, while stirring, the pH is slowly brought to 2 with dilute aqueous HCl solution. The resulting suspension is extracted twice with ethyl acetate. The organic phases are combined, washed with water and saturated aqueous sodium chloride solution, dried over sodium sulphate and concentrated by evaporation in vacuo. The title compound, having a meltiang point of 63°–64°, is obtained. $R_f(N1)=0.53$.

EXAMPLE 6

[o-(2,6-dichloro-N-benzylanilino)-phenyl]-acetyl-Phe-His-Leu-Val-Ile-His-NH$_2$ In a manner analogous to that described in Example 1, using as starting materials 75 mg of N-benzyl-Diclofenac (manufactured in accordance with DOS No. 2 840 589), 150 mg of H-Phe-His-Leu-Val-Ile-His-NH$_2$.2HCl, 27 mg of HOBt, 0.5 ml of ethyldiisopropylamine and 52 mg of DCCI, the title compound is obtained in the form of a colourless powder after flash chromatography (70 g of silica gel 60, 40–63 μm, system B8). $R_f(B11)=0.47$

EXAMPLE 7

[o-(2,6-dichloroanilino)-phenyl]-acetyl-Phe-His-Leu-Val-Ile-His-NH$_2$ 134 mg of [o-(2,6-dichloro-N-benzylanilino)-phenyl]-acetyl-Phe-His-Leu-Val-Ile-His-NH$_2$ (Example 6) are hydrogenated for 10 hours under normal pressure in the presence of 90 mg of palladium-on-carbon (5%) and 0.4 ml of o-dichlorobenzene in 10 ml of MeOH. After removing the catalyst by filtration and evaporating off the solvent, the residue is separated by medium-pressure chromatography (LOBAR ® prefabricated column, size B (Merck), 40–60 μm, system B10, approximately 30 ml/min). After evaporating off the solvent from the product-containing fractions and drying, the title compound is obtained in the form of a colourless powder. $R_f(B11)=0.44$.

EXAMPLE 8

3(R),4(S),5,(R)-trihydroxy-1-cyclohexene-1-carbonyl-Phe-His-Leu-Val-Ile-His-NH$_2$ In a manner analogous to that described in Example 1, using as starting materials 17 mg of shikimic acid, 75 mg of H-Phe-His-Leu-Val-Ile-His-NH$_2$.2HCl, 14 mg of HOBt, 0.36 ml of diisopropylethylamine and 26 mg of DCCI, the title compound is obtained in the form of a colourless powder after flash chromatography (30 g of silica gel 60, 40–63 μm, system: methylene chloride/methanol/concentrated ammonia 40:20:1). $R_f(B12)=0.23$.

EXAMPLE 9

Z-Arg-Gly-Phe-His-Leu-Val-Ile-His-NH$_2$

In a manner analogous to that described in Example 1, using as starting materials 36 mg of Z-Arg-Gly-OH (manufactured according to J. Chem. Soc. 1965, 782), H-Leu-Val-Ile-His-NH$_2$.2HCl, 14 mg of HOBt, 0.36 ml of ethyldiisopropylamine and 26 mg of DCCI, the title compound is obtained in the form of a colourless powder after flash chromatography (110 g of silica gel 60, 40–63 μm, system: methylene chloride/methanol/water/glacial acetic acid 280:140:30:2). Rf (methylene chloride/methanol/water/glacial acetic acid 140:30:20:1)=0.25.

EXAMPLE 10

(2S,4R)-N-benzyloxycarbonyl-4-hydroxypyrrolidine-2-carbonyl-Phe-His-Leu-Val-Ile-His-NH$_2$ In a manner analogous to that described in Example 1, using as starting materials 42 mg of N-benzyloxycarbonyl-4-hydroxy-L-proline, 120 mg of H-Phe-His Leu-Val-Ile-His-NH$_2$.2HCl, 22 mg of HOBT, 0.57 ml of ethyldiisopropylamine and 41 mg of DCCI, the title compound is obtained in the form of a colourless powder after flash chromatography (70 g of silica gel 60, 40–63 μm, system B11). R$_f$(B13)=0.41.

EXAMPLE 11

(2S,4R)-4-hyroxpyrrolidine-2-carbonyl-Phe-His-Leu-Val-Ile-His-NH$_2$

In a manner analogous to that described in Example 4, the title compound is obtained in the form of a colourless powder by hydrogenating 39.6 mg of (2S,4R)-N-benzyloxycarbonyl-4-hydroxpyrrolidine-2-carbonyl-Phe-His-Leu-Val-Ile-His-NH$_2$ (Example 10) and flash chromatography (10 g of silica gel 60, 40–63 μm, system B 13). R$_f$(B13)=0.38.

EXAMPLE 12

(5S)-2-pyrrolidone-5-carbonyl-Phe-His-Leu-Val-Ile-His-NH$_2$

In a manner analogous to that described in Example 1, using as starting materials 12.7 mg of L-pyroglutamic acid, 75 mg of H-Phe-His-Leu-Val-Ile-His-NH$_2$.2HCl, 14 mg of HOBT, 0.36 ml of ethyldiisopropylamine and 26 mg of DCCI, the title compound is obtained in the form of a colourless powder after flash chromatography (200 g of silica gel 60, 40–63 um, system B11). R$_f$(B11)=0.21.

EXAMPLE 13

BOC-Phe-His-Leu-Val-Ala-Sta-OCH$_3$

In a manner analogous to that described in Example 1, using as starting materials 52 mg of BOC-Phe-His-OH, 60 mg of H-Leu-Val-Ala-Sta-OCH$_3$.HCl, 18 mg of HOBT, 0.24 ml of ethyldiisopropylamine and 34 mg of DCCI, the title compound is obtained in the form of a colourless powder after flash chromatography (30 g of silica gel 60, 40–63 μm, system N8). Rf(N9)=0.38.

The starting materials are manufactured in the following manner:

(a) H-Leu-Val-Ala-Sta-OCH$_3$.HCl is obtained in the form of a colourless powder by hydrogenating 602 mg of Z-Leu-Val-Ala-Sta-OCH$_3$ with 65 mg of palladium-on-carbon (5%) at a pH of 5.0 in a manner analogous to that described in Example 4. R$_f$(B11)=0.5.

(b) Z-Leu-Val-Ala-Sta-OCH$_3$ is obtained in the form of a colourless powder in a manner analogous to that described in Example 1, using as starting materials 677 mg of Z-Leu-Val-OH (Example 1e), 546 mg of H-Ala-Sta-OCH$_3$.HCl, 0.31 ml of ethyldiisopropylamine, 256 mg of HOBT and 483 mg of DCCI and carrying out medium-pressure chromatography (245 g Lichroprep$^R$ Si60, 25–40 μm, system:methylene chloride/ether 2:1). Rf (ethyl acetate/hexane 3:1)=0.32.

(c) H-Ala-Sta-OCH$_3$.HCl is obtained in the form of a colourless powder by hydrogenating 750 mg of Z-Ala-Sta-OCH$_3$ with 80 mg of palladium-on-carbon (10%) at a pH of 5.0 in a manner analogous to that described in Example 4. R$_f$(B4)=0.25.

(d) Z-Ala-Sta-OCH$_3$ is obtained in the form of a colourless powder in a manner analogous to that described in Example 1, using as starting materials 1.09 g of Z-Ala-OH, 1.00 g of statin methyl ester hydrochloride (manufactured as described in European Patent Application No. 111 266), 678 mg of HOBT, 0.49 ml of ethyldiisopropylamine and 1.28 g of DCCI, and carrying out flash chromatography (330 g of silica gel 60, 40–63 μm, system ethyl acetate/hexane 3:2). Rf (ethyl acetate/hexane 2:1)=0.24.

EXAMPLE 14

Z-Phe-His-Leu-Val-Ala-Sta-OCH$_3$

In a manner analogous to that described in Example 1, using as starting materials 56 mg of Z-Phe-His-OH, 60 mg of H-Leu-Val-Ala-Sta-OCH$_3$.HCl, 18 mg of HOBT, 0.24 ml of ethyldiisopropylamine and 34 mg of DCCI, the title compound is obtained in the form of a colourless powder after flash chromatography (30 g of silica gel 60, 40–63 μm, system N8). R$_f$(N9)=0.33.

EXAMPLE 15

4-benzyloxycarbonylaminobutyryl-Gly-Phe-His-Leu-Val-Ile-His-NH$_2$

In a manner analogous to that described in Example 1, using as starting materials 29 mg of 4-(benzyloxycarbonylamino)-butyrl-Gly-OH, 75 mg of H-Phe-His-Leu-Val-Ile-His-NH$_2$.2HCl, 14 mg of HOBT, 18 mg of N-methylmorpholine and 26 mg of DCCI, the title compound is obtained in the form of a colourless powder after flash chromatography (30 g of silica gel 60, 40–63 μm, system B9). R$_f$(B11)=0.21. The preparation can be converted in methanol with 2 equivalents of aqueous 1N HCl into the dihydrochloride.

The starting materials are manufactured in the following manner:

(a) 4-(benzyloxycarbonylamino)-butyryl-Gly-OH is obtained by treating 1.6 g of 4-(benzyloxycarbonylamino)-butyryl-Gly-OCH$_3$ in 10 ml of methanol with 7.8 ml of 1N NaOh at room temperature for 1 hour. After the addition of 7.8 ml of 1N HCl, the solvent is evaporated off and the residue is stirred in 50 ml of CH$_2$Cl$_2$/MeOH(5:1). After filtering off the undissolved NaCl, evaporating off the solvent and drying in vacuo, the title compound is obtained in the form of a colourless powder. R$_f$(B11)=0.05.

(b) 4-(benzyloxycarbonylaino)-butyryl-Gly-OCH$_3$ is obtained in a manner analogous to that described in Example 1, using as starting materials 4.0 g of 4-benzyloxycarbonylam inobutyric acid (manufactured from 4-aminobutyric acid in a manner analogous to that described in Example 5e), 1.93 g of glycine methyl ester hydrochloride, 1.58 ml of N-methylmorpholine, 2.58 g of HOBT and 4.11 g of DCCI, and carrying out medium-pressure chromatography (240 g of Lichroprep® Si60, Merck, 25–40 μm, system methylene chloride/methanol 95.5), in the form of of colourless oil. R$_f$(S3)=0.79.

EXAMPLE 16

4-aminobutyryl-Gly-Phe-His-Leu-Val-Ile-His-NH$_2$

By hydrogenating 300 mg of 4-(benzyloxcarbonylamino)-butyryl-Gly-Phe-His-Leu-Val-Ile-His-NH$_2$ (Example 15) in a manner analogous to that described in Example 4, the title compound is obtained after flash chromatography (30 g of silica gel 60, 40–63 μm, system B14) in the form of a colourless powder, R$_f$(B10)=0.18.

EXAMPLE 17

(2R,3R)-2,3-bis-acetoxy-3-methoxycarbonylpropionyl-Phe-His-Leu-Val-Ile-His-NH$_2$ In a manner analogous to that described in Example 1, using as starting materials 24 mg of L(+)-tartaric acid monomethyl ester bis-acetate (manufactured in accordance with the directions in J. Amer. Chem. Soc. 63, 1653 (1941)), 75 mg of H-Phe-His-Leu-Val-Ile-His-NH$_2$.2HCl, 14 mg of HOBt, 0.36 ml of ethyldiisopropylamine and 26 mg of DCCI, the title compound is obtained in the form of a slightly yellowish power after flash chromatography (30 g of silica gel 60, 40–63 μm, system methylene chloride/methanol/concentrated ammonia 80:20:1). R$_f$(B11)=0.31.

EXAMPLE 18

(2R,3R)-2,3-dihydroxy-3-methoxcarbonylpropionyl-Phe-His-Leu-Val-Ile-His-NH$_2$ 44 mg of (2R,3R)-2,3-bis-acetoxy-3-methoxycarbonylpropionyl-Phe-His-Leu-Val-Ile-His-NH$_2$ (Example 16) are stirred at 0° for 2.5 hours with 1N aqueous ammonia solution/methanol 1:1. After evaporating off the solvent and flash chromatography (10 g of silica gel 60, 40–63 μm, system B11), the title compound is obtained in the form of a colourless powder. R$_f$(B13)=0.31.

EXAMPLE 19

Z-Phe-His-Leu-Val-4-[tris-(tert.-butyldimethylsiyloxymethyl)-methylamino carbonl]-butyl amide In a manner analogous to that described in Example 1, using as starting materials 60 mg of Z-Phe-His-OH, 98 mg of H-Leu-Val-4-[tris-(tert.-butyldimethylsilyloxmethyl)-methylaminocarbonl]-butyl amide, 21 mg of HOBt, 14 μl of ethyldiisopropylamine and 34 mg of DCCI, the title compound is obtained in the form of a colourless powder after medium-pressure chromatography (60 g of Lichroprep® Si60, 40–60 μm, system methylene chloride/methanol/concentrated ammonia 120:10:1).R$_f$(methylene chloride/methanol/concentrated ammonia 120:10:1)=0.16.

The starting materials are manufactured in the following manner:

(a) H-Leu-Val-4-[tris-(tert.-butyldimethylsilyloxymethyl)-methylaminocarbonyl]-butyl amide is obtained by hydrogenating 900 mg of Z-Leu-Val-4-[tris-(tert.-butyldimethylsilyloxmethyl)-methylaminocarbonyl]-butyl amide with 90 mg of palladium-on-carbon (5%) in a manner analogous to that described in Example 1i and subsequent medium-pressure chromatography (60 g of Lichroprep® Si60, 40–60 μm, system B7). Colourless oil, R$_f$(B7)=0.24.

(b) Z-Leu-Val-4-[tris(tert,-butyldimethylsilyloxymethyl)-methylaminocarbonyl]-butyl amide is obtained in the form of a colourless oil in a manner analogous to that described in Example 1, using as starting materials 500 mg of Z-Leu-Val-OH, 694 mg of 5-aminovaleric acid tris-(tert.-butyldimethylsilyloxmethyl)-methyl amide, 0.21 ml of diisopropylethylamine, 189 mg of HOBT and 331 mg of DCCI, and carrying out medium-pressure chromatography (60 g of Lichroprep® Si60, 40–60 μm, system N4). R$_f$(N3)=0.57.

(c) 5-aminovaleric acid tris-(tert.-butyldimethylsilyloxymethyl)-methyl amide is obtained by hydrogenating 4.03 g of the corresponding 5-benzyloxycarbonylamino compound with 0.4 g of palladium-on-carbon (5%) in a manner analogous to that described in Example 4, and medium-pressure chromatography (60 g of Lichroprep® Si60, 40–60 μm, system N12). Colurless oil, R$_f$(B7)=0.28.

(d) 5-benzyloxcarbonylaminovaleric acid tris(tert.-butyldimethylsilyloxymethyl)-methyl amide is obtained in the form of a colourless oil in a manner analogous to that described in Example 1, using as starting materials 291 mg of 5-benzyloxycarbonylaminovaleric acid, 500 mg of tris-(tert.-butyldimethylsilyloxymethyl)-methylamine, 182 mg of HOBt, 0.2 ml of ethyldiisopropylamine, 189 mg of DCCI, and carrying out medium-pressure chromatography (60 g of Lichroprep® Si60, 40–60 μm, system N4). R$_f$(N4)=0.56.

(e) Tris-(Tert.-butyldirthylsilyloxmethyl)-methylamine is obtained in the form of a colourless oil by hydrogenating 399 mg of the corresponding benzyloxycarbonyl derivative with 50 mg of palladium-on carbon (5%). R$_f$(N4)=0.41.

(f) Benzyloxcarbonyl-tris-(tert.-butyldimethylsilyloxymethyl)-methyl amide is produced from 250 mg of benzloxcarbonyl-tris-(hyrdoxymethyl)-methyl amide, 234 mg of imidazole and 472 mg of tert.-butyldimethylsily chloride in 10 ml of DMF at room temperature for 15 hours.

(g) Benzyloxycarbonyl-tris-(hydroxymethyl)-methyl amide is produced from 20 g of tris-(hydroxymethyl)-methylamine, 31.3 g of chloroformic acid benzyl ester and 42.4 ml of triethylamine in 200 ml of DMF at 0°. After evaporating off the solvent the residue is taken up in ethyl acetate and washed with 2N HCl and saturated sodiμmchloride solution, the organic phase is dried and the solvent is evaporated off. R$_f$(N8)=0.27.

EXAMPLE 20

Z-Phe-His-Leu-Val-4-[tris-(hydroxymethyl)-methylaminocarbonyl]-butyl amide 83 mg of Z-Phe-His-Leu-Val-4-[-tris-(tert.-butyldimethylsilyloxymethyl)-methylaminocarbonyl]-butyl amide (Example 19) are stirred at room temperature for 2 hours with 6 ml of glacial acetic acid/water 2:1. After evaporating off the solvent and medium-pressure chromatography (60 g of Lichroprep® Si60, 40–60 μm, system B8), the title compound is obtained in the form of a colourless powder. R$_f$(methylene chloride/methanol/concentrated ammonia 70:10:1)=0.11.

EXAMPLE 21

8-(benzyloxycarbonylamino)-octanoyl-Phe-His-Leu-Val-Ile-His-NH$_2$

In a manner analogous to that described in Example 1, using as starting materials 75 mg of H-Phe-His-Leu-Val-Ile-His-NH$_2$.2HCl, 29 mg of 8-benzyloxycarbonylaminooctanoic acid, 14 mg of HOBt, 0.36 ml of ethyldiisopropylamine and 26 mg of DCCI in 2 ml of DMF, the title compound is obtained in the form of a

EXAMPLE 22

8-aminooctanoyl-Phe-His-Leu-Val-Ile-His-NH$_2$

By hydrogenating 60 mg of 8-(benzloxycarbonylamino)-octanoyl-Phe-His-Leu-Val-Ile-His-NH$_2$ (Example 21) in a manner analogous to that described in Example 4, the title compound is obtained in the form of a colourless powder after flash chromatography (10 g of silica gel 60, 40–63 μm, system B16). R$_f$(B16)=0.38.

EXAMPLE 23

Z-Phe-His-Leu-Val-2-methoxycarbonyl-1-methyleethyl amide

In a manner analogous to that described in Example 1, using as starting materials 161 mg of Z-Phe-His-OH, 122 mg of H-Leu-Val-2-methoxycarbonyl-1-methyl-ethyl amide, 57 mg of HOBt and 99 mg of DCCI in 6 ml of DMF, the title compound is obtained in the form of a white amorphous powder after flash chromatography (160 g of silica gel 60, 40–63 μm, system N8). R$_f$(N8)=0.20, R$_f$(B2)=0.44.

The starting materials are manufactured in the following manner:

(a) H-Leu-Val-2-methoxycarbonyl-1-methyl-ethyl amide is obtained by hydrogenating 187 mg of Z-Leu-Val-2-methoxycarbonyl-1-methyl-ethyl amide in the presence of 30 mg of palladium-on-carbon (10%) in a manner analogous to that described in Example 1i and further processed as a crude prodcute. R$_f$(B2)=0.22.

(b) Z-Leu-Val-2-methoxycarbonyl-1-methyl-ethyl amide is obtained in a manner analogous to that described in Example 1 using as starting materials 162 mg of Z-Leu-Val-OH (Example 1e), 59 mg of DL-3-aminobutyric acid methyl ester, 61 mg of HOBt, 53 μl of 4-methylmorpholine and 107 mg of DCCI and carrying out flash chromatography with system N10. R$_f$(N10)=0.64.

EXAMPLE 24

Z-Phe-His-Leu-Val-2-carboxy-1-methyl-ethyl amide

A mixture of 75 mg of Z-Phe-His-Leu-Val-2-methoxycarbonyl-1o-methyl-ethyl amide (Example 23), 4 ml of methanol, 2 ml of water and 0.2 ml of 1N NaOH is stirred at room temperature for 24 hours. After the addition of 0.2 ml of 1N HCl, the whole is concentrated to dryness. The two resulting products (R$_f$(B1)=0.15 and R$_f$(B1)=0.08) are isolated by means of flash chromatography (30 g of silica gel 60, 40–63 μm, approximately 0.4 bar, eluant B1). The product-containing fraction are combined and concentrated by evaporation. The less polar diastereoisomer of the title compound has the following R$_f$ values: R$_f$(B1)=0.08 and R$_f$(S10)=0.46.

EXAMPLE 25

Pivaloyl-Phe-His-Leu-Val-Ile-His-NH$_2$

The title compound is obtained in a manner analogous to that described in Example 1 using as starting materials 9 mg of pivaloyl-Phe-His-OH and 48 mg of H-Leu-Val-Ile-His-NH$_2$, adding 17 mg of HOBt and 27 mg of DCCI and carrying out flash chromatography for purification (40 g of silica gel 60, 40–63 μm, system B9). R$_f$(B11)=0.3 and R$_f$(S10)=0.17.

The starting materials are manufactured in the following manner:

(a) Pivaloyl-Phe-His-OH is obtained by hydrolysing 1.61 g of pivaloyl-Phe-His-OMe in 50 ml of methanol/water (1:2) with 6 ml of 1N NaOH at room temperature for 45 minutes. After the addition of 6 ml of 1N HCl, concentration and drying, the title compound is obtained in the form of a white powder. R$_f$(B1)=0.96, R$_f$(S4)=0.14.

(b) Pivaloyl-Phe-His-OMe is obtained in a manner analogous to that described in Example 1 using as starting materials 1.25 g of pivaloyl-L-phenylalanine and 1.21 g of L-histidine methyl ester dihydrochloride, adding 0.77 g of HOBt, 1.01 g of 4-methylmorpholine and 1.34 g of DCCI and carrying out purification by flash chromatography with system B4. R$_f$(B2)=0.38, R$_f$(S4)=0.61.

(c) Pivaloyl-L-phenylalanine: 3.3 g of L-phenylalanine are placed in 20 ml of 1N NaOH at 0°. After the simultaneous addition of 30 ml of NaOH and 3.38 g of pivalic acid chloride in 30 ml of ether, the whole is subsequently stirred for 1 hour. 50 ml of 1N hydrochloric acid are added to the aqueous phase and extraction is carried out with ethyl acetate. The title compound is obtained by crystallisation from ether/hexane; m.p. 90°–91°.

EXAMPLE 26

(1,2:5,6-di-O-isopropylidene-α-D-glucofuranosyl-3)-acetyle-Phe-His-Leu-Val-Ile-His-NH$_2$ In a manner analogous to that described in Example 1, using as starting materials 14 mg of (1,2:5,6-di-O-isopropylidene-α-D-glucofuransoyl-3)-acetic acid dicyclohexylamine salt (produced in accordance with the directions in Arzneim.-Forsch./Drug Reg. 29, 986 (1979)) and H-Phe-His-Leu-Val-Ile-His-NH$_2$.2HCl (Example 4), after the addition of 4 mg of HOBt, 5.5 μl of 4-methylmorpholine and 7 mg of DCCI and purification by flash chromatography (35 g of silica gel 60, 40–63 μm, system B11) the title compound is obtained. R$_f$(B11)=0.46, R$_f$(S10)=0.16.

EXAMPLE 27

(1,2-O-isopropylidene-β-D-glucofuranosyl-3)-acetyl-Phe-His-Leu-Val-Ile-His-NH$_2$-bis-acetate 25 mg of (1,2:5,6-di-O-isopropylidence-α-D-glucofuranosyl-3)-acetyl-Phe-His-Leu-Val-Ile-His-NH$_2$ (Example 26) and 2.5 ml of acetic acid/water 1:1 are stirred for 24 hours at 50°. After concentration in a high vacuum, the residue is taken up in 4 ml of tert.-butanol and lyophilised, yielding the title compound in the form of a white powder. R$_f$(B17)=0.13, R$_f$(B1)=0.26.

EXAMPLE 28

Z-Phe-His-Leu-Val-7-tert.-butoxycarbonylheptyl amide

In manner analogous to that described in Example 1, using as starting materials 153 mg of Z-Phe-His-OH, 150 mg of H-Leu-Val-7-tert.-butoxycarbonylheptyl amide (Example 5a), 54 mg of HOBt and 94 mg of DCCI, the title compound is obtained after flash chromatography (100 g of silica gel 60, 40–63 μm, system B3), R$_f$(N8)=0.40, R$_f$(B4)=0.55.

EXAMPLE 29

Z-Phe-His-Leu-Val-7-carboxyheptyl amide 63 mg of Z-Phe-His-Leu-Val-7-tert.-butoxycarbonylheptyl amide (Example 28) are stirred for 10 minutes at room temperature in 1.5 ml of trifluoroacetic acid. The resulting solution is concentrated. The residue is purified by flash chromatography (30 g of silica gel 60, 40–63 μm, approximately 0.4 bar, eluant B1). The productcontaining fractions are combined and concentrated by evaporation. The residue is stirred in 2 ml of water, the solid portion is filtered off with suction and dried in a high vacuµmand the title compound is obtained in the form of a white powder. $R_f(B11)=0.14$.

EXAMPLE 30

Z-Phe-His-Leu-Val-7-(pivaloyloxymethoxycarbonyl)-heptyl amide 40 mg of Z-Phe-His-Leu-Val-7-carboxyheptyl amide (Example 29) are made into a slurry in 1 ml of ethanol and 100 μl of 1N NaOH are added. The solution is concentrated by evaporation and dried by twice making into a slurry in toluene/ethanol and concentrating by evaporation. The residue is dissolved in 0.5 ml of DMF; at 0° while stirring 12 mg of pivalic acid iodomethyl ester in 0.2 ml of DMF are added twice at an interval of 1 hour, the whole is further stirred for 16 hours at 0° and for 1 hour at room temperature and then evaporated to dryness in a high vacuum. The title compound is obtained by flash chromatography (5.5 g of silica gel, eluant methylene chloride/methanol/conecentrated ammonia 700:50:1) of the residue. $R_f(B11)=0.81$ $R_f$(methylene chloride/methanol/concentrated ammonia 700:50:1)=0.23.

EXAMPLE 31

Z-Phe-His-Leu-Val-4-tert.-butoxycarbonylbutyl amide

In a manner analogous to that described in Example 1, using as starting materials 144 mg of Z-Phe-His-OH, 138 mg of H-Leu-Val-4-tert.-butoxycarbonylbutyl amide, 51 mg of HOBt and 89 mg of DCCI, the title compound is obtained after flash chromatography (180 g of silica gel 60, 40–63 μm, system N10). $R_f(B2)=0.40$, $R_f(N8)=0.41$.

The atarting materials are manufactured in the following manner:

(a) H-Leu-Val-4-tert.-butoxycarbonylbutyl amide is obtained by hydrogenating 185 mg of Z-Leu-Val-4-tert.-butoxycarbonylbutyl amide in the presence of 30 mg of palladium-on-carbon (10%) in a manner analogous to that described in Example 4 and is further processed as a crude product. $R_f(B2)=0.17$.

(b) Z-Leu-Val-4-tert.-butoxycarbonybutyl amide is obtained in a manner analogous to that described in Example 1 using as starting materials 101 mg of Z-Leu-Val-OH, 52 mg of 5-aminovaleric acid ter.-butyl ester, 38 mg of HOBt, 33 μl of N-methylomorpholine and 68 mg of DCCI, after flash chromatography with system N4. $R_f(N4)=0.20$.

(c) 5-aminovaleric acid tert.-butyl ester is produced from 5-aminovaleric acid by way of 5-benzyloxycorbonylaminovaleric acid and 5-benzyloxycarbonylaminovaleric acid tert.-buty easter in a method and manner analogous to that described in Examples 5(c), 5(d) and 5(e).

EXAMPLE 32

Z-Phe-His-Leu-Val-4-carboxybutyl amide

In a manner analogous to that described in Example 29, the title compound is obtained by hydrolysing 68 g of Z-Phe-His-Leu-Val-4-tert.-butoxycarbonylbutyl amide with 1.5 ml of trifluoroacetic acid and flash chromatography (35 g of silica gel 60, 40–63 μm, system B22). $R_f(B11)=0.13$.

EXAMPLE 33

Z-Phe-His-Leu-val-NH$_2$

In a manner analogous to that described in Example 1, using as starting materials 87 mg of Z-Phe-His-OH, 46 mg of H-Leu-Val-NH$_2$, 31 mg of HOBt and 55 mg of DCCI, the title compound is obtained after flash chromatography (35 g of silica gel 60, 40–63 μm, system B4). $R_f(S10)=0.57$, $R_f(B2)=0.37$.

The starting materials are manufactured in the following manner:

(a) H-Leu-Val-NH$_2$ is obtained by hydrogenating 73 mg of Z-Leu-Val-NH$_2$ in the presence of 15 mg of palladium-on-carbon (10%) in a manner analogous to that described in Example 4 and is further processed as a crude product. $R_f(B2)=0.04$, $R_f(S10)=0.18$.

(b) Z-Leu-Val-NH$_2$: A mixture of 93 mg of Z-Leu-Val-OH(Example 1(e), 2 ml of methylene chloride, 39 μl of ethyldiisopropylamine and 62 mg of phosphoric acid phenyl ester anilide chloride is stirred for 30 minutes and 0.2 ml of 8N ammonia solution (in methanol) is added at room temperature. After a further 30 minutes, the precipitate is filtered off. The filtrate is concentrated and the residue is purified by means of flash chromatography (30 g of silica gel 60, 40–63 μm, approximately 0.4 bar, eluant N3). The product-containing fractions are combined and concentrated and the title compound is isolated in the form of a colourless oil. $R_f(N3)=0.20$.

Example 34

Z-Phe-His-Leu-Val-methyl amide

In a manner analogous to that described in Example 1, using as starting materials 50 mg of Z-Phe-His-OH, 28 mg of H-Leu-Val-methyl amide, 18 mg of HOBt and 31 mg of DCCI, the title compound is obtained after flash chromatography (35 g of silica gel 60, 40–63 μm, eluant system methylene chloride/methanol/concentrated ammonia 700:50:1). $R_f(B2)=0.43$, $R_f(S10)=0.68$.

The starting materials are manufactured in the following manner:

(a) H-Leu-Val-methyl amide is obtained by hydrogenating 48 mg of Z-Leu-Val-methyl amide in the presence of 10 mg of palladium-on-carbon (10%) in a manner analogous to that described in Example 4 and is further processed as a crude product. $R_f(B2)=0.08$, $R_f(S10)=0.27$.

(b) Z-Leu-Val-methyl amide: A mixture of 100 mg of Z-Leu-Val-OH (Example 1e), 2 ml of DMF, 49 mg of HOBt and 66 mg of DCCI is left to stand at 0° for 24 hours. An excess of methylamine is added to the mixture and the whole is stirred for 2 hours at 0° and for 2 hours at room temperature. The title compound is obtained in the form of a colourless oil after flash chromatography with system N3. $R_f(N7)=0.55$.

EXAMPLE 35

Z-Phe-His-Leu-Val-benzyl amide

In a manner analogous to that described in Example 1, using as starting materials 88 mg of Z-Phe-His-OH, 65 mg of H-Leu-Val-benzyl amide, 31 mg of Hobt and 54 mg of DCCI, the title compound is obtained after flash chromatography (100 g of silica gel 60, 40–63 μm, system B3). $R_f(B2)=0.60$, $Rf(S10)=0.68$.

The starting materials are manufactured in the following manner:

(a) H-Leu-Val-benzyl amide is obtained by hydrogenating 100 mg of Z-Leu-Val-benzyl amide in the presence of 20 mg of palladium-on-carbon (10%) in a manner analogous to that described in Example 4 and is further processed as a crude product. $R_f(B2)=0.20$, $R_f(S10)$ 32 0.37.

(b) Z-Leu-Val-benzyl amide: A mixture of 150 mg of Z-Leu-Val-OH (Example 1(e), 3 ml of DMF, 74 mg of HOBt and 99 mg of DCCI is left to stand at 0° for 24 hours. 55 μl of benzylamine are added to the mixture and the whole is stirred for 6 hours at 0° and for 24 hours at room temperature. The title compound is obtained in the form of a colourless oil after flash chromatography with ethyl acetate/hexane (1:2). $R_f(N7)=0.56$.

EXAMPLE 36

Z-Phe-His-Leu-Val-Dimethyl amide

In a manner analogous to that described in Example 1, using as starting materials 162 mg of Z-Phe-His-OH, 95 mg of H-Leu-Val-dimethyl amide, 57 mg of HOBt and 99 mg of DCCI, the title compound is obtained after flash chromatography (100 g of silica gel 60, 40–63 μm, system B3). $R_f(B2)=0.57$, $R_f(S10)=0.74$.

The starting materials are manufactured in the following manner:

(a) H-Leu-Val-dimethyl amide is obtained by hydrogenating 160 mg of Z-Leu-Val-dimethyl amide in the presence of 30 mg of palladium-on-carbon (10%) in a manner analogous to that described in Example 4 and is further processed as a crude product. $R_f(B2)=0.15$, $R_f(S10)=0.37$.

(b) Z-Leu-Val-dimethyl amide is obtained in the form of a colourless oil, in a manner analogous to that described in Example 35b, from 100 mg of Z-Leu-Val-OH, 2 ml of DMF, 49 mg of HOBt and 66 mg of DCCI followed by an excess of dimethylamine, after flash chromatography with ethyl acetate/hexane (1:2). $R_f(N7)=0.35$.

EXAMPLE 37

Z-Phe-His-Leu-Val-3-(m-carbamoylphenoxy)-2-hydroxypropyl amide

In a manner analogous to that described in Example 1, using as starting materials 77 mg of Z-Phe-His-OH, 37 mg of H-Leu-Val-3-(m-carbamoylphenoxy)- 2-hydroxypropyl amide, 27 mg of HOBt and 36 mg of DCCI, the title compound is obtained after flash chromatography (65 g of silica gel 60, 40–63 μm, eluant system B7). $R_f(B7)=0.15$, $R_f(N12)=0.30$.

The starting material ia manufactured in the following manner:

(a) H-Leu-Val-3-(m-carbamoylphenoxy)-2-hydroxypropyl amide: 80 mg of Z-Leu-Val-3-(m-carbamoylphenoxy)-2-hydroxypropyl amide are dissolved in 8 ml of methanol/water 9:1 and, after the addition of 20 mg of palladium-on-carbon (10%), hydrogenated with $CO_2$-absorption until saturation is reached. After 24 hours at room temperature, the catalyst is filtered off and the filtrate is concentrated and dried in a high vacuum. The tile compound is purified by flash chromatography (65 g of silica gel 60, 40–63 μm, system B11). $R_f(B11)=0.28$.

(b) Z-Leu-Val-3-(m-carbamoylphenoxy)-2-hydroxypropyl amide is obtained in a manner analogous to that described in Example 1, using as starting materials 156 mg of Z-Leu-Val-OH, 89 mg of m-(3-amino-2-hydroxypropoxy)-benzoic acid amide, 71 mg of HOBt and 111 mg of DCCI, after flash chromatorgraphy is system N11. $R_f(N11)=0.34$. $R_f(N12)=0.59$.

(c) m-(3-amino-2-hydroxypropoxy)-benzoic acid amide: 15 g of m-(2,3-epoxypropoxy)-benzoic acid amide are dissolved in 150 ml of methanol and slowly added to 155 ml of concentrated ammonia. The whole is then, in addition, heat at 40° for 2 hours, concentrated to dryness in a rotary evaporator, and the product is purified by means of flash chromatography in system B11. $R_f(B11)=0.14$.

(d) m-(2,3-epoxypropoxy)-benzoic acid amide: 16.2 g of m-hyroxybenzoic acid amide and 32.4 g of potash are refluxed for 3 hours in 120 ml of epichlorohydrin. The reaction mixture is then poured onto ice, and the product is extracted with ethyl acetate and purified by means of flash chromatography in system N10. $R_f(N10)=0.28$.

Example 38

Z-Phe-His-Leu-Val-3-(2-pyrrolidinon-1-yl)-propyl amide

In a manner analogous to that described in Example 1, using as starting materials 221 mg of Z-Phe-His-OH, 150 mg of H-Leu-Val-3-(2-pyrrolidinon-1-yl)-propyl amide, 77 mg of HOBt and 122 mg of DCCI, the title compound is obtained after flash chromatography (65 g of silica gel 60, 40–63 μm, eluant system B7). $R_f(B7)=0.26$, $R_f(N12)=0.34$.

The starting material is manufactured in the following manner:

(a) H-Leu-Val-3-(2-pyrrolidinon-1-yl)-propyl amide is obtained by hydrogenating 210 mg of Z-Leu-Val-3-(2-pyrrolidinon-1-yl)-propyl amide in the presence of 30 mg of palladium-on-carbon (10%) in a manner analogous to that described in Example 37a and is purified by flash chromatography with system B7. $R_f(B7)=0.20$, $R_f(B11)=0.47$.

(b) Z-Leu-Val-3-(2-pyrrolidinon-1-yl)-propyl amide is obtained in a manner analogous to that described in Example 1 using as starting materials 150 mg of Z-Leu-Val-OH, 64 mg of N-(3-aminopropyl)-2-pyrrolidinone, 68 mg of HOBt and 107 mg of DCCI and is purified by flash chromatography with system N10. $R_f(N10)=0.20$, $R_f(N11)=0.55$.

EXAMPLE 39

Z-Phe-His-Leu-Val-3-(N-morpholino)-propyl amide

In a manner analogous to that described in Example 1, using as starting materials 159 mg of Z-Phe-His-OH, 100 mg of H-Leu-Val-3-(N-morpholino)-propyl amide, 60 mg of HOBt and 92 mg of DCCI, the title compound is obtained after flash chromatography (65 g of silica gel 60, 40–63 μm, eluant system B7). $R_f(B7)=0.22$, $R_f(B11)=0.65$.

The starting material is manufactured in the following manner:

(a) H-Leu-Val-3-(N-morpholino)-propyl amide is obtained by hydrogenating 210 mg of Z-Leu-Val-3-(N-morpholino) -propyl amide in the presence of 30 mg of palladium-on-carbon (10%) in a manner analogous to that described in Example 37a and is purified by flash chromatography with system B11. $R_f(B11)=0.35$, $R_f(B7)=0.11$.

(b) Z-Leu-Val-3-(N-morpholino)propyl amide is obtained in a manner analogous to that described in Example 1 using as starting materials 150 mg of Z-Leu-Val-OH, 80 mg of 4-(3-aminopropyl)-morpholine, 68 mg of HOBt and 115 mg of DCCI and is purified by flash chromatography with system N11. $R_f(N11)=0.35$, $R_f(B7)=0.53$.

EXAMPLE 40

Z-Phe-His-Leu-Val-2-(2-hydroxyethylamino)-ethyl amide

In a manner analogous to that described in Example 1, using as starting materials 118 mg of Z-Phe-His-OH, 78 mg of H-Leu-Val-2-(2-hydroxyethylamino)-ethyl amide, 42 mg of HOBt and 66 mg of DCCI, the title compound is obtained after flash chromatography (65 g of silica gel 60, 40–63 μm, eluant system B11). $R_f(B11)=0.32$.

The starting material is manufactured in the following manner:

(a) H-Leu-Val-2-(2-hydroxyethylamino)-ethyl amide is obtained by hydrogenating 110 mg of Z-Leu-Val-2-(2-hydroxyethylamino)-ethyl amide in the presence of 20 mg of palladium-on-carbon (10%) in a manner analogous to that described in Example 37a and is purified by flash chromatography with system S10. $R_f(S10)=0.25$, $R_f(B11)=0.12$.

(b) Z-Leu-Val-2-(2-hydroxyethylamino)-ethyl amide is obtained in a manner analogous to that described in Example 1 using as starting materials 150 mg of Z-Leu-Val-OH, 130 mg of N-(2-hydroxyethyl)-ethylenediamine, 68 mg of HOBt and 114 mg of DCCI and is purified by flash chromatography with system B7. $R_f(B7)=0.24$, $R_f(B11)=0.67$.

EXAMPLE 41

Z-Phe-His-Leu-Val-2-(3-carbamoyl-4-hydroxyphenoxy)-ethyl amide

In a manner analogous to that described in Example 1, using as starting materials 132 mg of Z-Phe-His-OH, 95 mg of H-Leu-Val-2-(3-carbamoyl-4-hydroxyphenoxy)-ethyl amide, 46 mg of HOBt and 72 mg of DCCI, the title compound is obtained after flash chromatography (65 g of silica gel 60, 40–63 μm, eluant system B7). $R_f(B7)=0.21$, $R_f(B11)=0.56$.

The starting material is manufactured in the following manner:

(a) H-Leu-Val-2-(3-carbamoyl-4-hydroxyphenoxy)-ethyl amide is obtained by hydrogenating 240 mg of Z-Leu-Val-2-(3-carbamoyl-4-hydroxyphenoxy)-ethyl amide in the presence of 40 mg of palladium-on-carbon (10%) in a manner analogous to that described in Example 37a and is purified by flash chromatography with system B9. $R_f(B9)=0.30$, $R_f(B11)=0.40$.

(b) Z-Leu-Val-2-(3-carbamoyl-4-hydroxyphenoxy)-ethyl amide is obtained in a manner analogous to that described in Example 1 using as starting materials 147 mg of Z-Leu-Val-OH, 107 mg of 5-(1-aminoethoxy)-2-hydroxybenzoic acid amide (prepared in accordance with J. Med. Chem. 27, 831 (1984)), 61 mg of HOBt and 97 mg of DCCI and is purified by flash chromatography with system B7. $R_f(B7)=0.41$, $R_f(N7)=0.20$.

EXAMPLE 42

Z-Phe-His-Leu-Val-Ala-2-(4-imidazolyl)-ethyl amide

In a manner analogous to that described in Example 1, using as starting materials 158 mg of Z.Phe-His-OH, 110 mg of H-Leu-Val-Ala-2-(4-imidazolyl)ethyl amide, 56 mg of HOBt and 86 mg of DCCI, the title compound is obtained after flash chromatography (65 g of silica gel 60, 40–63 μm, eluant system B11). $R_f(B11)=0.42$, $R_f(B9)=0.22$.

The starting material is manufactured in the following manner;

(a) H-Leu-Val-Ala-2-(4-imidazolyl)-ethyl amide is obtained by hydrogenating 240 mg of Z-Leu-Val-Ala-2-(4dimidazolyl)-ethyl amide in the presence of 40 mg of palladium-on-carbon (10%) in a manner analogous to that described in Example 37(a) and is purified by flash chromatography with system B11. $R_f(B11)=0.20$, $R_f(B9)=0.09$.

(b) Z-Leu-Val-Ala-2-(4-imidazolyl)-ethyl amide is obtained in a manner analogous to that described in Example 1 using as starting materials 160 mg of Z-Leu-Val-OH, 100 mg of L-alanine-2-(4-imidazolyl)-ethyl amide, 67 mg of HOBt and 106 mg of DCCI and is purified by flash chromatography with system B7. $R_f(B7)=0.22$, $R_f(N11)=0.17$.

(c) L-alanine-2-(4-imidazolyl)-ethyl amide is obtained by hydrogenating 300 mg of Z-Ala-2-(4-imidazolyl)-ethyl amide in the presence of 50 mg of palladium-on-carbon (10%) in a manner analogous to that described in Example 37(a) and is purified by flash chromatography with system B11. $R_f(B11)=0.17$.

(d) Z-Ala-2-(4-imidazolyl)-ethyl amide is obtained in a manner analogous to that described in Example 1 using as starting materials 940 mg of Z-Ala-OH, 853 mg of histamine dihydrochloride, 1.6 ml of ethyldiisopropylamine, 709 mg of HOBt and 1.13 mg of DCCI and is purified by flash chromatography (200 g of silica gel 60, 40–63 μm, eluant system B7). $R_f(B7)=0.26$, $R_f(N11)=0.15$.

EXAMPLE 43

Z-Phe-His-Leu-Val-Ala-2-(2-pyridyl)-ethyl amide

In a manner analogous to that described in Example 1, using as starting materials 140 mg of Z-Phe-His-OH, 100 mg of H-Leu-Val-Ala-2-(2-pyridyl)-ethyl amide, 50 mg of HOBt and 66 mg of DCCI, the title compound is obtained after flash chromatography (65 g of silica gel 60, 40–63 μm, eluant system B7). $R_f(B7)=0.26$, $R_f(B11)=0.45$.

The starting material is manufactured in the following manner:

(a) H-Leu-Val-Ala-2-(2-pyridyl)-ethyl amide is obtained by hydrogenating 320 mg of Z-Leu-Val-Ala-2-(2-pyridyl)-ethyl amide in the presence of 50 mg of palladium-on-carbon (10%) in a manner analogous to that described in Example 37a and is purified by flash chromatography with system B9. $R_f(B9)=0.26$.

(b) Z-Leu-Val-Ala-2-(2-pyridyl)ethyl amide is obtained in a manner analogous to that described in Example 1 using as starting materials 200 mg of Z-Leu-Val-OH, 143 mg of L-alanine-2-(2-pyridyl)-ethyl amide, 91 mg of HOBt and 132 mg of DCCI and is purified by flash chromatography with system N10. $R_f(N10)=0.32$, $R_f(N11)=0.46$.

(c) L-alanine-2-(2-pyridyl)-ethyl amide is obtained by hydrogenating 900 mg of Z-Ala-2-(2-pyridyl)-ethyl amide in the presence of 100 mg of palladium-on-carbon (10%) in a manner analogous to that described in Example 37(a) and is purified by flash chromatography with system B7. $R_f(B7)=0.20$.

(d) Z-Ala-2-(2-pyridyl)-ethyl amide is obtained in a manner analogous to that described in Example 1 using as starting materials 635 mg of Z-Ala-OH, 400 mg of 2-(2-aminoethyl)-pyridine, 436 mg of HBOt and 762 mg of DCCI and is purified by flash chromatography (130 g of silica gel, system N11). $R_f(N11)=0.33$.

EXAMPLE 44

Z-Phe-His-Leu-Val-Ala-2-(2-hydroxyethylamino)-ethyl amide

In a manner analogous to that described in Example 1, using as starting materials 88 mg of Z-Phe-His-OH, 60 mg of H-Leu-Val-Ala-2-(2-hydroxyethylamino)-ethyl amide, 31 mg of HOBt and 48 mg of DCCI, the title compound is obtained after flash chromatography (65 g of silica gel 60, 40–63 μm, eluant system B11). $R_f(B11)=0.24$.

The starting material is manufactured in the following manner:

(a) H-Leu-Val-Ala-2-(2-hydroxyethylamino)-ethyl amide is obtained by hydrogenating 89 mg of Z-Leu-Val-Ala-2-(2-hydroxyethylamino)-ethyl amide in the presence of 20 mg of palladium-on-carbon (10%) in a manner analogous to that described in Example 37(a) and is further processed without purification. $R_f(B11)=0.08$, $R_f(S10)=0.10$.

(b) Z-Leu-Val-Ala-2-(2-hydroxyethylamino)-ethyl amide is obtained analogously to Example 1 using as starting materials 100 mg of Z-Leu-Val-OH, 150 mg of L-alanine-2-(2-hydroxyethylamino)-ethyl amide, 45 mg of HOBt and 76 mg of DCCI and is purified by flash chromatography with system B9. $R_f(B9)=0.33$, $R_f(B11)=0.53$.

(c) L-alanine-2-(2-hydroxyethylamino)-ethyl amide is obtained by hydrogenating 540 mg of Z-Ala-2-(2-hydroxyethylamino)-ethyl amide in the presence of 70 mg of palladium-on-carbon (10%) in a manner analogous to that described in Example 37a and is directly further used without purification. $R_f(B14)=0.17$.

(d) Z-Ala-2-(2-hydroxyethylamino)-ethyl amide is obtained in a manner analogous to that described in Example 1 using as starting materials 571 mg of Z-Ala-OH, 400 mg of N-(2-hydroxyethyl)-ethylenediamine, 470 mg of HOBt and 788 mg of DCCI and is purified by flash chromatography (160 g of silica gel, system B11). $R_f(B11)=0.23$.

EXAMPLE 45

Z-Phe-His-Leu-Val-Ala-1(S)-benzyl-2-hydroxyethyl amide

In a manner analogous to that described in Example 1, using as starting materials 110 mg of Z-Phe-His-OH, 84 mg of H-Leu-Val-Ala-1(S)-benzyl-2-hydroxyethyl amide, 38 mg of HOBt and 60 mg of DCCI, the title compound is obtained after flash chromatography (65 g of silica gel 60, 40–63 μm, eluant system B7). $R_f(B7)=0.27$.

The starting material is manufactured in the following manner:

(a) H-Leu-Val-Ala-1(S)-benzyl-2-hydroxyethyl amide is obtained by hydrogenating 210 mg of Z-Leu-Val-Ala-1(S)-benzyl-2-hydroxyethyl amide in the presence of 20 mg of palladium-on-carbon (10%) in a manner analogous to that described in Example 37a and is purified by flash chromatography with system B7. $R_f(B7)=0.16$.

(b) Z-Leu-Val-Ala-1(S)-benzyl-2-hydroxyethyl amide is obtained in a manner analogous to that described in Example 1 using as starting materials 200 mg of Z-Leu-Val-OH, 160 mg of L-alanine-1(S)-benzyl-2-hydroxyethyl amide, 110 mg of HOBt and 160 mg of DCCI and is purified by flash chromatography with system N10. $R_f(N10)=0.27$.

(c) L-alanine-1(S)-benzyl-2-hydroxyethyl amide is obtained by hydrogenating 1.3 g of Z-Ala-1(S)-benzyl-2-hydroxyethyl amide in the presence of 130 mg of palladium-on-carbon (10%) in a manner analogous to that described in Example 37a and is purified by flash chromatography with system B7. $R_f(B7)=0.28$.

(d) Z-Ala-1(S)-benzyl-2-hydroxyethyl amide is obtained in a manner analogous to that described in Example 1 using as starting materials 1.0 g of Z-Ala-OH, 680 mg of 2(S)-amino-3-phenylpropanol, 750 mg of HOBt and 1.2 g of DCCI and is purified by flash chromatography (220 g of silica gel, system N11). $R_f(N11)=0.44$.

EXAMPLE 46

Z-Phe-His-Leu-Val-Ala-1(S)-benzyl-3-cyano-2(R,S)-hydroxypropyl amide

In a manner analogous to that described in Example 1, using as starting materials 142 mg of Z-Phe-His-OH, 140 mg of H-Leu-Val-Ala-1(S)-benzyl-3-cyano-2(R,S)-hydroxypropyl amide, 54 mg of HOBt and 91 mg of DCCI, the title compound is obtained after flash chromatography (65 g of silica gel 60, 40–63 μm, eluant system B7). $R_f(B7)=0.32$.

The starting material is manufactured in the following manner:

(a) H-Leu-Val-1(S)-benzyl-3-cyano-2(R,S)-hydroxypropyl amide is obtained by hydrogenating 350 mg of Z-Leu-Val-Ala-1(S)-benzyl-3-cyano-2(R,S)-hydroxypropyl amide in the presence of 50 mg of palladium-on-carbon (10%) in a manner analogous to that described in Example 37(a) and is purified by flash chromatography with system B11. $R_f(B11)=0.46$, $R_f(B7)=0.16$.

(b) Z-Leu-Val-Ala-1(S)-benzyl-3-cyano-2-(R,S)-hydroxypropyl amide is obtained in a manner analogous to that described in Example 1 using as starting materials 240 mg of Z-Leu-Val-OH, 232 mg of L-alanine-1(S)-benzyl-3-cyano-2(R,S)-hydroxypropyl amide, 100 mg of HOBt and 159 mg of DCCI and ia purified by flash chromatography with system N7. $R_f(N7)=0.28$.

(c) L-alanine-1(S)-benzyl-3-cyano-2(R,S)-hydroxypropyl amide is obtained by hydrogenating 350 mg of Z-Ala-1(S)-benzyl-3-cyano-2(R,S)-hydroxypropyl amide in the presence of 50 mg of palladium-on-carbon (10%) in a manner analogous to that described in Example 37(a) and is purified by flash chromatography with system B7. $R_f(B7)=0.27$.

(d) Z-Ala-1(S)-benzyl-3-cyano-2(R,S)-hydroxypropyl amide is obtained in a manner analogous to that described in Example 1 using as starting materials 394 mg of Z-Ala-OH, 305 mg of 4(S)-amino-3(R,S)-hydroxy-5-phenylvaleric acid nitrile, 270 mg of HOBt and 430 mg of DCCI and is purified by flash chromatography (130 g of silica gel, system N11). $R_f(N11)=0.42$, $R_f(N7)=0.20$.

(e) 4(S)-amino-3(R,S)-hydroxy-5-phenylvaleric acid nitrile: 840 mg of N-(1(S)-benzyl-3-cyano-2(R,S)-hydroxypropyl)-phthalimide are dissolved in 20 ml of dichloromethane/methanol 3:1, 1 ml of hydrazine hydrate is added and the whole is stirred at room temperature for 20 hours. The precipitated hydrazide is removed and the title compound is purified by flash chromatography with system B7. $R_f(B7)=0.35$.

(f) N-(1(S)-benzyl-3-cyano-2(R,S)-hydroxypropyl)-phthalimide: 1.5 g of N-(1(S)-benzyl-3-cyano-2-ketopropyl)-phthalimide are dissolved in 20 ml of dichloromethane and 2 ml of methanol, cooled to $-14°$ and, over a period of 10 minutes, 90 mg of sodium borohydride are added. After 20 minutes the reaction mixtue is poured onto ice-cold 0.1N $H_2SO_4$, and the title compound is extracted with dichloromethane and purified by means of flash chromatography (system N6). The title compound consists of a diastereoisomeric mixture in a ratio of 1:1. $R_f(N6)=0.41$.

(g) N-(1(S)-benzyl-3-cyano-2-ketopropyl)-phthalimide: 2.2 g of phthaloyl-L-phenylalanine (manufactured in accordance with Houben-Weyl, volume 15/1, page 252), 0.64 ml of cyanoacetic acid tert.-butyl ester, 1.1 ml of diethylphosphorocyanidate (J. Org. Chem. 43, 3631 (1978)) and 3.3 ml of ethyldiisopropylamine are stirred intensively in 40 ml of DMF for 20 hours at 0° C. The reaction solution is concentrated, and the resulting yellow oil is dissolved in 100 ml of methylene chloride and washed twice with 0.1N $H_2SO_4$. After concentrating again, the oil is dissolved in 40 ml of trifluoroacetic acid at room temperature and after 2 hours cencentrated in a rotary evaporator. The resulting crude product is dissolved in methylene chloride, washed once with ice-water, and purified by means of flash chromatography in the system methylene chloride/ether 9:1. $R_f$(methylene chloride/ether 9:1)=0.43.

EXAMPLE 47

Z-Phe-His-Leu-Val-Ile-2-(2-pyridyl)-ethyl amide

In a manner analogous to that described in Example 1, using as starting materials 162 mg of Z-Phe-His-OH, 128 mg of H-Leu-Val-Ile-2-(2-pyridyl)-ethyl amide, 57 mg of HOBt and 88 mg of DCCI, the title compound is obtained after flash chromatography (65 g of silica gel 60, 40-63 μm, eluant system B7). $R_f(B7)=0.30$, $R_f(B11)=0.62$.

The starting material is manufactured in the following manner:

(a) H-Leu-Val-Ile-2-(2-pyridyl)-ethyl amide is obtained by hydrogenating 260 mg of Z-Leu-Val-Ile-2-(2-pyridyl)-ethyl amide in the presence of 40 mg of palladium-on-carbon (10%) in a manner analogous to that described in Example 37a and is purified by flash chromatography with system B7. $R_f(B7)=0.23$.

(b) Z-Leu-Val-Ile-2-(2-pyridyl)-ethyl amide is obtained in a manner analogous to that described in Example 1 using as starting materials 189 mg of Z-Leu-Val-OH, 180 mg of L-isoleucine-2-(2-pyridyl)-ethyl amide, 93 mg of HOBt and 144 mg of DCCI and is purified by flash chromatography with system N11. $R_f(N11)=0.45$.

(c) L-isoleucine-2-(2-pyridyl)-ethyl amide is obtained by hydrogenating 440 mg of Z-Ile-2-(2-pyridyl)-ethyl amide in the presence of 50 mg of palladium-on-carbon (10%) in a manner analogous to that described in Example 37(a) and is purified by flash chromatography with system B11. $R_f(B11)=0.65$, $R_f(N9)=0.22$.

(d) Z-Ile-2-(2-pyridyl)-ethyl amide is obtained in a manner analogous to that described in Example 1 using as starting materials 4.9 g of Z-Ile-OH-dicyclohexylamine salt, 1.75 g of 2-(2-aminoethyl)pyridine, 1.69 g of HOBt and 2.95 g of DCCI and is purified by flash chromatography (250 g of silica gel, system N11). $R_f(N11)=0.46$.

EXAMPLE 48

Z-Phe-His-Leu-Val-Ile-2-pyridyl-methyl amide

In a manner analogous to that described in Example 1, using as starting materials 130 mg of Z-Phe-His-OH, 100 mg of H-Leu-Val-Ile-2-pyridyl-methyl amide, 46 mg of HOBt and 62 mg of DCCI, the title compound is obtained after flash chromatography (65 g of silica gel 60, 40-63 μm, eluant system B7). $R_f(B7)=0.32$.

The starting material is manufactured in the following manner:

(a) H-Leu-Val-Ile-2-pyridyl-methyl amide is obtained by hydrogenating 340 mg of Z-Leu-Val-Ile-2-pyridyl-methyl amide in the presence of 50 mg of palladium-on-carbon (10%) in a manner analogous to that described in Example 37(a) and is purified by flash chromatography with system B9. $R_f(B9)=0.40$.

(b) Z-Leu-Val-Ile-2-pyridyl-methyl amide is obtained in a manner analogous to that described in Example 1 using as starting materials 220 mg of Z-Leu-Val-OH, 200 mg of L-isoleucine-2-pyridyl-methyl amide, 91 mg of HOBt and 146 mg of DCCI and is purified by flash chromatography with system N10. $R_f(N10)=0.23$.

(c) L-isoleucine-2-pyridyl-methyl amide is obtained by hydrogenating 500 mg of Z-Ile-2-pyridyl-methyl amide in the presence of 50 mg of palladium-on-carbon (10%) in a manner analogous to that described in Example 37a and is purified by flash chromatography with system B7. $R_f(B7)=0.26$, $R_f(B11)=0.65$.

(d) Z-Ile-2-pyridyl-methyl amide is obtained in a manner analogous to that described in Example 1 using as starting materials 894 mg of Z-Ile-OH-dicyclohexylamine salt, 265 mg of 2-aminomethylpyridine, 337 mg of HOBt and 536 mg of DCCI and is purified by flash chromatography (100 g of silica gel, system N7). $R_f(N7)=0.22$, $R_f(N11)=0.48$.

EXAMPLE 49

Z-Phe-His-Leu-Val-Ile-2-(3-indolyl)-ethyl amide

In a manner analogous to that described in Example 1, using as starting materials 92 mg of Z-Phe-His-OH, 79 mg of H-Leu-Val-Ile-2-(3-indolyl)-ethyl amide, 32 mg of HOBt and 44 mg of DCCI, the title compound is obtained after flash chromatography (65 g of silica gel 60, 40-63 μm, eluant system B7). $R_f(B7)=0.34$.

The starting material is manufactured in the following manner:

(a) H-Leu-Val-Ile-2-(3-indolyl)-ethyl amide is obtained by hydrogenating 210 mg of Z-Leu-Val-Ile-2-(3-indolyl)-ethyl amide in the presence of 30 mg of palladium-on-carbon (10%) in a manner analogous to that described in Example 37a and is purified by flash chromatography with system B7. $R_f(B7)=0.23$.

(b) Z-Leu-Val-Ile-2-(3-indolyl)-ethyl amide is obtained in a manner analogous to that described in Example 1 using as starting materials 121 mg of Z-Leu-Val-OH, 120 mg of L-isoleucine-2-(3-indolyl)-ethyl amide, 68 mg of HOBt and 92 mg of DCCI and is purified by flash chromatography with system N10. $R_f(N10)=0.22$, $R_f(B5)=0.53$.

(c) L-isoleucine-2-(3-indolyl)-ethyl amide is obtained by hydrogenating 800 mg of Z-Ile-2-(3-indolyl)-ethyl amide in the presence of 100 mg of palladium-on-carbon (10%) in a manner analogous to that described in Example 37a and is purified by flash chromatography with system B7. $R_f(B7)=0.43$.

(d) Z-Ile-2-(3-indolyl)-ethyl amide is obtained in a manner analogous to that described in Example 1 using as starting materials 894 mg of Z-Ile-OH-dicyclohexylamine salt, 385 mg of tryptamine, 337 mg of HOBt and 536 mg of DCCI and is purified by flash chromatography (160 g of silica gel, system N10). $R_f(N10)=0.30$, $R_f(N11)=0.70$.

EXAMPLE 50

Z-Phe-His-Leu-Val-Ile-2-(N-morpholino)-ethyl amide

In a manner analogous to that described in Example J, using as starting materials 67 mg of Z-Phe-His-OH, 54 mg of H-Leu-Val-Ile-2-(N-morpholino)-ethyl amide, 24 mg of HOBt and 37 mg of DCCI, the title compound is obtained after flash chromatography (65 g of silica gel 60, 40–63 μm, eluant system B7). $R_f(B7)=0.28$.

The starting material is manufactured in the following manner:

(a) H-Leu-Val-Ile-2-(N-morpholino)-ethyl amide is obtained by hydrogenating 160 mg of Z-Leu-Val-Ile-2-(N-morpholino)-ethyl amide in the presence of 30 mg of palladium-on-carbon (10%) in a manner analogous to that described in Example 37a and is purified by flash chromatography with system B7. $R_f(B7)=0.14$.

(b) Z-Leu-Val-Ile-2-(N-morpholino)-ethyl amide is obtained in a manner analogous to that described in Example 1 using as starting materials 133 mg of Z-Leu-Val-OH, 130 mg of L-isoleucine-2-(N-morpholino)-ethyl amide, 76 mg of HOBt and 102 mg of DCCI and is purified by flash chromatography with system B5. $R_f(B5)=0.36$.

(c) L-isoleucine-2-(N-morpholino)-ethyl amide is obtained by hydrogenating 1.0 g of Z-Ile-2(N-morpholino)-ethyl amide in the presence of 150 mg of palladium-on-carbon (10%) in a manner analgous to that described in Example 37a and is purified by flash chromatography with system B7. $R_f(B7)=0.22$.

(d) Z-Ile-2-(N-morpholino)-ethyl amide is obtained in a manner analogous to that described in Example 1 using as starting materials 1.34 g of Z-Ile-OH-dicyclohexylamine salt, 430 mg of 4-(2-aminoethyl)morpholine, 500 mg of HOBt and 801 mg of DCCI and is purified by flash chromatography (200 g of silica gel, system B7). $R_f(B7)=0.50$.

EXAMPLE 51

Z-Phe-His-Leu-Val-Ile-4-(carbamoylmethyl)-2-thiazolyl amide

In a manner analogous to that described in Example 1, using as starting materials 81 mg of Z-Phe-His-OH, 69 mg of H-Leu-Val-Ile-4-(carbamoylmethyl)-2-thiazolyl amide, 28 mg of HOBt and 39 mg of DCCI, the title compound is obtained after flash chromatography (65 g of silica gel 60, 40–63 μm, eluant system B7). $R_f(B7)=0.21$.

The starting material is manufactured in the following manner:

(a) H-Leu-Val-Ile-4-(carbamoylmethyl)-2-thiazolyl amide is obtained by hydrogenating 260 mg of Z-Leu-Val-Ile-4-(carbamoylmethyl)-2-thiazolyl amide in the presence of 100 mg of palladium-on-carbon (10%) in a manner analogous to that described in Example 37(a) and is purified by flash chromatography with system B9. $R_f(B9)=0.21$.

(b) Z-Leu-Val-Ile-4-(carbamoylmethyl)-2-thiazolyl amide is obtained in a manner analogous to that described in Example 1 using as starting materials 181 mg of Z-Leu-Val-OH, 181 mg of L-isoleucine-4-(carbamoylmethyl)-2-thiazolyl amide, 103 mg of HOBt and 138 mg of DCCI and is purified by flash chromatography with system B5. $R_f(B5)=0.20$.

(c) L-isoleucine-4-(carbamoylmethyl)-2-thiazolyl amide is obtined by hydrogenating 1.2 g of Z-Ile-4-(carbamoylmethyl)-2-thiazolyl amide in the presence of 500 mg of palladium-on-carbon (10%) in a manner analogous to that described in Example 37a and is purified by flash chromatography with system N9. $R_f(N9)=0.29$.

(d) Z-Ile-4-(carbamoylmethyl)-2-thiazolyl amide: 300 mg of Z-Ile-4-(ethoxycarbonylmethyl)-2-thiazolyl amide are dissolved in 20 ml of a 5N solution of ammonia in methanol and left to stand at room temperature for 24 hours. The reaction mixture is concentrated in a rotary evaporator and the title compound is obtained by flash chromatography with system N11. $R_f(N11)=0.33$.

(e) Z-Ile-4-(ethoxycarbonylmethyl)-2-thiazolyl amide is obtained in a manner analogous to that described in Example 1 using as starting materials 2.23 g of Z-Ile-OH-dicyclohexylamine salt, 930 mg of (2-amino-4-thiazolyl)-acetic acid ethyl ester, 842 mg of HOBt and 1.34 g of DCCI and is purified by flash chromatograhpy (250 g of silica gel, system N10). $R_f(N10)=0.53$.

EXAMPLE 52

Z-Phe-His-Leu-Val-Ile-(m-carbamoylphenyl)-methyl amide

In a manner analogous to that described in Example 1, using as starting materials 127 mg of Z-Phe-His-OH, 107 mg of H-Leu-Val-(m-carbamoylphenyl)-methyl amide, 45 mg of HOBt and 70 mg of DCCI, the title compound is obtained after flash chromatography (65 g of silica gel 60, 40–63 μm, eluant system B7). $R_f(B7)=0.20$.

The starting material is manufactured in the following manner:

(a) H-Leu-Val-Ile-(m-carbamoylphenyl)-methyl amide is obtained by hydrogenating 230 mg of Z-Leu-Val-Ile-(m-carbamoylphenyl)-methyl amide in the presence of 40 mg of palladium-on-carbon (10%) in a manner analogous to that described in Example 37a and is purified by flash chromatography with system B7. $R_f(B7)=0.11$, $R_f(B9)=0.37$.

(b) Z-Leu-Val-Ile-(m-carbamoylphenyl)-methyl amide is obtained in a manner analogous to that described in Example 1 using starting materials 164 mg of Z-Leu-Val-OH, 160 mg of L-isoleucine-(m-carbamoylphenyl)-methyl amide, 93 mg of HOBt and 126 mg of DCCI and is purified by flash chromatography with system N11. $R_f(N11)=0.39$.

(c) L-isoleucine-(m-carbamoylphenyl)-methyl amide is obtained by hydrogenating 250 mg of Z-Ile-(m-carbamoylphenyl)-methyl amide in the presence of 40 mg of palladium-on-carbon (10%) in a manner analogous to that described in Example 37a and is purified by flash chromatography with system B7. $R_f(B7)=0.27$, $R_f(B11)=0.56$.

(d) Z-Ile-(n-carbamoylphenyl)-methyl amide is obtained in a manner analogous to that described in Example 1 using as starting materials 1.78 g of Z-Ile-OH-dicyclohexylamine salt, 600 mg of 3-aminomethylbenzoic acid amide, 673 mg of HOBt and 1071 mg of DCCI and is purified by flash chromatography (220 g of silica gel, system N11). $R_f(N11)=0.37$.

EXAMPLE 53

Z-Phe-His-Leu-Val-Ile-dicarbamoylmethyl amide

In a manner analogous to that described in Example 1, using as starting materials 82 mg of Z-Phe-His-OH, 64 mg of H-Leu-Val-Ile-dicarbamoylmethyl amide, 29 mg of HOBt and 45 mg of DCCI, the title compound is obtained after flash chromatography (65 g of silica gel 60, 40-63 μm, eluant system B9). $R_f(B9)=0.37$, $R_f(B11)=0.46$.

The starting material is manufactured in the following manner:

(a) H-Leu-Val-Ile-dicarbamoylmethyl amide is obtained by hydrogenating 150 mg of Z-Leu-Val-Ile-dicarbamoylmethyl amide in the presence of 30 mg of palladium-on-carbon (10%) in a manner analogous to that described in Example 37a and is purified by flash chromatography with system B11. $R_f(B11)=0.28$.

(b) Z-Leu-Val-Ile-dicarbamoylmethyl amide is obtained in manner analogous to that described in Example 1 using as starting materials 150 mg of Z-Leu-Val-OH, 130 mg of L-isoleucine-dicarbamoylmethyl amide, 85 mg of HOBt and 115 mg of DCCI and is purified by flash chromatography with system N11. $R_f(N11)=0.25$.

(c) L-isoleucine-dicarbamoylmethyl amide is obtained by hydrogenating 560 mg of Z-Ile-dicarbamoylmethyl amide in the presence of 100 mg of palladium-on-carbon (10%) in a manner analogous to that described in Example 37a and is purified by flash chromatography with system B11. $R_f(B11)=0.22$.

(d) Z-Ile-dicarbamoylmethyl amide is obtained by reacting 1.00 g of Z-Ile-bis(methoxycarbonyl)-methyl amide with 50 ml of a 5N solution of ammonia in methanol at 40° for 2 hours and is isolated by filtering off the precipitate and drying in a high vacuum. $R_f(N9)=0.48$.

(e) Z-Ile-bis(methoxycarbonyl)-methyl amide is obtained in a manner analogous to that described in Example 1 using as starting materials 5.00 g of Z-Ile-OH-dicyclohexylamine salt, 2.1 g of aminomalonic acid dimethyl ester hydrochloride, 1.72 g of HOBt and 3.00 g of DCCI and is purified by flash chromatography (250 g of silica gel, system N6). $R_f(N6)=0.48$, $R_f(N10)=0.66$.

EXAMPLE 54

Z-Phe-His-Leu-Val-Ile-Sta-NH₂

In a manner analogous to that described in Example 1, using as starting materials 125 mg of Z-Phe-His-OH, 110 mg of H-Leu-Val-Ile-Sta-NH₂, 44 mg of HOBt and 68 mg of DCCI, the title compound is obtained after flash chromatography (65 g of silica gel 60, 40-63 μm, eluant system B7). $R_f(B7)=0.20$, $R_f(B11)=0.64$.

The starting material is manufactured in the following manner:

(a) H-Leu-Val-Ile-Sta-NH₂ is obtained by hydrogenating 250 mg of Z-Leu-Val-Ile-Sta-NH₂ in the presence of 50 mg of palladium-on-carbon (10%) in a manner analogous to that described in Example 37(a) and is purified by flash chromatography with system B7. $R_f(B7)=0.29$.

(b) Z-Leu-Val-Ile-Sta-NH₂ is obtained in a manner analogous to that described in Example 1 using as starting materials 160 mg of Z-Leu-Val-OH, 136 mg of H-Ile-Sta-NH₂, 67 mg of HOBt and 106 mg of DCCI and is purified by flash chromatography with system N11. $R_f(N11)=0.33$.

(c) H-Ile-Sta-NH₂ is obtained by hydrogenating 700 mg of Z-Ile-Sta-NH₂ in the presence of 100 mg of palladium-on-carbon (10%) in manner analogous to that described in Example 37(a) and is purified by flash chromatography with system B7. $R_f(B7)=0.20$.

(d) Z-Ile-Sta-NH₂ is obtained in a manner analogous to that described in Example 1 using as starting materials 983 mg of Z-Ile-OH-dicyclohexylamine salt, 348 mg of statin amide, 367 mg of HOBt and 536 mg of DCCI and is purified by flash chromatography (160 g of silica gel, system N11). $R_f(N11)=0.38$.

(e) Statin amide is obtained by hydrogenating 900 mg of Z-Sta-NH₂ in the presence of 120 mg of palladium-on-carbon (10%) in a manner analogous to that described in Example 4 and is purified by flash chromatography with system S9. $R_f(S9)=0.23$.

(f) Z-Sta-NH₂ is obtained by ammonolysis of 1.00 g of Z-Sta-OCH3 (manufactured as described in European Patent Application No. 111 266) in 20 ml of 5N ammonia solution in methanol at room temperature over 24 hours. The reaction solution is concentrated and the title compound is purified by flash chromatography with system S6. $R_f(S6)=0.15$.

EXAMPLE 55

Z-Phe-His-Leu-Val-Ile-His-Lys(BOC)-OMe 375 mg of Z-Phe-His-OH, 375 mg of H-Leu-Val-Ile-His-Lys (BOC)-OMe and 180 mg of N-hydroxy-5-norbornene-2,3-dicarboxylic acid imide are dissolved in 5 ml of DMF, the whole is cooled to 0° and 200 mg of DCCI are added. The whole is left to stand for approximately 15 hours at 0° and for 24 hours at room temperature, the DCH which has crystallised out is filtered off and the filtrate is concentrated to dryness at 40° in a high Vacuum. The residue is heated in 10 ml of methanol/glacial acetic acid/H₂O (94:3:3) for 1 hour at 60°, again concentrated to dryness and, for preliminary purification, subjected to Craig distribution over 800 stages in the system methanol/acetate buffer/ethylene chloride/chloroform 10:3:8:4 (acetate buffer: 14.3 ml of glacial acetic acid and 9.6 g of ammonium acetate in 1000 ml of water). The fractions containing the condensation product (K-value=0.70) are combined and concentrated to dryness. A by-product which cannot be separated off in the Craig distribution is then removed by chromatography over a column of 30 g of silica gel (Merck No. 60, 40-63 μm) eluting with chloroform-/methanol/H₂O/glacial acetic acid (150:54:10:1). The chromatographically pure fractions are combined and concentrated to dryness by evaportion, yielding the title compound in the form of an emorphous powder; $R_f(B17)=0.41$, $R_f(S4)=0.43$.

The starting materials are manufactured in the following manner:

(a) H-His-Leu-Val-Ile-His-Lys(BOC)-OMe: 465 mg of Z-Leu-Val-Ile-His-Lys(BOC)-OMe are dissolved in 10 ml of methanol/water (95:5) and, after the addition of 50 mg of palladium-on-carbon (10% Pd), hydrogenated with CO₂-absorption until saturation is reached. The catalyst is removed by filtration, and the filtrate is concentrated to dryness, pulverised and subsequently dried in a high vacuum at 40°. The title compound is obtained in an amorphous chromatographically homogeneous form. $R_f(B17)=0.25$, $R_f(B21)=0.6$.

(b) Z-Leu-Val-Ile-His-Lys(BOC)-OMe: 300 mg of Z-Leu-Val-OH, 454 mg of H-Ile-His-Lys(BOC)-OMe (manufactured as discribed in European Patent Applicaiton No. 111 266) and 136 mg of HOBt are dissolved in 5 ml of DMF, cooled to 0° and 198 mg of DCCI are added. After stirring briefly, the whole is left to stand overnight at 0° and for a further 24 hours at room temperature and then the DCH which has crystallised out is filtered off. The filtrate is concentrated in a high vacuum at 40° and the oily residue is dissolved in 12 ml of methanol/glacial acetic acid/$H_{20}$ (94:3:3) and heated for 1 hour at 60°. The solution is again concentrated to dryness and the residue is purified by Craig distribution in the system methanol/acetate buffer-/ethylene chloride/chloroform 10:3:8:4 (acetate buffer: 14.3 ml of glacial acetic acid and 9.6 g of ammonium acetate in 1000 ml of water) over 800 stages. The fractions pure according to thin layer chromatography (K=0.26) are combined, concentrated to dryness, pulverised and subsequently dried in a high vacuum at 40°. $R_f(B17)=0.70$, $R_f(S4)=0.75$.

Example 56

Z-Phe-His-Leu-Val-Ile-His-Lys-OMe 80 mg of Z-Phe-His-Leu-Val-Ile-His-Lys(BOC)-OMe (Example 55) are dissolved in 800 µl of 95% trifluoroacetic acid (duration approximately 1 minute) and left to stand for 2 minutes. The product is then precipitated by the addition of 8 ml of diisopropyl ether, left to stand for 15 minutes at 0°, filtered off, and the precipitate is washed with diisopropyl ether and dried over KOH in a high vacuum. The powder is then dissolved in 1 ml of 90trifluoroethanol, precipitated by the addition of 10 ml of 3% $MaHCO_3$ solution, filtered off, washed with $H_2O$ and dried over potassium hydroxide and phosphorus pentoxide in a high vacuum. To convert the resulting acid-free title compound into the acetate, the product is dissolved in 2 ml of 90% acetic acid and lyophilised. The title compound is a chromatographically homogeneous amorphous powder; $R_f(B17)=0.08$, $R_f(B21)=0.65$.

EXAMPLE 57

Z-Arg-His-Leu-Val-Ile-His-NH$_2$ 141 mg of Z-Arg-His-OH (containing approximately 20% NaCl), 72 mg of H-Leu-Val-Ile-His NH$_2$ (Example 1i) and 30 mg of HOBt are dissolved in 1.5 ml of DMF, cooled to 0°, 46 mg of DCCI are added and the whole is left to stand for 15 hours at 0° and for 1 day at 24°. The insoluble portion (DCH and NaCl) is filtered off, the filtrate is concentrated to dryness by evaporation, heated for 1 hour at 60° in 3 ml of methanol/glacial acetic acid/water (94:3:3), concentrated again, dissolved in 3 ml of methanol/0.1N acetic acid (1:1) and slowly filtered through a column (φ=1 cm, length=12 cm) of weakly basic ion exchanger in acetate form. The dry residue of the eluate is subjected to Craig distribution in the system n-butanol/glacial acetic acid/water (4:1:5) over 600 stages. The chromatographically pure fractions (K value approximately 0.3) are combined, concentrated to dyrness, dissolved inwater and lyophilised. $R_f(S11)=0.21$, $R_f(S5)=0.20$, $R_f(B21)=0.47$.

The starting materials are manufactured in the following manner:

(a) Z-Arg-His-OH is obtained by hydrolysing 1.84 g of Z-Arg-His-OMe hydrochloride in 18 ml of water and 7.2 ml of 1N NaOH over 2 minutes at 26° and subsequently neutralising with 7.2 ml of 1N HCl and lyopilising. $R_f(S5)=0.25$, $R_f(B21)=0.47$.

(b) Z-Arg-His-OMe: 770 mg of Z-Arg-OH, 500 mg of L-histidine methyl ester dihydrochloride, 230 µl of N-methylmorpholine and 350 mg of HOBt are dissolved in 5 ml of DMF while heating, cooled to 20°, and 600 mg of DCCI in solid form are added. The solution is left to stand for 6 hours at 20°, stirred for 1 hour at 0°, the crystalline DCH is filtered off, and the filtrate is concentrated to dryness. The semi-solid residue is heated for 1 hour at 60° in 5 ml of methanol/glacial acetic acid/water (93:3:3) and then concentrated to dryness by evaporation again. The residue is purified by chromatography over a column of 25 g of silica gel (Merck No. 60, 40–63 µm). The title compound is obtained as a hydrochloride by eluting with chloroform-/methanol (75:25). $R_f(B17)=0.13$, $R_f(B21)=0.55$.

EXAMPLE 58

Z-Arg-Phe-Leu-Val-Ile-His-NH$_2$ 130 mg of Z-Arg-Phe-OH, 91 mg of H-Leu-Val-Ile-His-NH$_2$ (Example 1i) and 38 mg of HOBt are dissolved in 1.4 ml of DMF. After the addition of 57 µl of a 5N solution of HCl in dioxam, the whole is cooled to 0° and then 58 of DCCI are added. The whole is left to stand for 20 hours at 0° and for 2 days at 25°, the DCH is filtered of at 0°, the filtrate is concentrated to dryness, and the residue is heated for 1 hour at 60° dissolved in 4 ml of methanol/glacial acetic acid/water (94:3:3) and concentrated to dryness by evaporation again. The crude product is chromatographed over a column of 20 g of silica gel (Merck No. 60, 40–63 µm) in the solvent mixture chloroform/methanol/water/glacial acetic acid (150:54:10:1). The pure fractions are concentrated to dryness by evaporation, dissolved in $H_2O$ and lyophilised, $R_f(S11)=0.35$, $R_f(B17)=0.23$, $R_f(S5)=0.52$.

The starting materials are manufactured in the following manner:

(a) Z-Arg-Phe-OH: 535 mg of Z-Arg-Phe-OMe hydrochloride are dissolved in 20 ml of methanol/$H_2O$ (1:1), 16.1 ml of 0.1N NaOH are added, the whole is stirred for 30 minutes, and then neutralised with 16.1 ml of 0.1N HCl. The solution is concentrated to 8–10 ml and lyophilised, the residue is dissolved in 5 ml of trifluoroethanol, the insoluble NaCl is filtered off and the filtrate is concentrated to dryness. The title compound, having a melting point of 193°–195°, is obtained by crystallisation from methanol/water. $R_f(S11)=0.48$, $R_f(S5)=0.43$.

(b) Z-Arg-Phe-OMe: 1.71 g of Z-Arg-OH, 1.0 g of L-phenylalanine methyl ester hydrochloride and 0.85 g of HOBt are dissolved in 10 ml of DMF while heating gently and then, at room temperature, 1.34 g of DCCI are added. The whole is stirred briefly and left to stand for 6 hours. The DCH which has crystallised out is filtered off, the filtrate is concentrated to dryness by evaporation and the residue is dissolved in 20 ml of chloroform/methanol (9:1) and purified over a column of 75 g of silica gel (Merck No. 60, 40–63 µm, eluant chloroform/methanol/water/glacial acetic acid 180:20:2:1). The chromatographically pure fractions are concentrated to dryness by evaportion, dissolved in $H_2O$ and lyophilised, dissolved once more in 0.2N HCl and again lyophilised, yielding the title compound in the form of a hydrochloride. $R_f(S11)=0.55$, $R_f(B17)=0.39$.

EXAMPLE 59

Z-His-His-Leu-Val-Ile-His-NH₂

In a manner analogous to that described in Example 1, using as starting materials 23 mg of Z-His-OH, 50 mg of H-His-Leu-Val-Ile-His-NH₂.2HCl, 11 mg of HOBt, 24,6 μl of ethyldiisopropylamine and 21 mg of DCCI, the title compound is obtained in the form of a grey resin after flash chromatography (32 g of silica gel 60, 40–63 μm, eluant system methylene chloride/methanol/water/glacial acetic acid 280:160:40:2). $R_f(B13)=0.40$.

The starting material is manufactured in the following manner:

(a) H-His-Leu-Val-Ile-His-NH₂.2HCl is obtained in a manner analogous to that described in Example 4 by hydrogenating 923 mg of Z-His-Leu-Val-Ile-His-NH₂.2HCl in the presence of 100 mg of palladium-on-carbon (10%). The crude product is recrystallised from methanol/ethyl acetate (3:1), yielding the title compound in the form of white crystals. $R_f(B13)=0.16$.

(b) Z-His-Leu-Val-Ile-His-NH₂ is obtained in a manner analogous to that described in Example 1 using as starting materials 662 mg of Z-His-OH, 1000 mg of H-Leu-Val-Ile-His-NH₂, 318 mg of HOBt and 601 mg of DCCI. The crude product is stirred in 30 ml of methylene chloride/methanol 1:1 and filtered off, and is then stirred in 20 ml of methanol and 3.67 ml of 1N HCl while cooling with an ice bath. After filtering off the undissolved DCH, the filtrate is concentrated to 6 ml, 35 ml of warm ethyl acetate are added and the whole is stirred in an ice bath, yielding the title compound in the form of white crystals. Futher amounts of the title compund are obtained from the filtrate of the methylene chloride/methanol suspension, after concentration by evaporation, by means of flash chromatogrophy (70 g of silica gel 60, 40–63 μm, eluant system methylene chloride/methnol/concentrated ammonia 1000:10:1). $R_f(B11)=0.22$.

The dihydrochloride is obtained by dissolving the title compound in methanol and adding 2.0 equivalents of 1N HCl.

EXAMPLE 60

Z-Phe-Arg-Leu-Val-Ile-His-NH₂

In a manner analogous to that described in Example 1, using as starting materials 69 mg of Z-Phe-Arg-OH, 50 mg of H-Leu-Val-Ile-His-NH₂, 16 mg of HOBt and 40 mg of DCCI, the title compound is obtained in the form of a colourless powder after flash chromatography (45 g of silica gel 60, 40–63 μm, eluant system methylene chloride/methanol/water/glacial acetic acid 330:100: 19:2). $R_f(S3)=0.16$.

The starting material is manufactured in the following manner:

(a) Z-Phe Arg-OH: 2.09 g of Z-Phe-Arg-OCH₃ (Bachem AG, Bubendorf, Switzerland) are stirred in 80 ml of methanol/water 1:1 with 6.67 ml of aqueous 1N NaOH for 3 hours at room temperature. After the addition of 6.67 ml of aqueous 1N HCl, the whole is concentrated to dryness by evaportion. The residue is stirred in a small amount of methanol, NaCl is filtered off and the filtrate is concentrated by evaporation, yielding the title compound in the form of a colourless powder. $R_f(B1)=0.26$.

EXAMPLE 61

Z-Glu-(O-tert.-butyl)-His-Leu-Val-Ile-His-NH₂

In a manner analogous to that described in Example 1, using as starting materials 64 mg of Z-Glu-(O-tert.-butyl)-OH, 120 mg of H-His-Leu-Val-Ile-His-NH₂.2HCl, 0.104 ml of ethyldiisopropylamine, 29 mg of HOBt and 47 mg of DCCI, the title compound is obtained in the form of a colourless powder after medium-pressure chromatography (LOBAR® prefabricated column, Merck, size B, 40–60 μm, system B8). $R_f(B11)=0.43$.

EXAMPLE 62

Z-Phe-Phe-Leu-Val-tris(tert.-butyldimethylsilyloxymethyl)-methyl amide

In a manner analogous to that described in Example 1, using as starting materials 22 mg of Z-Phe-Phe-OH, 31 mg of H-Leu-Val-tris(tert.-butyldimethylsilyloxymethyl)-methyl amide, 9 μl of ethyldiisopropylamine, 8 mg of HOBt and 12 mg of DCCI, the title compound is obtained in the form of a yellowish oil after medium-pressure chromatography (LOBAR® prefabricated column, Merck, size B, 40–60 μm, system B8).

The starting material is manufactured in the following manner:

(a) H-Leu-Val-tris(tert.-butydimethylsilyloxymethyl)-methyl amide is obtained in the form of a colourless oil in a manner analogous to that described in Example 4 by hydrogenating 139 mg of Z-Leu-Val-trus(-tert.-butyldimethylsilyloxymethyl)-methyl amide in the presence of 50 mg of palladium-on-carbon (5%) and medium-pressure chromatography (LOBAR® prefabricated column, size B, 40–60 μm, system methylene chloride/methanol/concentrated ammonia 175:10:1). $R_f(B8)=0.41$.

(b) Z-Leu-Val-tris(tert.-butyldimethylsilyloxymethyl)-methyl amide is manufactured by condensing 250 mg of Z-Leu-Val-OH with 286 mg og tris (tert.-butyldimethylsilyloxymethyl)-methylamine (Example 19c) and 106 μl of ethyldiisopropylamine, 94 mg of HOBt and 165 mg of DCCI in a manner analogous to that described in Example 1. After medium-pressure chromatography (LOBAR® prefabricated column, size B, 40–60 μm, system N5), the title compound is obtained in the form of a colourless oil.

EXAMPLE 63

Z-Phe-Phe-Leu-Val-tris(hydroxymethyl)-methyl amide 39 mg of Z-Phe-Phe-Leu-Val-tris(tert.-butyldimethylsilyloxymethyl)-methyl amide (Example 62) are stirred for 3 hours in 3 ml of acetic acid/H₂O 2:1. After evaporating off the sovent and medium-pressure chromatography (LOBAR® prefabricated column, size B, 40–60 μm, system B8), the title compound is obtained in the form of a colourless powder. $R_f(B8)=0.36$.

EXAMPLE 64

Z-Phe-His-Leu-Gly(phenyl)-Ile-His-NH₂ (diastereoisomer I)

49 mg of Z-Phe-His-OH, 53 mg of H-Leu-Gly(-phenyl)-Ile-His-NH2 (diastereoisomer I) and 17 mg of HOBt are dissolved at ice-bath temperature in 2 ml of DMF. After the addition of 28 mg of DCCI, the whole is stirred for 8 hours at ice-bath temperature and then for 40 hours at room temperature. After evaporating off the solvent in a high vacuum and medium-pressure chromatography (LOBAR ® prefabricated column, size B, 40–60 μm, system B9), the title compound is obtained in the form of a colourless powder. $R_f$(B11)=0.42.

The starting materials are manufactured in the following manner:

(a) H-Leu-Gly(phenyl)-Ile-His-NH$_2$ (diastereoisomer I) is obtained in the form of a colourless powder in a manner analogous to that described in Example 4 by hydrogenating 160 mg of Z-Leu--Gly(phenyl)-Ile-His-NH$_2$ (diastereoisomer I) in the presence of 50 mg of palladium-on-carbon (10%) and carrying out medium-pressure chromatography (LOBAR ® prefabricated column, size B, 40–60 μm, system B10). $R_f$(B11)=0.35.

(b) Z-Leu--Gly(phenyl)-Ile-His-NH$_2$ (diastereoisomer I) is obtained in the form of a colourless powder in a manner analogous to that described in Example 1f using as starting materials 205 mg of Z-Leu--Gly(phenyl)-OH (diastereoisomer I), 124 mg of H-Ile-His-NH$_2$, 71 mg of HOBt and 125 mg of DCCI and carrying out medium-pressure chromatography (LOBAR ® prefabricated column, size B, 40–60 μm, system B8). $R_f$(B9)=0.36.

(c) Z-Leu--Gly(phenyl)-OH (diastereoisomer I and II) is obtained by hydrolysing 1.56 g of Z-Leu-Gly-(phenyl)-OCH$_3$ (diastereoisomeric mixture) with 124 mg of water and 966 mg of potassium tert.-butoxide in ether in a manner analogous to that described in Example 1e and the diastereoisomers are separated by medium-pressure chromatography (240 g of Lichroprep ® Si 60, 25–40 μm, system N3). Diastereoisomer I: $R_f$(N3)=0.24. Diastereoisomer II: $R_f$(N3)=0.15.

(d) Z-Leu--Gly(phenyl)-OCH$_3$ (diastereoisomeric mixture) is manufactured in a manner analogous to that described in Example 1d using as starting materials 0.723 ml of diisopropylamine, 3.3 ml of butyllithium, 767 mg of phenylacetic acid methyl ester and 2.00 g of compound XXV and obtained in the form of a colourless oil after medium-pressure chromatography (LOBAR ® prefabricated column, size B, 40–60 μm, eluant system ethyl acetate/hexane 1:5). $R_f$(N4)=0.35 and 0.33.

EXAMPLE 65

Z-Phe-His-Leu-Gly(phenyl)Ile-His-NH$_2$
(diastereoisomer II)

In a manner analogous to that described in Example 64, the title compound is obtained in the form of a colourless powder using as starting materials 47 mg of Z-Phe-His-OH, 50 mg of H-Leu-Gly(phenyl)-Ile-His-NH$_2$ (diastereoisomer II), 16 mg of HOBt and 26 mg of DCCI. $R_f$(B11)=0.44.

The starting materials are manufactured in the following manner:

(a) H-Leu-Gly(phenyl-Ile-His-NH$_2$ (diastereoisomer II) is obtained in a manner analogous to that described in Example 64(a) by hydrogenating 167 mg of Z-Leu--Gly(phenyl)-Ile-His-NH$_2$ (diastereoisomer II) in the presence of 50 mg of palladium-on-carbon (10%). $R_f$(B11)=0.24.

(b) Z-Leu--Gly(phenyl)-Ile-His-NH$_2$ (diastereoisomer II) is obtained in a manner analogus to that described in Example 64b using as starting materials 289 mg of Z-Leu--Gly(phenyl)-OH (diastereoisomer II, Example 64c), 175 mg of H-Ile-His-NH$_2$, 100 mg of HOBt and 175 mg of DCCI. $R_f$(B9)=0.41.

EXAMPLE 66

Z-Phen-Leu-Gly(cyclohexyl)-Ile-His-NH$_2$
(diastereoisomer I)

Using as starting materials 98 mg of Z-Phen-His-OH, 106 mg of H-Leu-Gly(cyclohexyl)-Ile-His-NH$_2$ (diastereoisomer I), 34 mg of HOBt and 55 mg of DCCI, the title compound is obtained in the form of a colourless powder in a manner analogous to that described in Example 1 after medium-pressure chromatography (LOBAR ® prefabricated column, size B, 40–60 μm, system B9). $R_f$(B11)=0.52.

The starting materials are manufactured in the following manner:

(a) H-Leu-Gly(cyclohexyl)-Ile-His-NH$_2$ (diastereoisomer I) is obtained in the form of a colourless powder in a manner analogous to that described in Example 4 by hydrogenating 200 mg of Z-Leu-Gly(cyclohexyl)-Ile-His-NH$_2$ in the presence of 50 mg of palladium-on-carbon (10%) and carrying out medium-pressure chromatography (31 g of Lichroprep ® Si 60, 25–40 μm, system B8). $R_f$(B11)=0.39.

(b) Z-Leu--Gly(cyclohexyl)-Ile-His-NH$_2$ (diastereoisomer I) is manufactured in a manner analogous to that described in Example 1f using as starting materials 250 mg of Z-Leu-Gly(cyclohexyl)-OH (diastereoisomer I), 150 mg of H-Ile-His-NH$_2$, 86 mg of HOBt and 150 mg of DCCI and is obtained in the form of a colourless powder after medium-pressure chromatography (LOBAR ® prefabricated column, size B, 40–60 μm, system B7). $R_f$(B9)=0.35.

(c) Z-Leu-Gly(cyclohexyl)-OH (diastereoisomer I and II) is obtained by hydrolysing 1.67 g of Z-Leu-Gly(cyclohexyl)-OCH$_3$ (diastereoisomeric mixture) with 131 mg of water and 898 mg of potassium tert.-butoxide in ether in a manner analogous to that described in Example 1(e) and the diastereoisomers are separated by medium-pressure chromatography (244 g of Lichroprep ® Si 60, 25–40 μm, system ethyl acetate/hexane 1:4). Diastereoisomer I: $R_f$(N4)=0.14. Diastereoisomer II: $R_f$(N4)=0.11.

(d) Z-Leu-Gly(cyclohexyl)-OCH$_3$ (diastereoisomeric mixture) is manufacture in a manner analogous to that described in Example 1d using as starting materials 0.723 ml of diisopropylamine, 3.3 ml of butyllithium, 796 mg of cyclohexylacetic acid methyl ester and 2.00 g of compound XXV and obtained in the form of a colourless oil after medium-pressure chromatography (244 g of Lichroprep ® Si 60, 25–40 μm, system N5). $R_f$(N4)=0.35 and 0.33.

EXAMPLE 57

Z-Phe-His-Leu-Gly(cyclohexyl)-Ile-His-NH$_2$
(diastereoisomer II)

In a manner analogous to that described in Example 66, using as starting materials 91 mg of Z-Phe-His-OH, 99 mg of H-Leu-Gly(cyclohexyl)-Ile-His-NH$_2$ (diastereoisomer II), 32 mg of HOBt and 51 mg of DCCI, the title compound is obtained in the form of a colourless powder. $R_f$(B11)=0.61.

The starting materials are manufactured in the following manner:

(a) H-Leu-Gly(cyclohexyl)-Ile-His-NH$_2$ (diastereoisomer II) is obtained in a manner analogous to that described in Example 66a by hydrogenating 180 mg of Z-Leu-Gly(cyclohexyl)-Ile-His-NH$_2$ (diastereoisomer II) in the presence of 50 mg of palladium-on-carbon (10%). R$_f$(B11)=0.38.

(b) Z-Leu-Gly(cyclohexyl)-Ile-His-NH$_2$ (diastereoisomer II) is obtained in a manner analogous to that described in Example 66b using as starting materials 250 mg of Z-Leu-Gly(cyclohexyl)-OH (idastereoisomer II, Example 66c), 150 mg of H-Ile-His-NH$_2$, 86 mg of HOBt and 150 mg of DCCI. R$_f$(B9)=0.47.

EXAMPLE 68

Z-Phe-His-Leu-Gly(n-octyl)-Ile-His-NH$_2$

Using as starting materials 112 mg of Z-Phe-His-OH, 128 mg of H-Leu-Gly(n-octyl)-Ile-His-NH$_2$, 39 mg of HOBt and 62 mg of DCCI, the title compound is obtained in the form of a colourless powder in a manner analogous to that described in Example 1 after medium-pressure chromatography (LOBAR ® prefabricated column, size B, 40–60 μm, system B8). R$_f$(B9)=0.29.

The starting materials are obtained in the following manner:

(a) H-Leu-Gly(n-octyl)-Ile-His-NH$_2$ is obtained in the form of a colourless resin by hydrogenating 269 mg of Z-Leu-Gly(n-octyl)-Ile-His-NH$_2$ in the presence of 40 mg of palladium-on-carbon in a manner analogous to that described in Example 4 and carrying medium-pressure chromatography (LOBAR ® prefabricated column, size B, 40–60 μm, system B9). R$_f$(B11)=0.35.

(b) Z-Leu-Gly(n-octyl)-Ile-His-NH$_2$ is manufactured in a manner analogous to that described in Example 1f using as starting materials 413 mg of Z-Leu-Gly((n-octyl)-OH, 232 mg of H-Ile-His-NH-hd 2, 133 mg of HOBt and 233 mg of DCCI and is obtained in the form of a colourless powder after medium-pressure chromatography (LOBAR ® prefabricated column, size B, 40–60 μm, system B7). R$_f$(B11)=0.64 and 0.58 (diastereoisomeric mixture).

(c) Z-Leu-Gly(n-octyl)-OH is obtained in the form of a colourless oil by hydrolysing 827 mg of Z-Leu-Gly(n-octyl)-OCH$_3$ with 85 mg of water and 569 mg of potassium tert.-butoxide in ether in a manner analogous to that described in Example 1c and carrying out medium-pressure chromatography (LOBAR ® prefabricated column, size B, 40–60 μm, system N5). R$_f$(N4, developed twice)=0.20 and 0.15 (diastereoisomeric mixture).

(d) Z-Leu-Gly(n-octyl)-OCH$_3$ is manufactured in a manner analogous to that described in Example 1(d) using as starting materials 1.21 ml of diisopropylamine, 5.5 ml of butyllithium, 1595 mg of decanoic acid methyl ester and 738 mg of compound XXV and is obtained in the form of a colourless oil after medium-pressure chromatography (LOBAR ® prefabricated column, size B, 40–60 μm, system: 100% hexane).

EXAMPLE 69

BOC-Phe-(N-methyl-Phe)-Leu-Val-methyl amide

In a manner analogous to that described in Example 1, using as starting materials 72 mg of BOC-Phe-(N-methyl-Phe)-OH, 41 mg of H-Leu-Val-methyl aminde (Example 34(a), 26 mg of HOBt and 45 mg of DCCI in 2.5 ml of DMF, the title compound is obtained in the form of a white amorphous powder after flash chromatography (35 g of silica gel 60, 40–63 μm, ethyl acetate/hexane 4:1). R$_f$(N10)=0.37.

The starting material is manufactured in the following manner:

(a) BOC-Phe-(N-methyl-Phe)-OH is manufactured by condensing BOC-Phe-Oh with N-methyl-L-phenylalanine methyl ester (Bachem AG, Bubendorf, Switzerland) analogously to the directions in Chem. Pharm. Bull. 26, 3588 (1978) and subsequently hydrolysing the methyl ester with NaOH in a manner analogous to that described in Example 15(a).

EXAMPLE 70

BOC-Phe-(N-methyl-Phe)-Leu-Val-Ile-His-NH$_2$

In a manner analogous to that described in Example 1, using as starting materials 47 mg of BOC-Phe-(N-methyl-Phe)-OH, 48 mg of H-Leu-Val-Ile-His-NH$_2$, 17 mg of HOBt and 27 mg of DCCI in 2 ml of DMF, the title compound is obtained in the form of a white amorphous powder after flash chromatography (35 g of silica gel 60, 40–63 μm, system B4). R$_f$(B11)=0.77, R$_f$(S4)=0.46.

EXAMPLE 71

The following can be manufactured analogously to the foregoing Examples:

Z-Phe-His-Leu-Val-Ile-tert.-butyl ester, R$_f$(B4)=0.40.
Ac-Phe-His-Leu-Val-Ile-His-NH$_2$, R$_f$(B11)=0.24 and R$_f$(S4)=0.10.
Z-Phe-His-Leu-Val-Ile-(N-ethoxycarbonyl-4-piperidyl)-amide, R$_f$(B7)=0.31.
α-(benzyloxycarbonylamino)-α-methoxycarbonylacetyl-Phe-His-Leu-Val-3-(2pyrrolidinon-1yl)-propyl amide, R$_f$(B7)=0.30.
Z-Phe-His-Leu-Val-Ala-bis-(2-hydroxyethylamnocarbamoyl)-methyl amide, R$_f$(B9)=0.25 and R$_f$(B11)=0.57.
Z-Phe-His-Leu-Val-Ala-1hydroxymethyl-2-(4-imidazolyl)-ethyl amide, R$_f$(B9)=0.2 and R$_f$(B11)=0.47.
H-Sta-Phe-His-Leu-Val-Ile-His-NH$_2$, R$_f$(B13)=0.25.
(2R,3R)-2,3-dihydroxy-3-carboxypropionyl-Phe-His-Leu-Val-Ile-His-NH$_2$, R$_f$(methylene chloride/methanol/concentrated ammonia 5:3:1)=0.38.
Z-Phe-His-Leu-Val-carbamoyl-(3-methoxycarbonyl-2-hydroxy-1-isobutylpropylamnocarbonyl)-methyl amide, R$_f$(B7)=0.28.
Z-Phe-His-Leu-Val-Gly-Gly-tris(hydroxymethyl)-methyl amide, R$_f$(B11)=0.30.
Z-Arg-Arg-Leu-Val-Ile-His-NH$_2$, R$_f$(S11)=0.18.

EXAMPLE 72

Gelatine solution

A sterile-filtered aqueous solution of Z-Phe-His-Leu-Val-Ile-His-NH$_2$ is mixed under aseptic conditions, while heating, with a sterile gelatine solution that contains phenol as preservative, in such proportions that 1.0 ml of solution has the following composition:

| | |
|---|---|
| Z-Phe-His-Leu-$^c$-Val-Ile-His-NH$_2$ | 3 mg |
| gelatine | 150.0 mg |
| phenol | 4.7 mg |
| distilled water to make up to | 1.0 ml |

The mixture is filled under aseptic conditions into 1.0 ml phials.

EXAMPLE 73

Sterile dry substance for injection 5 mg of Z-Phe-His-Leu-Val-Ile-His-NH$_2$ are dissolved in 1 ml of an aqueous solution with 20 mg of mannitol. The solution is sterile-filtered, introduced under aseptic conditions into a 2 ml ampoule, deep-frozen and lyophilised. Before use, the lyophilisate is dissolved in 1 ml of distilled water or 1 ml of physiological salt solution. The solution is admisitered intrasmuscularly or intravenously. This formulation can also be introduced into double-chamber injection ampoules.

EXAMPLE 74

Nasal spray 500 mg of finely ground (<5.0 μm) Z-Phe-His-Leu-Val-Ile-His-NH₂ are suspended in a mixture of 3.5 ml of "Myglyol 812" and 0.08 g of benzyl alcohol. This suspension is introduced into a container with a dosing valve. 5.0 g of "Freon 12" are introduced through the valve into the container under pressure. By shaking, the "Freon" is dissolved in the myglyol/benzyl alcohol mixture. This spray container contains approximately 100 single doses which can be administered individually.

We claim:

1. A process for the preparation of a compound of the formula

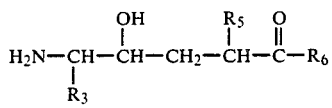 (VIII)

wherein $R_3$ is hydrogen, lower alkyl, cycloalkyl, aryl-lower alkyl, or aryl;

$R_5$ is lower alkyl, cycloalkyl, aryl-lower alkyl, or aryl; and $R_6$ is (A) amino;

(B) mono or di-substituted amino or substituted hydroxy, which substituents are selected from
 (i) unsubstituted and substituted, saturated and unsaturated, aliphatic hydrocarbon radicals having up to and including 18 carbon atoms; and
 (ii) aromatic, heteroaromatic, aromatic-aliphatic and heteroaromatic-aliphatic radicals having up to and including 18 carbon atoms;

(C) a natural alpha-amino acid residue that is N-terminally bound to the group —CO—, said natural alpha-amino acid being C-terminally free, esterified, or amidated;

(D) a di- or tri-peptide residue consisting of amino acids selected from natural alpha-amino acids and statin, said di- or tri-peptide being N-terminally bound to the group —CO— and, being C-terminally free, esterfied, or amidated;

and salts thereof comprising:

(a) converting a compound of the formula

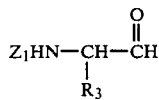 (IX)

wherein $R_3$ is as defined above and $Z_1$ is an amino-protecting group, with a methylide selected from dialkylsulphonium methylide, alkyl or phenyl dialkylamino sulphoxonium methylide, and dialkylsulphoxonium methylide, into an expoxide of the formula

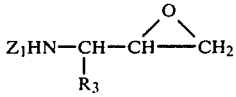 (X)

wherein $Z_1$ and $R_3$ are as defined above;

(b) reacting said epoxide of formula (X) with a nucleofugal leaving group X introducing agent to result in the compound of the formula

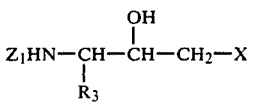 (XI)

wherein $R_3Z_1$ and X are as defined above;

(c) reacting a compound of formula (XI) with a carbonyl compound of the formula

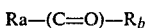 (XII)

wherein each of $R_a$ and $R_b$ are independently hydrogen, lower alkyl, aryl, or aryl-lower alkyl, or $R_a$ and $R_b$ together are an alkylidene or bridged alkylidene having 4–12 carbon atoms, or a reactive derivative of said carbonyl compound, in the presence of an acidic reagent to result in a compound of the formula

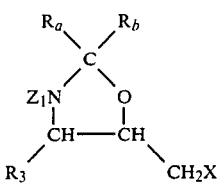 (XIII)

wherein $R_a$, $R_b$, $R_3$, $Z_1$, and X are as defined above;

(d) reacting said compound of formula (XIII) with a carboxylic acid ester salt of the formula

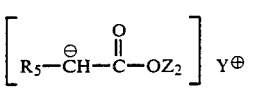 (XIV)

wherein $R_5$ is as defined above, $Z_2$ is a carboxy protecting group and $Y^\ominus$ is a cation to yield a compound of the formula

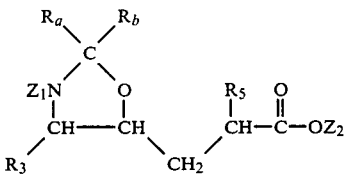 (XV)

wherein $R_a$, $R_b$ $R_3$, $R_5$, $Z_1$, and $Z_2$ are as defined above;

(e) removing said carboxy-protecting group $Z_2$;

(f) opening the ring of formula (XV) with a solvolysis reagent; and then (g) removing said protecting group $Z_1$.

2. The process of claim 1 further comprising separating the individual isomers found in the resultant mixture from step (e) before proceeding to step (f).

3. The process of claim 1 further comprising replacing the group $OZ_2$ of formula XV with the group $R_6$ in place of step e to result in a compound of the formula
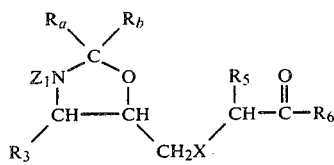
wherein $R_a$, $R_b$, $R_3$, $R_5$, $Z_1$, and $R_6$ are defined as in claim 1.
* * * * *